US011591366B2

(12) United States Patent
Marsault et al.

(10) Patent No.: US 11,591,366 B2
(45) Date of Patent: Feb. 28, 2023

(54) MACROCYCLIC COMPOUNDS AND METHODS OF PREVENTING OR TREATING PAIN

(71) Applicant: SOCPRA SCIENCES SANTÉ ET HUMAINES S.E.C., Sherbrooke (CA)

(72) Inventors: Éric Marsault, Sherbrooke (CA); Marc Sousbie, Grenoble (FR); Richard Leduc, Sherbrooke (CA); Philippe Sarret, Sherbrooke (CA); Jean-Michel Longpré, Magog (CA); Élie Besserer-Offroy, Sherbrooke (CA); Rebecca Brouillette, Sherbrooke (CA); Michael Desgagné, Val d'Or (CA)

(73) Assignee: SOCPRA SCIENCES SANTÉ ET HUMAINES S.E.C., Sherbrooke (CA)

( * ) Notice: Subject to any disclaimer, the term of this patent is extended or adjusted under 35 U.S.C. 154(b) by 472 days.

(21) Appl. No.: 16/011,118

(22) Filed: Jun. 18, 2018

(65) Prior Publication Data
US 2018/0362582 A1  Dec. 20, 2018

Related U.S. Application Data

(60) Provisional application No. 62/520,980, filed on Jun. 16, 2017.

(51) Int. Cl.
| | | |
|---|---|---|
| *A61K 38/08* | (2019.01) | |
| *C07K 7/06* | (2006.01) | |
| *A61P 29/00* | (2006.01) | |
| *A61P 9/02* | (2006.01) | |
| *A61K 45/06* | (2006.01) | |
| *A61P 25/00* | (2006.01) | |
| *C07K 7/08* | (2006.01) | |

(52) U.S. Cl.
CPC ............... *C07K 7/06* (2013.01); *A61K 38/08* (2013.01); *A61K 45/06* (2013.01); *A61P 9/02* (2018.01); *A61P 25/00* (2018.01); *A61P 29/00* (2018.01); *C07K 7/083* (2013.01)

(58) Field of Classification Search
None
See application file for complete search history.

(56) References Cited

U.S. PATENT DOCUMENTS

2017/0114004 A1* 4/2017 Mansha ................ C07C 231/12

OTHER PUBLICATIONS

Lin, Yuya A. et al, "Olefin metathesis for site selective protein modification." ChemBioChem (2009) 10 p. 959-969.*
Hampton Research sales literature for reductive alkylation (copyright 2010).*

Akunne, H. C.; Darling, S.; Zoski, K.; Setter, a M.; He, J. X.; Sawyer, T. K.; Pugsley, T. A.; Cody, W. L. Functional Activity of New C-Terminal Cyclic-Neurotensin Fragment Analogs Neuropeptides 1996, 30 (3), 213-218.
Barelli, H.; Vincent, J. P.; Checler, F. Rat kidney endopeptidase 24.16. Purification, physico-chemical characteristics and differential specificity towards opiates, tachykinins and neurotensin-related peptides. Eur. J. Biochem. 1993, 211,79-90.
Barroso, S.; Richard, F.; Nicolas-Etheve, D.; Reversal, J. L.; Bernassau, J. M.; Kitabgi, P.; Labbé-Jullié, C. Identification of Residues Involved in Neurotensin Binding and Modeling of the Agonist Binding Site in Neurotensin Receptor 1. J. Biol. Chem. 2000, 275 (1), 328-336.
Beck, J. G.; Chatterjee, J.; Laufer, B.; Kiran, M. U.; Frank, A. O.; Neubauer, S.; Ovadia, O.; Greenberg, S.; Gilon, C. Hoffman, A.; et al. Intestinal Permeability of Cyclic Peptides: Common Key Backbone Motifs Identified. J. Am. Chem. Soc. 2012, 134 (29), 12125-12133.
Bernard, Stephen A.; Gray, Timothy W.; Buist, Michael D.; Jones, Bruce M.; Silvester, William; Gutteridge, Geoff Smith, Karen (Feb. 21, 2002). "Treatment of Comatose Survivors of Out-of-Hospital Cardiac Arrest with Induced Hypothermia". New England Journal of Medicine. 346 (8): 557-563.
Besserer-Offroy, É.; Brouillette, R. L.; Lavenus, S.; Froehlich, U.; Brumwell, A.; Murza, A.; Longpré, J.-M.; Marsault, É.; Grandbois, M.; Sarret, P.; et al. The Signaling Signature of the Neurotensin Type 1 Receptor with Endogenous Ligands. Eur. J. Pharmacol. 2017, 805, 1-13.
Binder, E. B.; Kinkead, B.; Owens, M. J.; Nemeroff, C. B. Neurotensin and Dopamine Interactions. Pharmacol. Rev. 2001, 53 (4), 453-486.

(Continued)

*Primary Examiner* — Fred H Reynolds
(74) *Attorney, Agent, or Firm* — Lavery, De Billy, LLP; Julie Gauvreau

(57) ABSTRACT

The present invention provides a macrocyclic compound of formula (I)

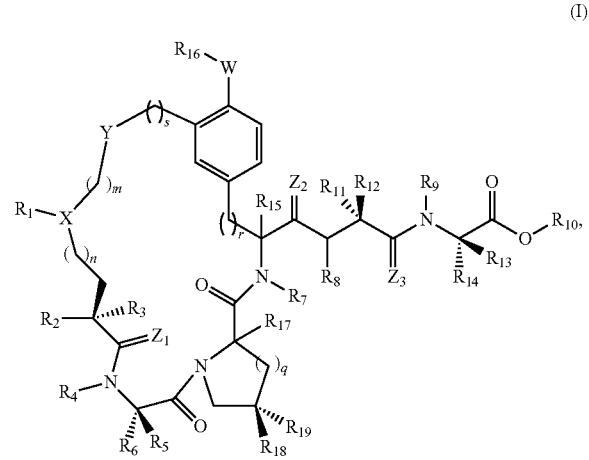

compositions and kits comprising this compound and their use for preventing or treating pain, or inducing hypothermia or hypotension.

30 Claims, 18 Drawing Sheets

Specification includes a Sequence Listing.

(56) References Cited

OTHER PUBLICATIONS

Bingham A.L., Hughes D.S., Hursthouse M.B., Lancaster R.W., Tavener S.and Threlfall T.L., 2001. Over one hundred solvates of sulfathiazole Chem. Commun., 2001, 7:603-604.

Bird, J. L.; Simpson, R.; Vllasaliu, D.; Goddard, A. D. Neurotensin Receptor 1 Facilitates Intracellular and Transepithelial Delivery of Macromolecules. Eur. J Pharm. Biopharm 2017, 119, 300-309.

Biron, E.; Chatterjee, J.; Kessler, H. Optimized Selective N-Methylation of Peptides on Solid Support. J. Pept. Sci. 2006, 12(3), 213-219.

Bittermann, H.; Einsiedel, J.; Hubner, H.; Gmeiner, P. Evaluation of Lactam-Bridged Neurotensin Analogues Adjusting psi(Pro10) close to the Experimentally Derived Bioactive Conformation of NT(8-13). J. Med. Chem. 2004, 47 (22), 5587-5590.

Blackwell, H. E.; Sadowsky, J. D.; Howard, R. J.; Sampson, J. N.; Chao, J. A.; Steinmetz, W. E.; O'Leary, D. J.; Grubbs, R. H. Ring-Closing Metathesis of Olefinic Peptides: Design, Synthesis, and Structural Characterization of Macrocyclic Helical Peptides. J. Org. Chem. 2001, 66 (16), 5291-5302.

Bodnar, R. J. Endogenous Opiates and Behavior: 2015. Peptides 2017, 88 (12), 126-188.

Boules, M.; Fredrickson, P.; Richelson, E. Current Topics: Brain Penetrating Neurotensin Analog. Life Sci. 2003, 73 (22), 2785-2792.

Bredeloux, P.; Cavelier, F.; Dubuc, I.; Vivet, B.; Costentin, J.; Martinez, J. Synthesis and Biological Effects of c(Lys-Lys-Pro-Tyr-Ile-Leu-Lys-Lys-Pro-Tyr-Ile-Leu) (JMV2012), a New Analogue of Neurotensin That Crosses the Blood-Brain Barrier. J. Med. Chem. 2008, 51 (6), 1610-1616.

Brik, A. Metathesis in Peptides and Peptidomimetics. Adv. Synth. Catal. 2008, 350 (11-12), 1661-1675.

Buhler, A. V; Choi, J.; Proudfit, H. K.; Gebhart, G. F. Neurotensin Activation of the NTR1 on Spinally-Projecting Serotonergic Neurons in the Rostral Ventromedial Medulla Is Antinociceptive. Pain 2005, 114 (1-2), 285-294.

Caira MR et al. 2004. Preparation and Crystal Characterization of a Polymorph, a Monohydrate, and an Ethyl Acetate Solvate of the Antifungal Fluconazole. J Pharm Sci 93 (3), 601-611.

Carraway, R.; Leeman, S. E. The Isolation of a New Hypotensive Peptide, Neurotensin, from Bovine Hypothalami. J. Biol. Chem. 1973, 248 (19), 6854-6861.

Checler, F.; Vincent, J. P.; Kitabgi, P. Neurotensin Analogs [D-TYR11] and [D-PHE11]Neurotensin Resist Degradation by Brain Peptidases in Vitro and in Vivo. J. Pharmacol. Exp. Ther. 1983, 227 (3), 743-748.

Cheng, Y.C.; Prusoff, W. H. Relationship between the Inhibition Constant (Ki) and the Concentration of Inhibitor Which Causes 50 per Cent Inhibition (IC50) of an Enzymatic Reaction. Biochem. Pharmacol. 1973, 22 (23), 3099-3108.

Clineschmidt, B. V; McGuffin, J. C. Neurotensin Administered Intracisternally Inhibits Responsiveness of Mice to Noxious Stimuli. Eur. J. Pharmacol. 1977, 46 (4), 395-396.

Clineschmidt, B. V.; McGuffin, J. C.; Bunting, P. B. Neurotensin: Antinocisponsive Action in Rodents. Eur. J. Pharmacol 1979, 54 (1-2), 129-139.

Coderre, T. J. The Role of Excitatory Amino Acid Receptors and Intracellular Messengers in Persistent Nociception after Tissue Injury in Rats. Mol. Neurobiol. 1993, 7 (3-4), 229-246.

Connelly, J. C.; Skidgel, R. A.; Schulz, W. W.; Johnson, A. R.; Erdos, E. G. Neutral endopeptidase 24.11 in human neutrophils: cleavage of chemotactic peptide. Proc. Natl. Acad. Sci. U. S. A. 1985, 82, 8737-8741.

Da Costa, G.; Bondon, A.; Coutant, J.; Curmi, P.; Monti, J.-P. Intermolecular Interactions between the Neurotensin and the Third Extracellular Loop of Human Neurotensin 1 Receptor. J. Biomol. Struct. Dyn. 2012, No. November, 37-41.

Dobner, P. R. Neurotensin and Pain Modulation. Peptides 2006, 27 (10), 2405-2414.

Driggers, E. M.; Hale, S. P.; Lee, J.; Terrett, N. K. The Exploration of Macrocycles for Drug Discovery—an Underexploited Structural Class. Nat. Rev. Drug Discov. 2008, 7 (7), 608-624.

Dubuc, I.; Costentin, J.; Doulut, S.; Rodriguez, M.; Martinez, J.; Kitabgi, P. JMV 449: a pseudopeptide analogue of neurotensin-(8-13) with highly potent and long-lasting hypothermic and analgesic effects in the mouse. Eur. J. Pharmacol. 1992, 219, 327-329.

Dubuisson, D.; Dennis, S. G. The Formalin Test: A Quantitative Study of the Analgesic Effects of Morphine, Meperidine, and Brain Stem Stimulation in Rats and Cats. Pain 1977, 4 (C), 161-174.

Egloff, P.; Hillenbrand, M.; Klenk, C.; Batyuk, A.; Heine, P.; Balada, S.; Schlinkmann, K. M.; Scott, D. J.; Schutz, M.; Plückthun, A. Structure of Signaling-Competent Neurotensin Receptor 1 Obtained by Directed Evolution in *Escherichia coli*. Proc. Natl. Acad. Sci. U. S. A. 2014, 111 (6), E655-62.

Einsiedel, J.; Hübner, H.; Hervet, M.; Härterich, S.; Koschatzky, S.; Gmeiner, P. Peptide Backbone Modifications on the C-Terminal Hexapeptide of Neurotensin. Bioorganic Med. Chem. Lett. 2008, 18 (6), 2013-2018.

Fanelli, R.; Besserer-Offroy, É.; René, A.; Côté, J.; Tétreault, P.; Collerette-Tremblay, J.; Longpré, J.-M.; Leduc, R.; Martinez, J.; Sarret, P.; et al. Synthesis and Characterization in Vitro and in Vivo of (L)-(Trimethylsilyl)alanine Containing Neurotensin Analogues J. Med. Chem. 2015, 58 (19), 7785-7795.

Feng, Y. P.; Wang, J.; Dong, Y. L.; Wang, Y. Y.; Li, Y. Q. The roles of neurotensin and its analogues in pain. Curr. Pharm. Des 2015, 21, 840-848.

Glas, A.; Wamhoff, E.-C.; Kruger, D. M.; Rademacher, C.; Grossmann, T. N. Increased Conformational Flexibility of a Macrocycle-Receptor Complex Contributes to Reduced Dissociation Rates. Chemistry 2017, 23 (64), 16157-16161.

Glimcher, P. W.; Margolin, D. H.; Giovino, a a; Hoebel, B. G. Neurotensin: A New "Reward Peptide". Brain Res. 1984, 291 (1), 119-124.

Guillemette, A.; Dansereau, M. A.; Beaudet, N.; Richelson, E.; Sarret, P. Intrathecal Administration of NTS1 Agonists Reverses Nociceptive Behaviors in a Rat Model of Neuropathic Pain. Eur. J. Pain 2012, 16, 473-484.

Hong, S. H.; Sanders, D. P.; Lee, C. W.; Grubbs, R. H. Prevention of Undesirable Isomerization during Olefin Metathesis. J. Am. Chem. Soc. 2005, 127 (49), 17160-17161.

Kaiser, E.; Colescott, R. L.; Bossinger, C. D.; Cook, P. I. Color Test for Detection of Free Terminal Amino Groups in the Solid-Phase Synthesis of Peptides. Anal. Biochem. 1970, 34 (2), 595-598.

Kennedy, J. D. Neuropathic Pain: Molecular Complexity Underlies Continuing Unmet Medical Need. J. Med. Chem. 2007, 50(11), 2547-2556.

Khatun, U. L.; Goswami, S. K.; Mukhopadhyay, C. Modulation of the Neurotensin Solution Structure in the Presence of Ganglioside GM1 Bicelle. Biophys. Chem. 2012, 168-169, 48-59.

Kleczkowska, P.; Lipkowski, A. W. Neurotensin and neurotensin receptors: characteristic, structure-activity relationship and pain modulation—a review. Eur. J. Pharmacol. 2013, 716,54-60.

Kleczkowzka, P.; Lipkowski, A. W. Neurotensin and Neurotensin Receptors: Characteristic, Structure-Activity Relationship and Pain Modulation—A Review. Eur. J. Pharmacol. 2013, 716 (1-3), 1-7.

Krogsgaard-Larsen, et al., Textbook of Drug Design and Development (2d Ed. 1996), entire book.

Krumm, B. E.; Lee, S.; Bhattacharya, S.; Botos, I.; White, C. F.; Du, H.; Vaidehi, N.; Grisshammer, R. Structure and Dynamics of a Constitutively Active Neurotensin Receptor. Sci. Rep. 2016, 6, 38564.

Lee, S.; Bhattacharya, S.; Tate, C. G.; Grisshammer, R.; Vaidehi, N. Structural Dynamics and Thermostabilization of Neurotensin Receptor 1. J. Phys. Chem. B 2015, 119 (15), 4917-4928.

Li et al. Tetrahedron Letters, 2017, 58 (24) 2374-2377.

Luca, S.; White, J. F.; Sohal, A. K.; Filippov, D. V; van Boom, J. H.; Grisshammer, R.; Baldus, M. The Conformation of Neurotensin Bound to Its G Protein-Coupled Receptor. Proc. Natl. Acad Sci. U. S. A. 2003, 100 (19), 10706-10711.

Lundquist, J. T.; Dix, T. A. Preparation and Receptor Binding Affinities of Cyclic C-Terminal Neurotensin (8-13) and (9-13) Analogues. Bioorg. Med. Chem. Lett. 1999, 9 (17), 2579-2582.

(56) References Cited

OTHER PUBLICATIONS

Marsault, E.; Peterson, M. L. Macrocycles Are Great Cycles: Applications, Opportunities, and Challenges of Synthetic Macrocycles in Drug Discovery. J. Med. Chem. 2011, 54 (7), 1961-2004.
Marsault, É.; Peterson, M. L. Practical Medicinal Chemistry with Macrocycles: Design, Synthesis, and Case Studies, Wiley.; Marsault, É., Peterson, M. L., Eds.; Wiley: Hoboken, NJ, USA, 2017, table of contents only.
Maruta et al. J. Org. Chem. 1986, 51, 5083-5092.
Nemeroff, C. B.; Osbahr, A. J.; Manberg, P. J.; Ervin, G. N.; Prange, A. J. Alterations in Nociception and Body Temperature after Intracisternal Administration of Neurotensin, Beta-Endorphin, Other Endogenous Peptides, and Morphine. Proc. Natl. Acad. Sci. U. S. A. 1979, 76 (10), 5368-5371.
Pang, Y. P.; Cusack, B.; Groshan, K.; Richelson, E. Proposed Ligand Binding Site of the Transmembrane Receptor for neurotensin(8-13). J. Biol. Chem. 1996, 271 (25), 15060-15068.
Patgiri, A.; Menzenski, M. Z.; Mahon, A. B.; Arora, P. S. Solid-Phase Synthesis of Short α-Helices Stabilized by the Hydrogen Bond Surrogate Approach. Nat. Protoc. 2010, 5 (11), 1857-1865.
Peberdy, MA; Callaway, CW; Neumar, RW; Geocadin, RG; Zimmerman, JL; Donnino, M; Gabrielli, A; Silvers, SM; Zaritsky, AL; Merchant, R; Vanden Hoek, TL; Kronick, SL; American Heart Association (Nov. 2, 2010). "Part 9: post-cardiac arrest care: 2010 American Heart Association Guidelines for Cardiopulmonary Resuscitation and Emergency Cardiovascular Care.". Circulation. 122 (18 Suppl 3): S768-86.
Pérez de Vega, M. J.; Garcia-Aranda, M. I.; González-Muñiz, R. A Role for Ring-Closing Metathesis in Medicinal Chemistry: Mimicking Secondary Architectures in Bioactive Peptides Med. Res. Rev. 2010, 31 (5), 677-715.
Pen-Wei Hsieh et al., Curr. Pharm. Des., 2009,15(19): 2236-2250.
Petrie, K. A.; Bubser, M.; Casey, C. D.; Davis, M. D.; Roth, B. L.; Deutch, A. Y. The Neurotensin Agonist PD149163 Increases Fos Expression in the Prefrontal Cortex of the Rat. Neuropsychopharmacology 2004, 29 (10), 1878-1888.
Pettersen, E. F.; Goddard, T. D.; Huang, C. C.; Couch, G. S.; Greenblatt, D. M.; Meng, E. C.; Ferrin, T. E. UCSF Chimera—A Visualization System for Exploratory Research and Analysis. J. Comput. Chem. 2004, 25 (13), 1605-1612.
Rioux, F.; Quirion, R.; St-Pierre, S.; Regoli, D.; Jolicoeur, F. B.; Bélanger, F.; Barbeau, A. The Hypotensive Effect of Centrally Administered Neurotensin in Rats. Eur. J. Pharmacol. 1981, 69 (3), 241-247.
Roussy, G.; Dansereau, M.-A.; Doré-Savard, L.; Belleville, K.; Beaudet, N.; Richelson, E.; Sarret, P. Spinal NTS1 Receptors Regulate Nociceptive Signaling in a Rat Formalin Tonic Pain Model. J. Neurochem. 2008, 105 (4), 1100-1114.
Roussy, G.; Dansereau, M.-A.; Baudisson, S.; Ezzoubaa, F.; Belleville, K.; Beaudet, N.; Martinez, J.; Richelson, E.; Sarret, P. Evidence for a Role of NTS2 Receptors in the Modulation of Tonic Pain Sensitivity. Mol. Pain 2009, 5, 38-52.
Sharpe, A. L.; Varela, E.; Beckstead, M. J. Systemic PD149163, a Neurotensin Receptor 1 Agonist, Decreases Methamphetamine Self-Administration in DBA/2J Mice without Causing Excessive Sedation. PLoS One 2017, 12 (7), e0180710.
Smith, K. E.; Boules, M.; Williams, K.; Richelson, E. NTS1 and NTS2 Mediate Analgesia Following Neurotensin Analog Treatment in a Mouse Model for Visceral Pain. Behav. Brain Res. 2012, 232 (1), 93-97.
Sousbie, M.; Besserer-Offroy, É.; Brouillette, R. L.; Longpré, J.-M.; Leduc, R.; Sarret, P.; Marsault, É. In Search of the Optimal Macrocyclization Site for Neurotensin. ACS Med. Chem. Lett. 2018, 9 (3), 227-232.
Tétreault, P.; Beaudet, N.; Perron, A.; Belleville, K.; René, A.; Cavelier, F.; Martinez, J.; Stroh, T.; Jacobi, A. M.; Rose, S. D.; et al. Spinal NTS2 Receptor Activation Reverses Signs of Neuropathic Pain. FASEB J. 2013, 27 (9), 3741-3752.
Tjolsen, A.; Berge, O. G.; Hunskaar, S.; Rosland, J. H.; Hole, K. The Formalin Test: An Evaluation of the Method. Pain 1992, 51 (1), 5-17.
Trang, T.; Al-Hasani, R.; Salvemini, D.; Salter, M. W.; Gutstein, H.; Cahill, C. M. Pain and Poppies: The Good, the Bad, and the Ugly of Opioid Analgesics. J. Neurosci. 2015, 35 (41), 13879-13888.
Tyler, B. M.; Douglas, C. L.; Fauq, A; Pang, Y. P.; Stewart, J. A; Cusack, B.; McCormick, D. J.; Richelson, E. In Vitro Binding and CNS Effects of Novel Neurotensin Agonists That Cross the Blood-Brain Barrier. Neuropharmacology 1999, 38 (7), 1027-1034.
Van Kemmel, F. M.; Dubuc, I.; Bourdel, E.; Fehrentz, J. a; Martinez, J.; Costentin, J. A C-Terminal Cyclic 8-13 Neurotensin Fragment Analog Appears Less Exposed to Neprilysin When It Crosses the Blood-Brain Barrier than the Cerebrospinal Fluid-Brain Barrier in Mice. Neurosci. Lett. 1996, 217 (1), 58-60.
Van Tonder E.C., Mahlatji M.D., Malan S.F., Liebenberg W., Caira M.R., Song M., and de Villiers M.M. 2004. Preparation and Physicochemical Characterization of 5 Niclosamide Solvates and 1 Hemisolvate AAPS PharmSciTech. 5 (1): p. 1-10.
Vincent, B.; Jiracek, J.; Noble, F.; Loog, M.; Roques, B.; Dive, V.; Vincent, J. P.; Checler, F. Contribution of endopeptidase 3.4.24.15 to central neurotensin inactivation. Eur. J. Pharmacol. 1997, 334: 49-53.
Vincent, J. P.; Mazella, J.; Kitabgi, P. Neurotensin and Neurotensin Receptors. Trends Pharmacol. Sci. 1999, 20 (7), 302-309.
White, J. F.; Noinaj, N.; Shibata, Y.; Love, J.; Kloss, B.; Xu, F.; Gvozdenovic-Jeremic, J.; Shah, P.; Shiloach, J.; Tate, C. G.; et al. Structure of the Agonist-Bound Neurotensin Receptor. Nature 2012, 490 (7421), 508-513.
Wustrow, D. J.; Davis, M. D.; Akunne, H. C.; Corbin, A. E.; Wiley, J. N.; Wise, L. D.; Heffner, T. G. Reduced Amide Bond Neurotensin 8-13 Mimetics with Potent in Vivo Activity. Bioorg. Med. Chem. Lett. 1995, 5 (9), 997-1002.
Yudin, A. K. Macrocycles: Lessons from the Distant Past, Recent Developments, and Future Directions. Chem. Sci. 2015, 6 (1), 30-49.
Rautio et al., Nat. Rev. Drug Discov., (2008) 7: 255-270).

* cited by examiner

```
                           SEQUENCE LISTING

<160> NUMBER OF SEQ ID NOS: 35

<210> SEQ ID NO 1
<211> LENGTH: 6
<212> TYPE: PRT
<213> ORGANISM: homo sapiens

<400> SEQUENCE: 1

Arg Arg Pro Tyr Ile Leu
1               5

<210> SEQ ID NO 2
<211> LENGTH: 13
<212> TYPE: PRT
<213> ORGANISM: homo sapiens

<400> SEQUENCE: 2

Glu Leu Tyr Glu Asn Lys Pro Arg Arg Pro Tyr Ile Leu
1               5                   10

<210> SEQ ID NO 3
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: Xaa can be any naturally occurring or synthetic
      amino acid or acid

<400> SEQUENCE: 3

Xaa Xaa Xaa Xaa Xaa Xaa
1               5

<210> SEQ ID NO 4
<211> LENGTH: 5
<212> TYPE: PRT
<213> ORGANISM: artificial sequence
<220> FEATURE:
<223> OTHER INFORMATION: Synthetic construct

<400> SEQUENCE: 4

Lys Pro Tyr Ile Leu
1               5

<210> SEQ ID NO 5
<211> LENGTH: 5
<212> TYPE: PRT
<213> ORGANISM: artificial sequence
<220> FEATURE:
<223> OTHER INFORMATION: Synthetic construct

<400> SEQUENCE: 5

Arg Pro Tyr Ile Leu
1               5

<210> SEQ ID NO 6
<211> LENGTH: 5
<212> TYPE: PRT
<213> ORGANISM: artificial sequence
```

```
<220> FEATURE:
<223> OTHER INFORMATION: Synthetic construct

<400> SEQUENCE: 6

His Pro Tyr Ile Leu
1               5

<210> SEQ ID NO 7
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring or synthetic
      amino acid, aliphatic residue, alkenyl residue, or acid residue

<400> SEQUENCE: 7

Xaa Lys Pro Tyr Ile Leu
1               5

<210> SEQ ID NO 8
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring or synthetic
      amino acid, aliphatic residue, alkenyl residue, or acid residue

<400> SEQUENCE: 8

Xaa Arg Pro Tyr Ile Leu
1               5

<210> SEQ ID NO 9
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring or synthetic
      amino acid, aliphatic residue, alkenyl residue, or acid residue

<400> SEQUENCE: 9

Xaa His Pro Tyr Ile Leu
1               5

<210> SEQ ID NO 10
<211> LENGTH: 4
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring or synthetic
      amino acid, aliphatic residue, alkenyl residue, or acid residue

<400> SEQUENCE: 10

Xaa Lys Pro Tyr
1
```

```
<210> SEQ ID NO 11
<211> LENGTH: 4
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring or synthetic
      amino acid, aliphatic residue, alkenyl residue, or acid residue

<400> SEQUENCE: 11

Xaa Arg Pro Tyr
1

<210> SEQ ID NO 12
<211> LENGTH: 4
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring or synthetic
      amino acid, aliphatic residue, alkenyl residue, or acid residue

<400> SEQUENCE: 12

Xaa His Pro Tyr
1

<210> SEQ ID NO 13
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is lysine (alkenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 13

Xaa Lys Pro Xaa Ile Leu
1               5

<210> SEQ ID NO 14
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is lysine (allyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 14

Xaa Lys Pro Xaa Ile Leu
1               5
```

```
<210> SEQ ID NO 15
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is lysine (butenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 15

Xaa Lys Pro Xaa Ile Leu
1               5

<210> SEQ ID NO 16
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is lysine (pentenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 16

Xaa Lys Pro Xaa Ile Leu
1               5

<210> SEQ ID NO 17
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is ornithine (alkenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 17

Xaa Lys Pro Xaa Ile Leu
1               5

<210> SEQ ID NO 18
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is ornithine (allyl)
<220> FEATURE:
<221> NAME/KEY: misc_feature
<222> LOCATION: (4)..(4)
<223> OTHER INFORMATION: Xaa is tyrosine (allyl)
```

```
<400> SEQUENCE: 18

Xaa Lys Pro Xaa Ile Leu
1               5

<210> SEQ ID NO 19
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is ornithine (alkenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 19

Xaa His Pro Xaa Ile Leu
1               5

<210> SEQ ID NO 20
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is ornithine (allyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 20

Xaa His Pro Xaa Ile Leu
1               5

<210> SEQ ID NO 21
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Dab (alkenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 21

Xaa Lys Pro Xaa Ile Leu
1               5

<210> SEQ ID NO 22
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Dab (allyl)
```

-continued

```
<220> FEATURE:
<221> NAME/KEY: misc_feature
<222> LOCATION: (4)..(4)
<223> OTHER INFORMATION: Xaa is tyrosine (allyl)

<400> SEQUENCE: 22

Xaa Lys Pro Xaa Ile Leu
1               5

<210> SEQ ID NO 23
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Dab (butenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 23

Xaa Lys Pro Xaa Ile Leu
1               5

<210> SEQ ID NO 24
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Dap (alkenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 24

Xaa Lys Pro Xaa Ile Leu
1               5

<210> SEQ ID NO 25
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Dap (pentenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 25

Xaa Lys Pro Xaa Ile Leu
1               5

<210> SEQ ID NO 26
<211> LENGTH: 6
<212> TYPE: PRT
<213> ORGANISM: artificial sequence
<220> FEATURE:
```

```
<223> OTHER INFORMATION: Synthetic construct
<220> FEATURE:
<221> NAME/KEY: misc_feature
<222> LOCATION: (1)..(1)
<223> OTHER INFORMATION: Xaa is alkenyl acid
<220> FEATURE:
<221> NAME/KEY: misc_feature
<222> LOCATION: (4)..(4)
<223> OTHER INFORMATION: Xaa is tyrosine (allyl)

<400> SEQUENCE: 26

Xaa Lys Pro Xaa Ile Leu
1               5

<210> SEQ ID NO 27
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is nonenoic acid
<220> FEATURE:
<221> NAME/KEY: misc_feature
<222> LOCATION: (4)..(4)
<223> OTHER INFORMATION: Xaa is tyrosine (allyl)

<400> SEQUENCE: 27

Xaa Lys Pro Xaa Ile Leu
1               5

<210> SEQ ID NO 28
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Aminohex-6-enoic acid
<220> FEATURE:
<221> NAME/KEY: misc_feature
<222> LOCATION: (4)..(4)
<223> OTHER INFORMATION: Xaa is tyrosine (allyl)

<400> SEQUENCE: 28

Xaa Lys Pro Xaa Ile Leu
1               5

<210> SEQ ID NO 29
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Aminohex-6-enoic acid allyl
<220> FEATURE:
<221> NAME/KEY: misc_feature
<222> LOCATION: (4)..(4)
<223> OTHER INFORMATION: Xaa is tyrosine (allyl)

<400> SEQUENCE: 29

Xaa Lys Pro Xaa Ile Leu
1               5
```

```
<210> SEQ ID NO 30
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is alkenyl acid
<220> FEATURE:
<221> NAME/KEY: misc_feature
<222> LOCATION: (4)..(4)
<223> OTHER INFORMATION: Xaa is tyrosine (allyl)

<400> SEQUENCE: 30

Xaa Arg Pro Xaa Ile Leu
1               5

<210> SEQ ID NO 31
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is nonenoic acid
<220> FEATURE:
<221> NAME/KEY: misc_feature
<222> LOCATION: (4)..(4)
<223> OTHER INFORMATION: Xaa is tyrosine (allyl)

<400> SEQUENCE: 31

Xaa Arg Pro Xaa Ile Leu
1               5

<210> SEQ ID NO 32
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is alkenylalanine
<220> FEATURE:
<221> NAME/KEY: misc_feature
<222> LOCATION: (4)..(4)
<223> OTHER INFORMATION: Xaa is tyrosine (allyl)

<400> SEQUENCE: 32

Xaa Lys Pro Xaa Ile Leu
1               5

<210> SEQ ID NO 33
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is octenylalanine
<220> FEATURE:
<221> NAME/KEY: misc_feature
<222> LOCATION: (4)..(4)
<223> OTHER INFORMATION: Xaa is tyrosine (allyl)

<400> SEQUENCE: 33
```

```
Xaa Lys Pro Xaa Ile Leu
1               5

<210> SEQ ID NO 34
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is lysine S(O)2(o-nitrophenyl)
<220> FEATURE:
<221> NAME/KEY: misc_feature
<222> LOCATION: (4)..(4)
<223> OTHER INFORMATION: Xaa is tyrosine (allyl)

<400> SEQUENCE: 34

Xaa Lys Pro Xaa Ile Leu
1               5

<210> SEQ ID NO 35
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is lysine-CH2-NH
<220> FEATURE:
<221> NAME/KEY: misc_feature
<222> LOCATION: (6)..(6)
<223> OTHER INFORMATION: Xaa is tert leucine

<400> SEQUENCE: 35

His Xaa Lys Pro Trp Xaa Leu
1               5
```

MACROCYCLIC COMPOUNDS AND METHODS OF PREVENTING OR TREATING PAIN

CROSS REFERENCE TO RELATED APPLICATIONS

This application claims benefit, under 35 U.S.C. § 119(e), of U.S. provisional application Ser. No. 62/520,980, filed on Jun. 16, 2017. All documents above are incorporated herein in their entirety by reference.

STATEMENT REGARDING FEDERALLY SPONSORED RESEARCH OR DEVELOPMENT

N.A.

FIELD OF THE INVENTION

The present invention relates to macrocyclic compounds and methods of preventing or treating pain. More specifically, the present invention is concerned with macrocyclic compounds derived from neurotensin and methods of using same.

REFERENCE TO SEQUENCE LISTING

Pursuant to 37 C.F.R. 1.821(c), a sequence listing is submitted herewith as an ASCII compliant text file named sequence listing_ST25, that was created on Jun. 18, 2018 and having a size of 11 kilobytes. The content of the aforementioned file named sequence listing_ST25 is hereby incorporated by reference in its entirety.

BACKGROUND OF THE INVENTION

Pain is the most common reason for physician consultation in most developed countries. It is a major symptom in many medical conditions, and can interfere with a person's quality of life and general functioning. It also creates a significant burden on society and is one of the primary reasons for absenteeism at work. Acute pain, e.g., related to injury, surgery or disease, can be severe and has significant impact on patient recovery, while chronic pain, which affects around 20% of the population, can also cause isolation, symptoms of anxiety and is frequently accompanied by depression, which can include changes in mood, appetite and sleep, thus preventing a sufferer from typical daily activities. Acute pain is usually managed effectively with pharmacological treatments, notably with the first line agents acetaminophen and nonsteroidal anti-inflammatory drugs (NSAID). Severe acute pain is typically treated with potent opioids. Management of chronic pain, however, is much more difficult. Pain medications are only effective in 20% to 70% of cases.

Drugs currently used to treat pain are not always effective (anti-inflammatory) or exhibit severe adverse effects such as development of constipation, nausea/vomiting, respiratory depression and tolerance/dependence (opioids such as morphine) in patients. Opioids are very commonly used, despite their undesirable effects, because they are very effective to alleviate pain. Opioids work by activating the Mu opioid receptor in the central nervous system. However, it is also the activation of this opioid receptor which causes undesirable effects. To date, almost all drugs that activate this receptor have the same deleterious side effect, and opioid abuse resulting from tolerance and dependence is now a widespread problem in Western countries.

Neurotensin (NT) is a tridecapeptide, which was first isolated from bovine hypothalamus in 1973 (Carraway, 1973). It has been shown that activation of the NT receptors, which belong to the G protein-coupled receptors (GPCRs) superfamily, particularity the NTS1 and NTS2 receptors, results in an analgesic action similar to that obtained by activating the Mu opioid receptor but does not cause the same undesirable effects. Constipation and respiratory depression peculiar to the Mu opioid receptor are not observed subsequent to activation of the neurotensin receptors. Existing data also indicate that the analgesic effects of NT are independent of the endogenous opioid system, and may even act synergistically with opioids to reduce pain (Feng, 2015; Dobner, 2012). A pain medication that would go through the activation of the NT receptors rather than the opioid receptor would therefore solve the main problem of the drugs currently in use.

In addition to analgesia (Nemeroff, 1979), NT exerts a wide range of physiological effects such as hypothermia (Dubuc, 1992). Targeted temperature management (TTM) (mild therapeutic hypothermia) is an active treatment seeking to achieve and maintain a specific body temperature in a person for a specific duration of time in an effort to improve health outcomes during recovery after a period of stopped blood flow to the brain (Peberdy, 2010). This is done to reduce the risk of tissue injury following a lack of blood flow (Bernard, 2002). Periods of poor blood flow may be due to myocardial infarction (heart attack), or to the blockage of an artery by a clot as in the case of a stroke or traumatic brain injury. TTM can significantly improve rates of long-term neurologically intact survival.

NT's half-life is however very short because of enzymatic degradation by amino- and carboxypeptidases, especially specific endopeptidases [24-11] (Connelly, 1985), [24-15] (Vincent, 1997), and [24-16] (Barelli, 1993).

There is a need for compounds displaying advantageous characteristics of NT i.e. potency and reduced adverse effects, but having a better half-life than NT.

The present description refers to a number of documents, the content of which is herein incorporated by reference in their entirety.

SUMMARY OF THE INVENTION

More specifically, in accordance with the present invention, the following items are provided:
1. A compound of formula (I)

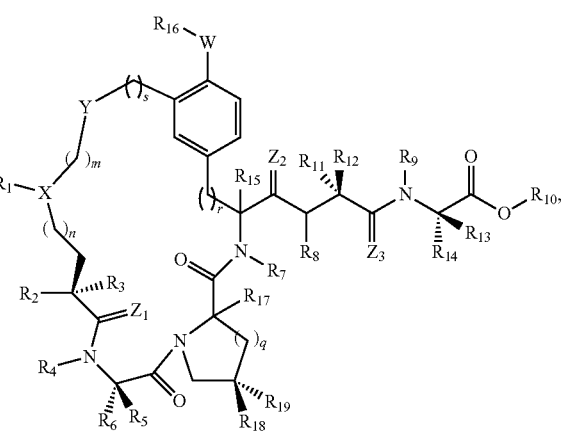

(I)

wherein:
(i) X is —CH and R1=H; or
X is N and R1 is H, (C1-12)alkyl, (C4-C14)aralkyl, SO$_2$(C3-C7) aryl, —SO$_2$(C1-12)alkyl, —SO$_2$aralkyl, —CO(C1-12)alkyl, CO(C4-C14)aralkyl, or —C(=NH)NH$_2$;
(ii) R2 is H or —CH$_3$; and R3 is H, —NH$_2$, —NHalkyl, NHaralkyl, —NHCOalkyl, —NHSO$_2$aryl, or —NH(C=NH)NH$_2$; or
R2 is H, —NH$_2$, —NHalkyl, NHaralkyl, —NHCOalkyl, —NHSO$_2$aryl, or —NH(C=NH)NH$_2$; and R3 is H or —CH$_3$;
(iii) R4, R7, R8 and R9 are each independently H, (C1-12)alkyl, or (C4-C14)aralkyl;
(iv) R5 is H or —CH$_3$; and R6 is —(CH$_2$)pNHR20 or the side chain of histidine; or
R6 is H or —CH$_3$; and R5 is —(CH$_2$)pNHR20 or the side chain of histidine,
wherein p is 1-5; and R20 is H, —C(=NH)—NH$_2$, (C1-12)alkyl, or (C4-C12)aralkyl;
(v) R10 is H, benzyl, (C4-C14)aralkyl, or (C1-12)alkyl;
(vi) R11 is H or —CH$_3$; and R12 is —CH$_2$Si(CH$_3$)$_3$, or the side chain of a valine, alanine, glycine, leucine, isoleucine, allo-isoleucine, tert-butyl glycine, tert-butyl alanine, cyclohexylglycine, cyclopentylglycine, cyclobutylglycine, cyclopropylglycine, norvaline or norleucine; or
R12 is H or —CH$_3$; and R11 is —CH$_2$Si(CH$_3$)$_3$, or the side chain of a valine, alanine, glycine, leucine, isoleucine, allo-isoleucine, tert-butyl glycine, tert-butyl alanine, cyclohexylglycine, cyclopentylglycine, cyclobutylglycine, cyclopropylglycine, norvaline or norleucine;
(vii) R13 is H or —CH$_3$; and R14 is the side chain of a valine, alanine, glycine, leucine, isoleucine, allo-isoleucine, tert-butyl glycine, tert-butyl alanine, cyclohexylalanine, cyclopentylalanine, cyclobutylalanine, cyclopropylalanine, norvaline or norleucine; or
R14 is H or —CH$_3$; and R13 is the side chain of a valine, alanine, glycine, leucine, isoleucine, allo-isoleucine, tert-butyl glycine, tert-butyl alanine, cyclohexylalanine, cyclopentylalanine, cyclobutylalanine, cyclopropylalanine, norvaline or norleucine;
(viii) R15 is H or —CH$_3$;
(ix) R16 is H, (C1-C12)alkyl, (C4-C14)aralkyl, or C(=O)R21, wherein R21 is (C1-C12)alkyl or (C4-C14)aralkyl;
(x) R17 is H or —CH$_3$;
(xi) R18 is H or —CH$_3$; and R19 is H, —OH, (C1-C10)alkyl, —(C1-C10)Oalkyl or —(C1-C10)NHalkyl; or
R19 is H or —CH$_3$; and R18 is H, —OH, (C1-C10)alkyl, —(C1-C10)Oalkyl or —(C1-C10)NHalkyl;
(xii) m is 1-4;
(xiii) n is 0-4;
(xiv) q is 0-3;
(xv) r is 0-3;
(xvi) s is 0-3;
(xvii) Y is —CH=CH— (E or Z), —CH$_2$—CH$_2$—, or —C≡C—;
(xviii) W is O, —NH or S; and
(xix) Z$_1$, Z$_2$ and Z$_3$ are each independently =O or absent, or an ester, solvate, hydrate or pharmaceutical salt thereof.

2. The compound of item 1, wherein:
(iv) R5 is H or —CH$_3$; and R6 is —(CH$_2$)pNHR20, wherein p and R20 are as defined in item 1, or is the side chain of histidine;
(vi) R11 is H or —CH$_3$; and R12 is —CH$_2$Si(CH$_3$)$_3$, or the side chain of a valine, alanine, glycine, leucine, isoleucine, allo-isoleucine, tert-butyl glycine, tert-butyl alanine, cyclohexylglycine, cyclopentylglycine, cyclobutylglycine, cyclopropylglycine, norvaline or norleucine;
(vii) R13 is H or —CH$_3$; and R14 is the side chain of a valine, alanine, glycine, leucine, isoleucine, allo-isoleucine, tert-butyl glycine, tert-butyl alanine, cyclohexylalanine, cyclopentylalanine, cyclobutylalanine, cyclopropylalanine, norvaline or norleucine;
(viii) R15 is (S)—H (S) or (S)—CH$_3$; and
(x) R17 is (S)—H (S) or (S)—CH$_3$.

3. The compound of item 1 or 2, wherein R12 is the side chain of a leucine, isoleucine, allo-isoleucine, tert-butyl glycine, tert-butyl alanine, cyclohexylglycine, cyclopentylglycine, cyclobutylglycine, cyclopropylglycine, norvaline or norleucine.

4. The compound of any one of items 1 to 3, wherein R13 is the side chain of a leucine, isoleucine, allo-isoleucine, tert-butyl glycine, tert-butyl alanine, cyclohexylalanine, cyclopentylalanine, cyclobutylalanine, cyclopropylalanine, norvaline or norleucine.

5. The compound of any one of items 1 to 4, wherein:
(iii) R4, R7, R8 and R9 are each H;
(iv) R5 is H; and R6 is —(CH$_2$)pNHR20 or R6 is the side chain of histidine;
wherein p is 3 or 4; and R20 is H or —C(=NH)—NH$_2$;
(vi) R11 is H; and R12 is the side chain of an isoleucine;
(vii) R13 is H; and R14 is the side chain of a leucine;
(viii) R15 is H;
(x) R17 is H;
(xi) R18 and R19 are each H;
(xiv) q is 1;
(xv) r is 1;
(xvi) s is 1;
(xvii) Y is —CH=CH—;
(xviii) W is O; and/or
(xix) Z$_1$, Z$_2$ and Z$_3$ are each =O,
or an ester, solvate, hydrate or pharmaceutical salt thereof.

6. The compound of any one of items 1 to 4, wherein:
(iv) R5 is H; and R6 is —(CH$_2$)pNHR20; wherein p is 4; and R20 is H.

7. The compound of any one of items 1 to 4, wherein:
(iv) R5 is H; and R6 is —(CH$_2$)pNHR20; wherein p is 3; and R20 is —C(=NH)—NH$_2$.

8. The compound of item 1, wherein:
(iv) R5 is H; and R6 is is the side chain of a histidine 9. The composition of item 1, wherein the compound is of formula (Ia)

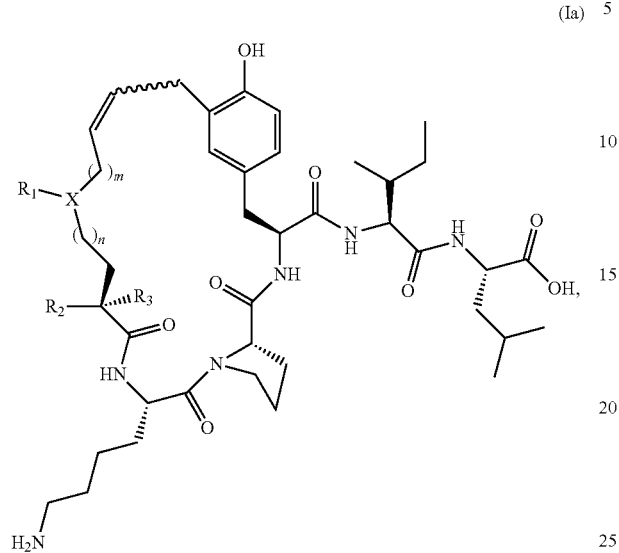

(Ia)

wherein X, R1, R2, R3, n and m are as defined in item 1, or an ester, solvate, hydrate or pharmaceutical salt thereof.

10. The compound of any one of items 1 to 9, wherein X is N and R1 is H, (C1-12)alkyl, (C4-C14)aralkyl, —SO₂(C3-C7)aryl, —SO₂(C1-12)alkyl, —SO₂aralkyl, —CO(C1-12)alkyl, CO(C4-C14)aralkyl, or —C(=NH)NH₂.

11. The compound of any one of items 1 to 10, wherein R1 is H.

12. The compound of any one of items 1 to 10, wherein R1 is S(=O)₂(o-nitrophenyl).

13. The compound of any one of items 1 to 9, wherein X is CH and R1 is H.

14. The compound of item 13, wherein n+m=3

15. The compound of any one of items 1 to 14, wherein n is 1-3.

16. The compound of any one of items 1 to 14, wherein n is 0.

17. The compound of any one of items 1 to 14, wherein n is 1.

18. The compound of any one of items 1 to 14, wherein n is 2.

19. The compound of any one of items 1 to 149, wherein n is 3.

20. The compound of any one of items 1 to 19, wherein m is 1-3.

21. The compound of any one of items 1 to 19, wherein m is 1.

22. The compound of any one of items 1 to 19, wherein m is 2.

23. The compound of any one of items 1 to 19, wherein m is 3.

24. The compound of any one of items 1 to 23, wherein R2 is H; and/or
R3 is H or CH₃.

25. The compound of any one of items 1 to 23, wherein R2 is —NH₂; and/or
R3 is H or CH₃.

26. The compound of any one of items 1 to 23, wherein R2 is —NH2 and R3 is H.

27. The compound of any one of items 1 to 23, wherein R2 and R3 are H.

28. The compound of item 1, wherein the compound is:

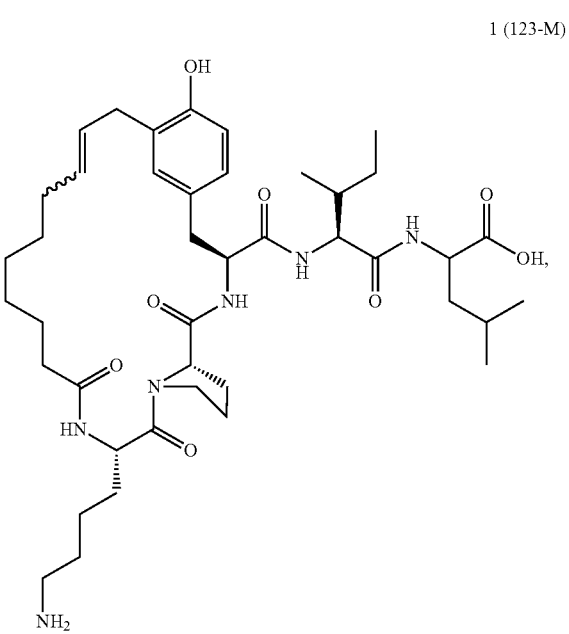

1 (123-M)

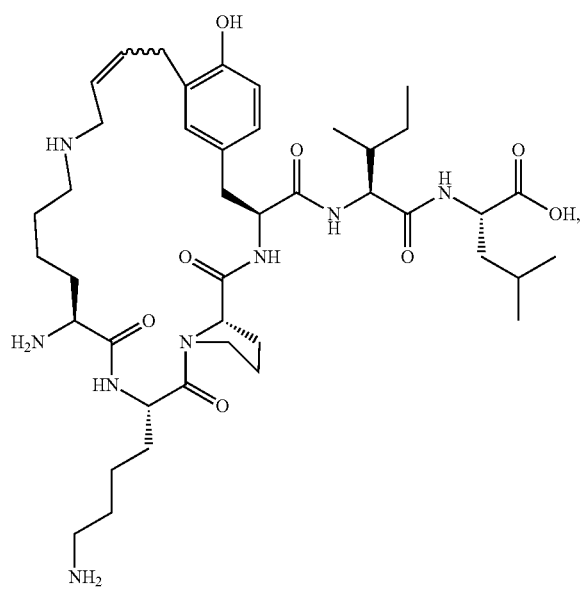

2 (5-116)

3 (05-142)
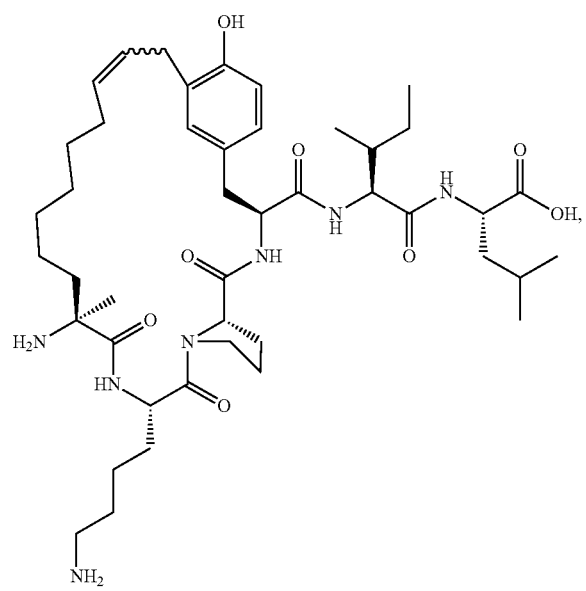
5 (05-139)
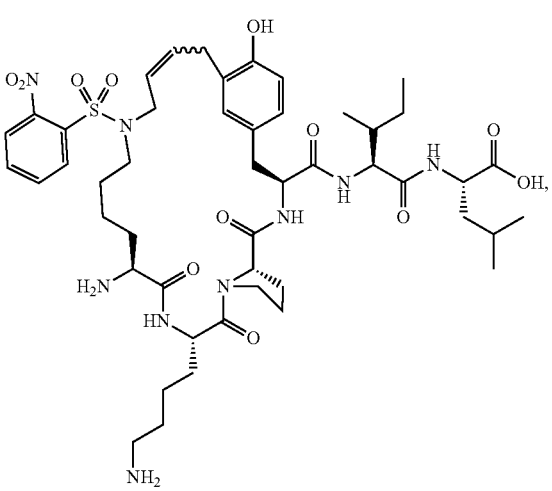
4 (05-141)
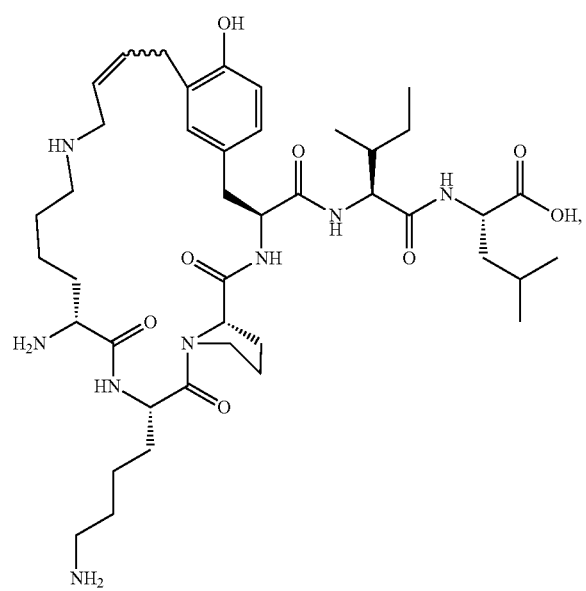
6 (05-138)
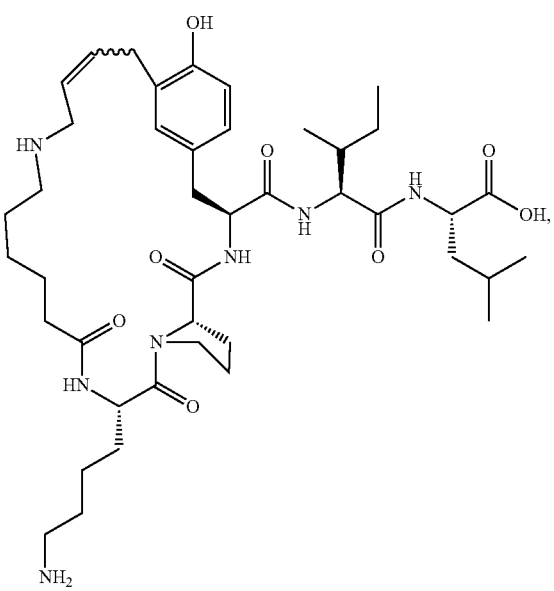

7 (05-153)
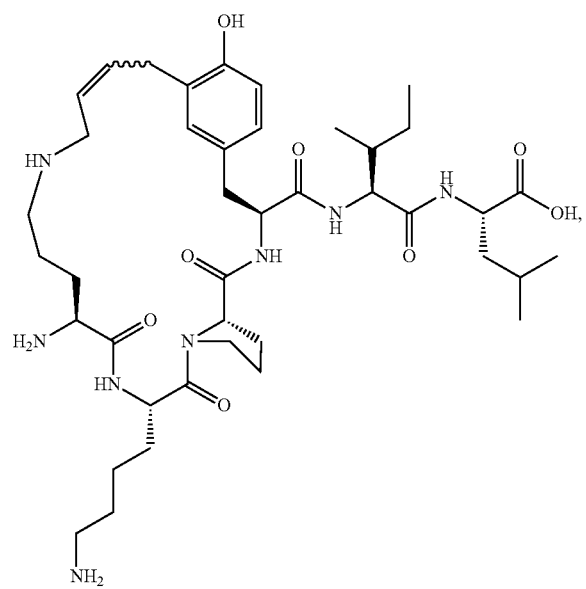
8 (05-154)
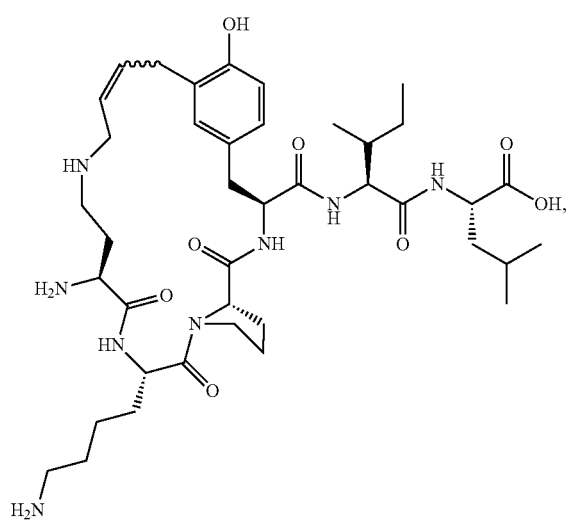
9 (05-163)
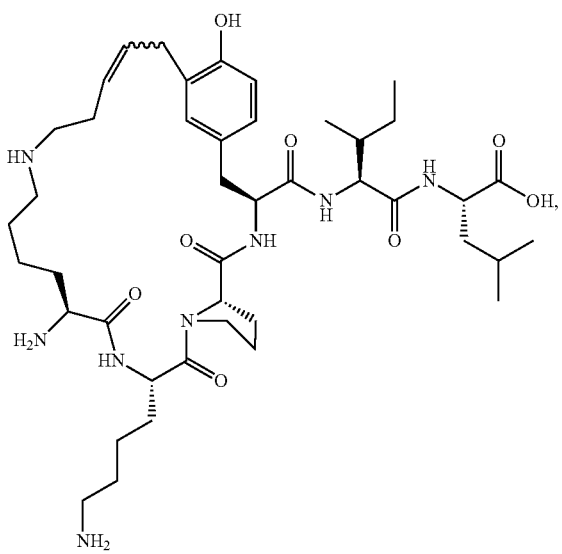
10 (05-164)
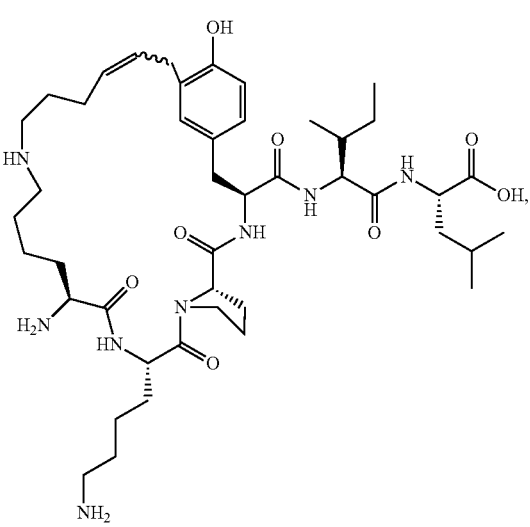

11 (05-122)
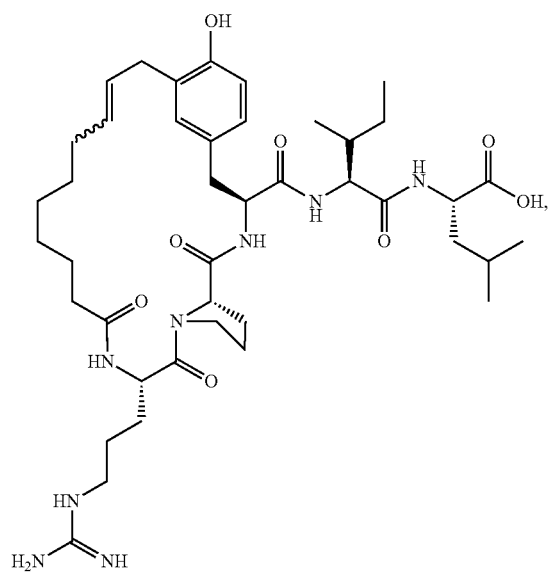
13 (01-07)
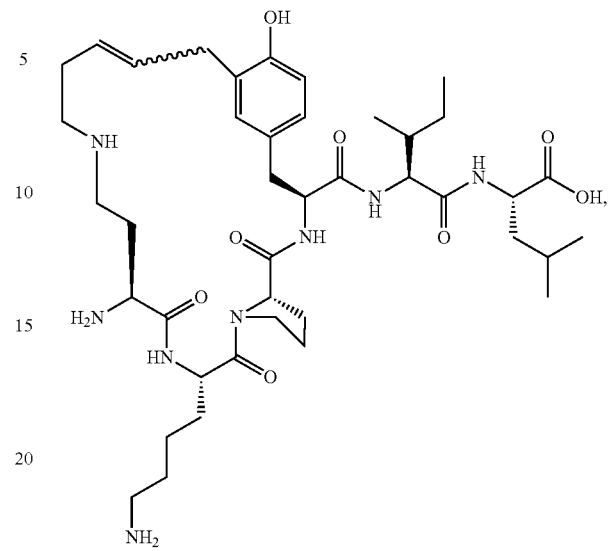
14 (01-08)
12 (01-65)
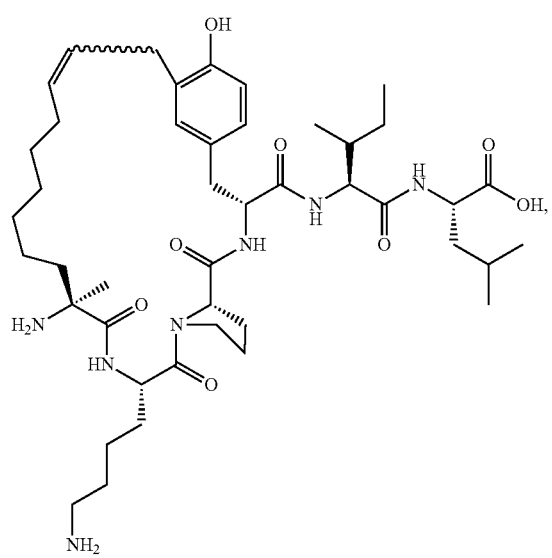
15 (01-13)
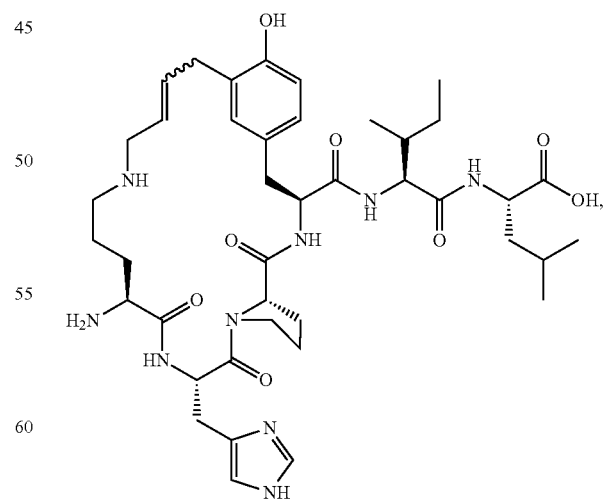
or an ester, solvate, hydrate or pharmaceutical salt thereof.
29. A composition comprising (a) the compound defined in any one of items 1 to 28, and (b) (i) at least another compound defined in any one of items 1 to 28; (ii) another antalgic agent; (iii) an anxiolytic agent; (iv) an antidepressant agent; (v) a pharmaceutically acceptable carrier; or (vi) a combination of at least two of (i) and (v).

30. A method of preventing or treating pain comprising administering to a subject in need thereof an effective amount of the compound defined in any one of items 1 to 28, or the composition defined in item 29.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 6A: Compound 2 compared to its linear counterpart and to NT 8-13. FIG. 6B: Comparison of compound 7 with compound 3.

FIG. 8A: Dose-response curve of compound 7 in the acute thermal tail-flick test. Tail-flick latencies were measured each 10 min for up to 60 min following i.t. injection of 7 at different doses. FIG. 8B: Calculation of area under the curve (AUC) for each dose allowed to determinate the half maximal effective dose ($ED_{50}$) of macrocycle 7 to induce analgesia in acute pain. FIG. 8C: Antinociceptive effect of compounds 3, 7 and PD149163 (30 μg/kg) in acute pain.

FIG. 8D: Percentage of Maximal Possible Effect (% MPE) was calculated at 10 min post-injection, when the antinociceptive response was maximal. FIGS. 8E-F: Antinociceptive effects of compounds 3, 7 and PD149163 (30 μg/kg) were evaluated in the formalin-induced tonic pain assay. FIG. 8E: Time course of analgesic effects of compounds in acute and inflammatory phases. FIG. 8F: To statistically determine the analgesic effect of each compound, AUC (au=arbitrary unit) was calculated over a time span of 60 min. n=3-8 rats (tail-flick test) and n=4-7 rats (formalin test) for each compound. Error bars represent mean±SEM. A two-way ANOVA followed by Tukey's correction (FIGS. 8A and C) and a one-way ANOVA followed by Dunnett's correction (FIGS. 8D and F) were performed. *p<0.05; p<0.01; *p<0.001; as compared to saline-injected rats.

FIG. 8A: Dose-response curve of 7 on body temperature. Change of body temperature (Δ Body Temp) was calculated every 10 min for up to 60 min following i.t. injection of compound 7 at different concentrations. FIG. 8B: Calculation of AUC for each concentration leading to the determination of the ED50 of compound 7 to induce hypothermia. FIG. 8C: Hypothermic effect of compounds 3, 7 and PD149163, 1 h after their i.t. administration at 30 μg/kg. A two-way ANOVA followed by Tukey's correction (FIG. 8A) was performed. *p<0.05; p<0.01; *p<0.001; as compared to saline-injected rats.

DESCRIPTION OF ILLUSTRATIVE EMBODIMENTS

Figure 1:
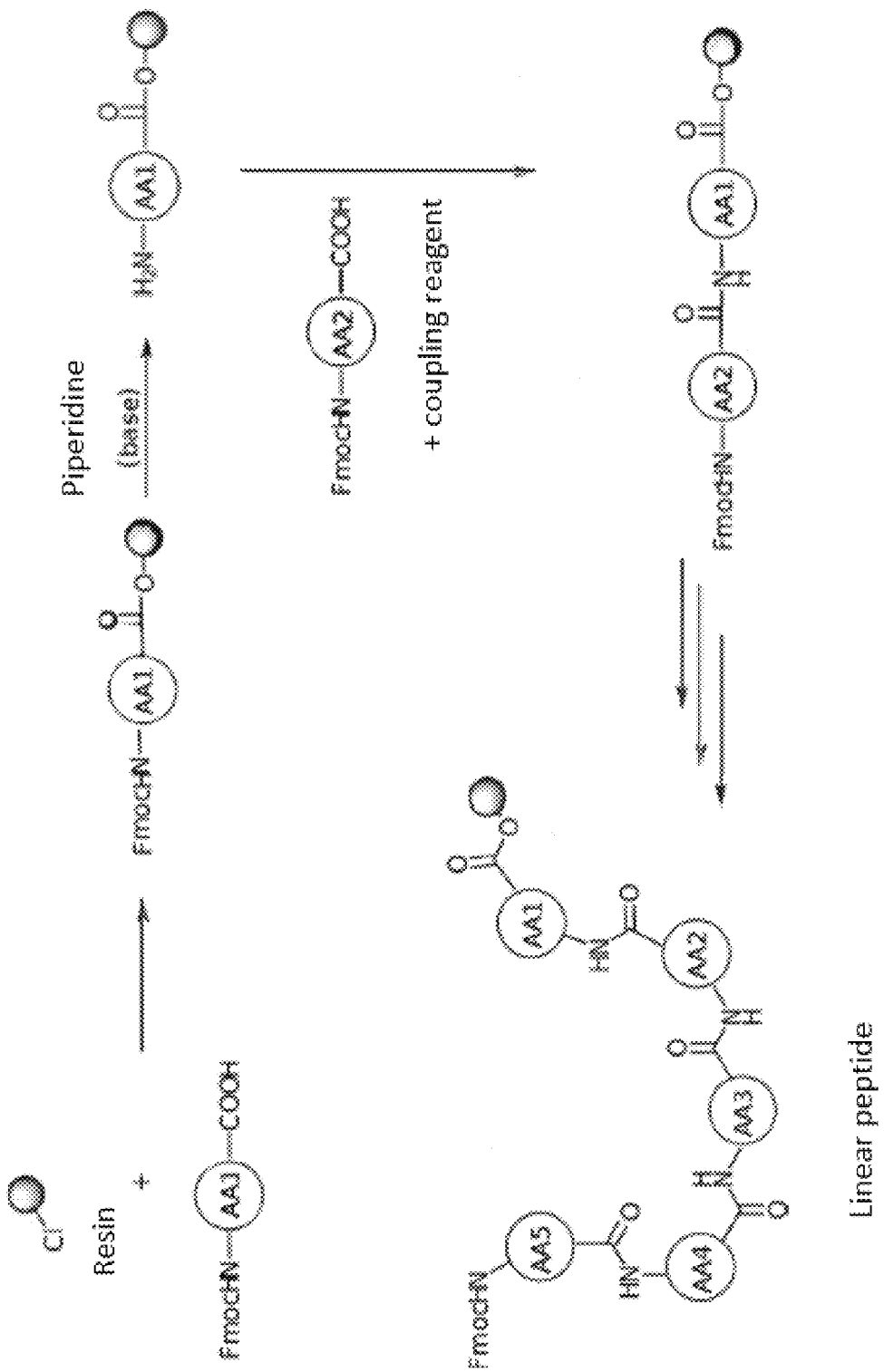
FIG. 1: Schematic peptide synthesis on solid support.

The present invention relates to macrocyclic compounds that are agonists of the neurotensin 1 (NTS1) and neurotensin 2 (NTS2) receptors. It also relates to method of using these compounds or compositions comprising these compounds to prevent or treat pain (e.g., acute or chronic pain); and/or to reduce body temperature in a subject.

Compounds of the Present Invention

In specific embodiments, macrocyclic compounds of the present invention are developed from the cyclization of a synthetic peptide (generally made from natural and/or non-natural amino acids) derived from the 8-13 fragment (RRPYIL) (SEQ ID NO: 1) of the neurotensin peptide (E-L-Y-E-N-K-P-R-R-P-Y-I-L) (SEQ ID NO: 2).

In specific embodiments, the cyclisation of the peptide is a side chain to side chain cyclisation. In specific embodiments, the cyclisation of the synthetic peptide is achieved through a reaction of metathesis of alkene (or alkyne) groups at the end of each of the side chains of the N- and C-terminal synthetic amino acids (or acid) moieties, the cyclisation resulting in a single carbon-carbon double bond (or single carbon-carbon triple bond if alkyne groups are used). The macrocycle may further be modified to replace the double bond by a single bond through palladium-catalyzed hydrogenation.

In a specific embodiment, compounds of the present invention are of formula (I) or (Ia), or are esters, solvates, hydrates or pharmaceutical salts thereof. In case of discrepancies herein between the name and structure presented of compounds or parts thereof, the structure shall prevail.

References herein to amino acids or acids that are part of molecules of the present invention should be understood to designate amino acid residues. At least one of their ends is linked to another amino acid or acid to form e.g., a peptide bond thereby losing an hydroxy group and/or one hydrogen of an amine group. Hence, for example, an amino acid or acid listed in any one of the definitions of Xaa1, Xaa2, Xaa3, Xaa4, Xaa5 and Xaa6 should be understood to be the corresponding amino acid or acid residue.

In another specific embodiment, the macrocyclic compound has the following structure: c[Xaa1-Xaa2-Xaa3-Xaa4]-Xaa5-Xaa6 (SEQ ID NO: 3), wherein:

Xaa1 is an aliphatic residue, alkenyl residue, an acid residue or an amino acid residue, Xaa2 is a glycine, alanine, diaminobutanoic acid, ornithine, lysine, arginine, histidine, diaminopropanoic acid, or diaminoheptanoic acid, this natural or non-natural amino acid or derivative thereof being optionally substituted;

Xaa3 is proline, or a derivative thereof, this amino acid or derivative thereof being optionally substituted;

Xaa4 is tyrosine, substituted at an ortho position of its phenol (to close the cycle with Xaa1), or a derivative thereof, this amino acid or derivative thereof being further optionally substituted;

Xaa5 is a valine, alanine, glycine, leucine, isoleucine, allo-isoleucine, tert-butyl glycine, tert-butyl alanine, cyclohexylglycine, cyclopentylglycine, cyclobutylglycine, cyclopropylglycine, norvaline or norleucine residue, or —NHCH(CH$_2$Si(CH$_3$)$_3$)C(=O)—, more preferably a leucine, isoleucine, allo-isoleucine, tert-butyl glycine, tert-butyl alanine, cyclohexylglycine, cyclopentylglycine, cyclobutylglycine, cyclopropylglycine, norvaline or norleucine residue or —NHCH(CH$_2$Si(CH$_3$)$_3$)C(=O)—, or a derivative thereof, this natural or non-natural amino acid or derivative thereof being optionally substituted;

Xaa6 is a valine, alanine, glycine, leucine, isoleucine, allo-isoleucine, tert-butyl glycine, tert-butyl alanine, cyclohexylalanine, cyclopentylalanine, cyclobutylalanine, cyclopropylalanine, norvaline or norleucine residue, or —NHCH(CH$_2$Si(CH$_3$)$_3$)C(=O)—, more preferably a leucine, isoleucine, allo-isoleucine, tert-butyl glycine, tert-butyl alanine, cyclohexylalanine, cyclopentylalanine, cyclobutylalanine, cyclopropylalanine, norvaline or norleucine residue or —NHCH(CH$_2$Si(CH$_3$)$_3$)C(=O)—, or a derivative thereof, this natural or non-natural amino acid or derivative thereof being optionally substituted; and wherein Xaa4 and Xaa1 are linked through their lateral chains.

In a specific embodiment, one of the end terminal non-natural amino acid residue used for closing the cycle (e.g., Xaa4) is, before ring-closure, an o-substituted alkenyl-tyrosine (e.g., o-allyl-tyrosine) (Xaa4) and the other end (e.g., Xaa1) is, before ring-closure, an alkenyl residue, an acid residue or a non-natural amino acid residue, this alkenyl, acid or amino acid residue comprising an alkene moiety at its end (end of its lateral chain in the case of an amino acid residue). After closure, the double bonds of each end terminal moiety have merged into a single carbon-carbon double bond using, for example, a ring-closing metathesis reaction.

In other specific embodiments, Xaa1 is, before ring-closure, an acid residue with an aliphatic tail of 4 to 11 carbon atoms comprising a terminal alkene (e.g., nonenoic acid residue (compounds 1 and 11)) or an acid residue with an amino alkyl chain substituted with a terminal alkene (e.g., aminohex-6-enoic acid residue (compound 6); a non-natural amino acid having an alkyl chain comprising a terminal alkene (e.g., an alpha-methyl-octenyl-alanine residue (compounds 3 and 12)) or a non-natural amino acid having an amino alkyl chain comprising a terminal alkene (e.g., an N-allyl ornithine residue (e.g., compounds 7 and 15), an N-allyl Dab (diaminobutyric acid) residue (e.g., compound 8), an N-butenyl Dab residue (e.g., compound 13), an N-pentenyl Dap (diaminopropionic acid) residue (e.g., compound 14), an N-ally-lysine residue (N-allyl-L-lysine, compounds 2 and 5; or N-allyl-D-lysine, compound 4), an N-butenyl-lysine residue (e.g., compound 9) or an N-pentenyl-lysine residue (e.g., compound 10). Xaa1 may further be substituted e.g., on the endocyclic amine (e.g., compound 5).

In specific embodiments, the compounds of the present invention comprise the sequence of amino acid residues K-P-Y-I-L (SEQ ID NO: 4) or R-P-Y-I-L (SEQ ID NO: 5) or H-P-Y-I-L (SEQ ID NO: 6), wherein the tyrosine is an o-allyl-tyrosine (o-allyl means ortho-allyl) residue. In other more specific embodiments, compounds of the present invention comprise the sequence of residues Xaa1-K-P-Y-I-L (SEQ ID NO: 7) or Xaa1-R-P-Y-I-L (SEQ ID NO: 8) or Xaa1-H-P-Y-I-L (SEQ ID NO: 9), wherein the tyrosine is an o-allyl-tyrosine residue and Xaa1 is as above defined. In a more specific embodiment, the ring portion of the compounds of the present invention comprise the residues Xaa1-K-P-Y (SEQ ID NO: 10), or Xaa1-R-P-Y (SEQ ID NO: 11) or Xaa1-H-P-Y (SEQ ID NO: 12), or a derivative thereof comprising one or more substituents (e.g., on amino acid residues), wherein Xaa1 is as above defined. In other specific embodiments, the compounds of the present invention comprise a c[Xaa1-K-P-Y] (SEQ ID NO: 10) ring or c[Xaa1-R-P-Y] (SEQ ID NO: 11) ring or c[Xaa1-H-P-Y] (SEQ ID NO: 12) ring, or a derivative thereof comprising one or more substituents. In other specific embodiments, the compounds of the present invention comprise c[K(alkenyl)-K-P-Y(allyl)]-I-L (SEQ ID NO: 13) (e.g., c[K(allyl)-K-P-Y(allyl)]-I-L (SEQ ID NO: 14), c[K(butenyl)-K-P-Y(allyl)]-I-L (SEQ ID NO: 15) or c[K(pentenyl)-K-P-Y(allyl)]-I-L) (SEQ ID NO: 16)); c[Orn(alkenyl)-K-P-Y(allyl)]-I-L (SEQ ID NO: 17) or c[Orn(alkenyl)-H-P-Y(allyl)]-I-L (SEQ ID NO: 19) (e.g., c[Orn(allyl)-K-P-Y(allyl)]-I-L (SEQ ID NO: 18) or c[Orn(All)HPY(All)]IL (SEQ ID NO: 20)); c[Dab(alkenyl)-K-P-Y(allyl)]-I-L (SEQ ID NO: 21) (e.g., c[Dab(All)KPY(All)]IL (SEQ ID NO: 22), c[Dab(butenyl)-K-P-Y(allyl)]-I-L) (SEQ ID NO: 23)); c[Dap(alkenyl)-K-P-Y(allyl)]-I-L (SEQ ID NO: 24) (e.g., c[Dap(pentenyl)-K-P-Y(allyl)]-I-L (SEQ ID NO: 25)); c[alkenyl acid-K-P-Y(allyl)]-I-L (SEQ ID NO: 26) or c[alkenyl acid-R-P-Y(allyl)]-I-L (SEQ ID NO: 30) (e.g., c[nonenoic acid KPY(allyl)]IL (SEQ ID NO: 27), c[nonenoic acid RPY(allyl)]IL (SEQ ID NO: 31), c[aminohex-6-enoic-K-P-Y(allyl)]-I-L) (SEQ ID NO: 28), c[aminohex-6-enoic (All)-K-P-Y(allyl)]-I-L) (SEQ ID NO: 29); c[alkenylA-K-P-Y(allyl)]-I-L (SEQ ID NO: 32) (e.g., c[octenylA-K-P-Y(allyl)]-I-L (SEQ ID NO: 33)), or a derivative of any of the foregoing comprising one or more substituents (e.g., on amino acid residues), wherein in these compounds, the allyl on the tyrosine lateral chain and the alkenyl on the other end terminal residue share their double bond.

In specific embodiments, the size of the macrocycle can be of 17 to 29-ring atoms. In specific embodiment, the size of the macrocycle can be of 21- to 25-ring atoms. In specific embodiments, the macrocycle size is of 21 ring atoms (e.g., compound 8), 22 ring atoms (e.g., compounds 1, 7, 11, and 13-15), 23 ring atoms (e.g., compounds 2-6 and 12), 24 ring atoms (e.g., compound 9), or 25 ring atoms (e.g., compound 10).

In all the foregoing compounds, the residues (e.g., Xaa1 to Xaa6) may be in L or D configurations.

Chemical Groups

As used herein, the term "alkyl" refers to a monovalent straight or branched chain, saturated or unsaturated aliphatic hydrocarbon radical having a number of carbon atoms in the specified range. Thus, for example, "(C1-12)alkyl" (or "C1-12 alkyl") refers to any alkyl of up to 12 carbon atom, including of the hexyl alkyl and pentyl alkyl isomers as well as n-, iso-, sec- and t-butyl, n- and iso-propyl, ethyl, and methyl. As another example, "(C1-4)alkyl" refers to n-, iso-, sec- and t-butyl, n- and isopropyl, ethyl, and methyl. As another example, "C1-3 alkyl" refers to n-propyl, isopropyl, ethyl, and methyl. Alkyl include unsaturated aliphatic hydrocarbon including alkyne (R—C≡C—R); and/or alkene (R—C=C—R).

The term "halogen" (or "halo") refers to fluorine, chlorine, bromine and iodine (alternatively referred to as fluoro, chloro, bromo, and iodo). The term "haloalkyl" refers to an alkyl group as defined above in which one or more of the hydrogen atoms have been replaced with a halogen (i.e., F, Cl, Br and/or I). Thus, for example, "C1-10 haloalkyl" (or "C1-C6 haloalkyl") refers to a C1 to C10 linear or branched alkyl group as defined above with one or more halogen substituents. The term "fluoroalkyl" has an analogous meaning except that the halogen substituents are restricted to fluoro. Suitable fluoroalkyls include the series $(CH2)_{0-4}CF_3$ (i.e., trifluoromethyl, 2,2,2-trifluoroethyl, 3,3,3-trifluoro-n-propyl, etc.).

The term "heteroalkyl" is given its ordinary meaning in the art and refers to alkyl groups as described herein in which one or more carbon atoms is replaced with a heteroatom (e.g., oxygen, nitrogen, sulfur, or derivatives thereof, and the like). Examples of heteroalkyl groups include, but are not limited to, alkoxy, alkyl-substituted amino, thiol such as methionine side group. Up to two heteroatoms may be consecutive. When a prefix such as C2-6 is used to refer to a heteroalkyl group, the number of carbons (2-6, in this example) is meant to include the heteroatoms as well.

The term "aminoalkyl" refers to an alkyl group as defined above in which one or more of the hydrogen or carbon atoms has been replaced with a nitrogen or an amino derivative such as but not limited to guanidine. Thus, for example, "C1-6 aminoalkyl" (or "C1-C6 aminoalkyl") refers to a C1 to C6 linear or branched alkyl group as defined above with one or more amino derivatives (e.g., NH, amide, diazirin, azide, etc.).

The term "thioalkyl" refers to an alkyl group as defined above in which one or more of the hydrogen or carbon atoms has been replaced with a sulfur atom or thiol derivative. Thus, for example, "C1-6 aminoalkyl" (or "C1-C6 aminoalkyl") refers to a C1 to C6 linear or branched alkyl group as defined above with one or more sulfur atoms or thiol derivatives (e.g., S, SH, etc.).

Aminoalkyl and thioalkyls are specific embodiments of and encompassed by the term "heteroalkyl" or substituted alkyl depending on the heteroatom replaces a carbon atom or an hydrogen atom.

The term "cycloalkyl" refers to saturated alicyclic hydrocarbon consisting of saturated 3-8 membered rings optionally fused with additional (1-3) aliphatic (cycloalkyl) or aromatic ring systems, each additional ring consisting of a 3-8 membered ring. It includes without being so limited cyclopropane, cyclobutane, cyclopentane, and cyclohexane.

The term "heterocyclyl" refers to (i) a 4- to 7-membered saturated heterocyclic ring containing from 1 to 3 heteroatoms independently selected from N, O and S, or (ii) is a heterobicyclic ring (e.g., benzocyclopentyl). Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

The term "C(O)" refers to carbonyl. The terms "S(O)$_2$" and "SO$_2$" each refer to sulfonyl. The term "S(O)" refers to sulfinyl.

The term "aryl" refers to aromatic (unsaturated) compounds consisting of 3-8 membered rings, optionally fused with additional (1-3) aliphatic (cycloalkyl) or aromatic ring systems, each additional ring consisting of 3-8 membered ring. In a specific embodiment, it refers to phenyl, benzocyclopentyl, or naphthyl. The aryl of particular interest is phenyl. The term "heteroaryl" refers to (i) a 3-, 4-, 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 3-, 4-, 5- and 6-membered heteroaromatic rings include, for example, diazirin, pyridyl (also referred to as pyridinyl), pyrrolyl, diazine (e.g., pyrazinyl, pyrimidinyl, pyridazinyl), triazinyl, thienyl, furanyl, imidazolyl, pyrazolyl, triazolyl (e.g., 1, 2, 3 triazolyl), tetrazolyl (e.g., 1, 2, 3, 4 tetrazolyl), oxazolyl, iso-oxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl. Suitable heterobicyclic rings include indolyl.

The term "aralkyl" and more specifically "(C4-C14)aralkyl" or "C4-14 aralkyl" refers herein to compounds comprising a 3-7 ring-member aryl substituted by a 1 to 7 alkyl. In specific embodiments, it refers to a benzyl or a phenetyl.

As used herein, and unless otherwise specified, the terms "alkyl", "haloalkyl", "aminoalkyl", "cycloalkyl", "heterocycyl", "aryl", "heteroalkyl" and "heteroaryl" and the terms designating their specific embodiments (e.g., butyl, fluoropropyl, aminobutyl, cyclopropane, morpholine, phenyl, pyrazole, etc.) encompass the substituted (i.e. in the case of haloalkyl and aminoalkyl, in addition to their halogen and nitrogen substituents, respectively) and unsubstituted embodiments of these groups. Hence for example, the term "phenyl" encompasses unsubstituted phenyl as well as fluorophenyl, hydroxyphenyl, methylsulfonyl phenyl (or biphenyl), trifluoromethyl-dazirin-phenyl, isopropyl-phenyl, trifluorohydroxy-phenyl. Similarly, the term pyrazole, encompass unsubstituted pyrazole as well as methylpyrazole. The one or more substituents may be an amine, halogen, hydroxyl, C1-6 aminoalkyl, C1-6 heteroalkyl, C1-6 alkyl, C3-8 cycloalkyl, C1-6 haloalkyl, aryl, heteroaryl and heterocyclyl groups (etc.).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Isomers, Tautomers and Polymorphs

As used herein, the term "isomers" refers to optical isomers (enantiomers), diastereoisomers as well as the other known types of isomers.

The compounds of the invention have at least 5-6 asymmetric carbon atoms and can therefore exist in the form of optically pure enantiomers (optical isomers), as racemates and as mixtures thereof. The compounds have at least five asymmetric carbon atoms and can therefore exist in the form of pure diastereoisomers and as mixtures thereof. It is to be understood, that, unless otherwise specified, the present invention embraces the racemates, the enantiomers and/or the diastereoisomers of the compounds of the invention as well as mixtures thereof. For example, the compounds 2 and 4 of the present invention are diastereoisomers; and the compounds 3 and 12 of the present invention are diastereoisomers.

For further clarity, (S)—H or (S)—$CH_3$ indicates that the stereogenic center bearing the H or $CH_3$ substituent is of (S) stereochemistry.

In addition, the present invention embraces all geometric isomers. For example, when a compound of the invention incorporates a double bond or a fused ring, both the cis- and trans-forms, as well as mixtures, are embraced within the scope of the invention.

Within the present invention, it is to be understood that a compound of the invention may exhibit the phenomenon of tautomerism and that the formula drawings within this specification can represent only one of the possible tautomeric forms. It is to be understood that the invention encompasses any tautomeric form and is not to be limited merely to any one tautomeric form utilized within the formula drawings.

It is also to be understood that certain compounds of the invention may exhibit polymorphism, and that the present invention encompasses all such forms.

Salts

The present invention relates to the compounds of the invention as hereinbefore defined as well as to salts thereof. The term "salt(s)", as employed herein, denotes basic salts formed with inorganic and/or organic bases. Salts for use in pharmaceutical compositions will be pharmaceutically acceptable salts, but other salts may be useful in the production of the compounds of the invention. The term "pharmaceutically acceptable salts" refers to salts of compounds of the present invention that are pharmacologically acceptable and substantially non-toxic to the subject to which they are administered. More specifically, these salts retain the biological effectiveness and properties of the anti-atherosclerosis compounds of the invention and are formed from suitable non-toxic organic or inorganic acids or bases.

For example, where the compounds of the invention are sufficiently acidic, the salts of the invention include base salts formed with an inorganic or organic base. Such salts include alkali metal salts such as sodium, lithium, and potassium salts; alkaline earth metal salts such as calcium and magnesium salts; metal salts such as aluminum salts, iron salts, zinc salts, copper salts, nickel salts and a cobalt salts; inorganic amine salts such as ammonium or substituted ammonium salts, such as e.g., trimethylammonium salts; and salts with organic bases (for example, organic amines) such as chloroprocaine salts, dibenzylamine salts, dicyclohexylamine salts, dicyclohexylamines, diethanolamine salts, ethylamine salts (including diethylamine salts and triethylamine salts), ethylenediamine salts, glucosamine salts, guanidine salts, methylamine salts (including dimethylamine salts and trimethylamine salts), morpholine salts, morpholine salts, N,N'-dibenzylethylenediamine salts, N-benzyl-phenethylamine salts, N-methylglucamine salts, phenylglycine alkyl ester salts, piperazine salts, piperidine salts, procaine salts, t-butyl amines salts, tetramethylammonium salts, t-octylamine salts, tris-(2-hydroxyethyl) amine salts, and tris(hydroxymethyl)aminomethane salts. Preferred salts include those formed with sodium, lithium, potassium, calcium and magnesium.

Such salts can be formed routinely by those skilled in the art using standard techniques. Indeed, the chemical modification of a pharmaceutical compound (i.e. drug) into a salt is a technique well known to pharmaceutical chemists, (See, e.g., H. Ansel et. al., Pharmaceutical Dosage Forms and Drug Delivery Systems (6th Ed. 1995) at pp. 196 and 1456-1457, incorporated herein by reference). Salts of the compounds of the invention may be formed, for example, by reacting a compound of the invention with an amount of acid or base, such as an equivalent amount, in a medium such as one in which the salt precipitates or in an aqueous medium followed by lyophilization.

Esters

The present invention relates to the compounds of the invention as hereinbefore defined as well as to the esters thereof. The term "ester(s)", as employed herein, refers to compounds of the invention or salts thereof in which hydroxy groups have been converted to the corresponding esters using, for example, inorganic or organic anhydrides, acids, or acid chlorides. Esters for use in pharmaceutical compositions will be pharmaceutically acceptable esters, but other esters may be useful in the production of the compounds of the invention.

The term "pharmaceutically acceptable esters" refers to esters of the compounds of the present invention that are pharmacologically acceptable and substantially non-toxic to the subject to which they are administered. More specifically, these esters retain the biological effectiveness and properties of the anti-atherosclerosis compounds of the invention and act as prodrugs which, when absorbed into the bloodstream of a warm-blooded animal, cleave in such a manner as to produce the parent alcohol compounds.

Esters of the compounds of the present invention include among others the following groups (1) carboxylic acid esters obtained by esterification of the hydroxy groups, in which the non-carbonyl moiety of the carboxylic acid portion of the ester grouping is selected from straight or branched chain alkyl (for example, ethyl, n-propyl, t-butyl, n-butyl, methyl, propyl, isopropyl, butyl, isobutyl, or pentyl), alkoxyalkyl (for example, methoxymethyl, acetoxymethyl, and 2,2-dimethylpropionyloxymethyl), aralkyl (for example, benzyl), aryloxyalkyl (for example, phenoxymethyl), aryl (for example, phenyl optionally substituted with, for example, halogen, $C_{1-4}$ alkyl, or $C_{1-4}$ alkoxy, or amino); (2) sulfonate esters, such as alkyl- or aralkylsulfonyl (for example, methanesulfonyl); (3) amino acid esters (for example, L-valyl or L-isoleucyl); (4) phosphonate esters; (5) mono-, di- or triphosphate esters (including phosphoramidic cyclic esters). The phosphate esters may be further esterified by, for example, a $C_{1-20}$ alcohol or reactive derivative thereof, or by a 2,3-di($C_{6-24}$)acyl glycerol. (6) Carbamic acid ester (for example N-methylcarbamic ester); and (7) Carbonic acid ester (for example methylcabonate).

Further information concerning examples of and the use of esters for the delivery of pharmaceutical compounds is available in Design of Prodrugs. Bundgaard H ed. (Elsevier, 1985) incorporated herein by reference. See also, H. Ansel et. al., 1995 at pp. 108-109; Krogsgaard-Larsen, 1996 at pp.

152-191; Jarkko Rautio, 2008; and Pen-Wei Hsieh, 2009, all incorporated herein by reference.

The compounds of this invention may be esterified by a variety of conventional procedures including reacting the appropriate anhydride, carboxylic acid or acid chloride with an alcohol group of a compound of this invention. For example, an appropriate anhydride may be reacted with an alcohol in the presence of a base, such as 1,8-bis[dimethylamino]naphthalene or N,N-dimethylaminopyridine, to facilitate acylation. Also, an appropriate carboxylic acid can be reacted with an alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid. Reaction of an acid chloride with an alcohol can also be carried out. When a compound of the invention contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities. One skilled in the art would readily know how to successfully carry out these as well as other known methods of esterification of alcohols.

Esters of the compounds of the invention may form salts. Where this is the case, this is achieved by conventional techniques as described above.

Solvates

The compounds of the invention may exist in unsolvated as well as solvated forms with solvents such as water, ethanol, and the like, and it is intended that the invention embrace both solvated and unsolvated forms.

"Solvate" means a physical association of a compounds of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Solvates for use in pharmaceutical compositions will be pharmaceutically acceptable solvates, but other solvates may be useful in the production of the compounds of the invention.

As used herein, the term "pharmaceutically acceptable solvates" means solvates of compounds of the present invention that are pharmacologically acceptable and substantially non-toxic to the subject to which they are administered. More specifically, these solvates retain the biological effectiveness and properties of the anti-atherosclerosis compounds of the invention and are formed from suitable non-toxic solvents.

Non-limiting examples of suitable solvates include ethanolates, methanolates, and the like, as well as hydrates, which are solvates wherein the solvent molecules are $H_2O$.

Preparation of solvates is generally known. Thus, for example, Caira, 2004, incorporated herein by reference, describe the preparation of the solvates of the antifungal fluconazole in ethyl acetate as well as from water. Similar preparations of solvates, hemisolvate, hydrates and the like are described by van Tonder, 2004; Bingham, 2001, both incorporated herein by reference.

A typical, non-limiting, process for preparing a solvate involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, can be used to show the presence of the solvent (or water) in the crystals as a solvate (or hydrate).

Compositions, Combination and Kits

Compostions

The present invention also relates to pharmaceutical compositions comprising the above-mentioned compounds of the invention or their pharmaceutically acceptable salts, esters and solvates thereof and optionally a pharmaceutically acceptable carrier.

As used herein, the terms "pharmaceutically acceptable" refer to molecular entities and compositions that are physiologically tolerable and do not typically produce an allergic or similar untoward reaction, such as gastric upset, dizziness and the like, when administered to subjects (e.g., humans). Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin. The pharmaceutical compositions of the present invention may also contain excipients/carriers such as preserving agents, solubilizing agents, stabilizing agents, wetting agents, emulsifiers, sweeteners, colorants, odorants, salts for the variation of osmotic pressure, buffers, coating agents or antioxidants.

Any appropriate route of administration may be employed, include parenteral (by injection) and enteral (gastrointestinal route). More specifically, parenteral routes include for example, intravenous, intrathecal, intracerebroventricular, intradermal, transdermal (topical), subcutaneous, intramuscular, intramammary, intracranial, intraorbital, ophthalmic, intraventricular, intracapsular, intraarticular, intraspinal, intracisternal, and intraperitoneal; Enteral include oral, intranasal, sublingual, transmucosal or rectal administration.

Without being so limited, when the compound/pharmaceutical compositions of the invention is administered orally, it may take the form of tablets, coated tablets, dragees, hard or soft gelatin capsules, solutions, emulsions or suspensions for example; rectally using for example of suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as opthalmological preparations or an aerosol, for example in the form of a spray, such as a nasal spray.

The compounds of the invention may be incorporated into dosage forms in conjunction with any of the vehicles which are commonly employed in pharmaceutical preparations. Methods for preparing appropriate formulations are well known in the art (see e.g., Remington's Pharmaceutical Sciences, 16th Ed., 1980, A. Oslo Ed., Easton, Pa. incorporated herein by reference). Common pharmaceutically acceptable carriers include, without limitation, sterile aqueous or non-aqueous solutions, suspensions, and emulsions.

Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

For the preparation of tablets, coated tablets, dragees or hard gelatin capsules, the compounds of the present invention may be admixed with any known pharmaceutically inert, inorganic or organic excipient and/or carrier. Examples of suitable excipients/carriers include lactose, maize starch or derivatives thereof, talc or stearic acid or salts thereof. Suitable excipients for use with soft gelatin capsules include for example vegetable oils, waxes, fats, semi-solid or liquid polyols etc. According to the nature of the active ingredients it may however be the case that no excipient is needed at all for soft gelatin capsules. For the preparation of solutions and syrups, excipients which may be used include for example water, polyols, saccharose, invert sugar and glucose.

For suppositories, and local or percutaneous application, excipients which may be used include for example natural or hardened oils, waxes, fats and semi-solid or liquid polyols.

In cases where parenteral administration is elected as the route of administration, preparations containing the compounds of the invention may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically active agents.

Any amount of a pharmaceutical composition can be administered to a subject. The dosages will depend on many factors including the age and the requirements of the patient and the mode of application. Typically, the amount of the compound of the invention contained within a single dose will be an amount that effectively prevent, delay or treat the disease or condition to be treated, delayed or prevented without inducing significant toxicity. Hence a "therapeutically effective amount" or "effective amount" or "therapeutically effective dosage" of a specific compound of the invention or composition thereof can result in a reduction of pain and/or body temperature in a subject. Intravenous, or oral administrations are preferred forms of use.

The effective amount of the compounds of the invention may also be measured directly. The effective amount may be given daily or weekly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount may range from about 1 mg to about 25 grams of the composition per day, about 50 mg to about 10 grams of the composition per day, from about 100 mg to about 5 grams of the composition per day, about 1 gram of the composition per day, about 1 mg to about 25 grams of the composition per week, about 50 mg to about 10 grams of the composition per week, about 100 mg to about 5 grams of the composition every other day, and about 1 gram of the composition once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the pharmaceutical composition of the invention is given to the patient, but it is particularly advisable in such cases to begin with low doses to determine if adverse side effects are experienced.

Combinations

In accordance with another aspect, there is provided a combination of at least one of the compounds described herein with another of the compounds described herein and/or with another antalgic agent (e.g., analgesic) and/or with another agent or therapy (ex. cooling catheter, cooling blanket, ice around the body) that reduces body temperature and/or with an agent that prevents or treats pain comorbidities such as anxiety (anxiolytic) and/or depression (antidepressant). Without being so limited, other antalgic (e.g., analgesic) agents include acetylsalicylic acid, nonsteroidal anti-inflammatory drugs (NSAIDs) (e.g., ibuprofen, ketoprofen), acetaminophen, etc. Without being so limited, weak opioids such as codeine, dihydrocodeine, tramadol, and strong opioids such as morphine, buprenorphine, and fentanyl. Without being so limited anxiolytic agents include benzodiazepine tetrazepam. Without being so limited antidepressant agents include anafranil, clomipramine, etc. In a specific embodiment, the combination of the compounds of the present invention with another active ingredient (e.g., an opioid), advantageously enables reducing the dose that would be required if each compound was used alone, thereby reducing the deleterious side effects of each.

In accordance with an aspect, there is provided a composition comprising at least one of the compounds as described herein, and (i) another of the compounds described herein; (ii) another analgesic and/or antalgic agent; (iii) a pharmaceutically acceptable carrier; or (iv) a combination of at least two of (i) to (iii).

In a specific embodiment, said composition is a pharmaceutical composition. In another specific embodiment, the composition comprises (i) a compound as described herein; and (ii) another analgesic and/or antalgic agent.

Kits

In accordance with another aspect of the present invention, there is provided a kit comprising the compound defined herein or the above-mentioned composition, and instructions to use same in the prevention or treatment of pain or of a symptom thereof, or instructions to use same in the lowering of body temperature.

In a specific embodiment of the kit, the kit comprises: (i) at least one of the compounds described herein; (ii) another antalgic agent (e.g., analgesic); (iii) instructions to use same in the prevention or treatment of pain or of a symptom thereof or instructions to use same in the lowering of body temperature; or (iv) a combination of at least two of (i) to (iii).

Methods

The present invention also relates to a method of preventing or treating pain comprising administering to a subject in need thereof an effective amount of a compound described herein, or a composition described herein.

The present invention also relates to a method of lowering body temperature of a subject in need thereof comprising administering to the subject an effective amount of a compound described herein, a composition described herein.

As used herein the terms "subject" refers to an animal such as, but not limited to a human or a pet or other animal (e.g., pets such as cats, dogs, horses, etc.; and cattle, fishes, swine, poultry, etc.).

As used herein the terms "subject in need thereof" refer to a subject who would benefit from receiving an effective amount of the compound or composition of the present invention. In the context of the method of preventing or treating pain, it refers to a subject experiencing or at risk to experience pain (e.g., chronic or acute). In another specific embodiment, the subject at risk to experience pain, is, without being so limited, a subject immediately prior to surgery. In the context of the method of lowering body temperature (hypothermia), it refers to a subject that or likely to benefit from lowering of the body temperature. In a specific embodiment, it refers to a subject that is at-risk for experiencing, has recently experienced, or is undergoing a stroke or a myocardial infarction. In a specific embodiment, a subject at-risk for experiencing a stroke is a subject prior to surgery such as, but not limited to cardiac intervention such as coronary angiography, percutaneous coronary intervention, open heart operation, catheter ablation of atrial fibrillation; intracranial stenting. In a specific embodiment, the subject that would benefit from the hypothermia effect of the compounds of the present invention, would also benefit from its analgesic effect. For example, a subject that has stroke may also experience pain such as a migraine or a headache. A subject that will undergo surgery and that is at-risk for experiencing a stroke, is also at risk for experiencing post-surgery pain.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

The present invention is illustrated in further details by the following non-limiting examples.

Example 1: Material and Method

Peptide Synthesis

Peptides were synthesized using standard Fmoc chemistry on 2-chlorotrityl resin (loading: 0.75 mmol/g) obtained from Chem Impex or Matrix Innovation. Fmoc-protected amino-acids and coupling reagents were purchased from the same manufacturers, in the highest available purity and were used as received. Peptide synthesis was performed in 12 mL polypropylene cartridges with 20 µm PE frit from Applied Separations (USA), with orbital shaking at 140 rpm. All quantities given below are for 100 µmol of peptide (130 mg of resin). Other chemical reagents as well as PD149163 were purchased from Sigma-Aldrich. Equivalents are calculated with respect to nominal resin loading. Purity of all compounds in this manuscript was >95% as assessed by UPLC.

Coupling of the First Amino-Acid to the Resin

The resin was swelled in DCM for 15 min, then stirred for 30 min with 1.5 mL of a DCM solution containing 5 eq of the Fmoc-protected amino-acid and DIEA (104 µL, 6 eq). The resin was washed with DCM (2×5 mL), iPrOH (Isopropanol) (2×5 mL), and DCM (2×5 mL). Unreacted sites were capped by stirring 30 min with 1.5 mL of a DCM/MeOH(methanol)/DIEA (7:2:1) solution and the resin was washed again as mentioned above.

Fmoc Deprotection

Fmoc groups were removed by treating the resin with a 20% pipendine/DMF (Dimethylformamide) solution (2×10 min). The resin was then washed with DMF (2×5 mL), DCM (2×5 mL), iPrOH (2×5 mL), DCM (2×5 mL) and DMF (2×5 mL).

Coupling of Commercial Amino-Acids

Figure 3:
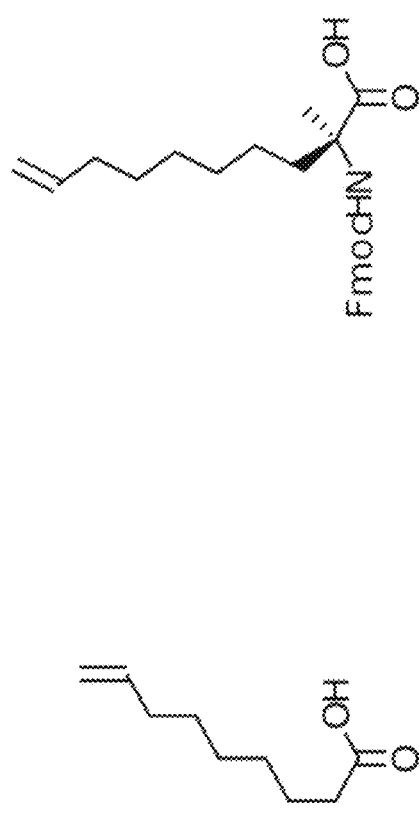
FIG. 3: Structure of illustrative non-natural amino acids used in compounds of the present invention, namely non-enoic acid, Fmoc-(S)-α-methyl-octenylalanine (Fmoc-(S)-2-(7-Octenyl)alanine), Boc-Lys(Fmoc)-OH, Boc-Ornithine (Fmoc)-OH and $N^\alpha$-Boc,$N^\gamma$-Fmoc-diaminobutyric acid.
Figure 3:
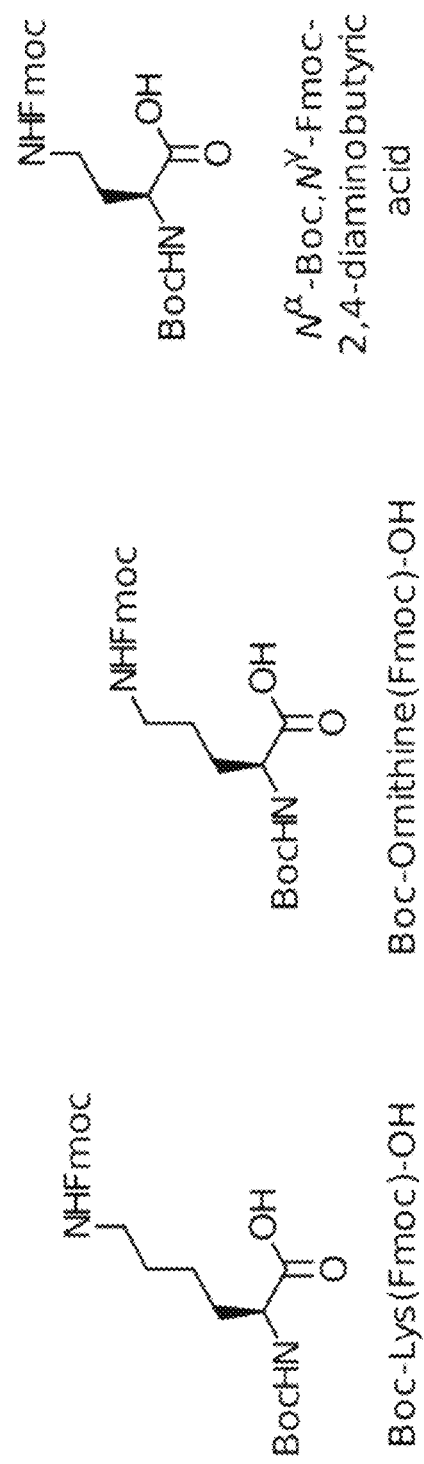

The resin was treated with a solution of Fmoc-amino-acid (0.5 mMol, 5 eq), 1-[Bis(dimethylamino)methylene]-1H-1,2,3-triazolo[4,5-b]pyridinium 3-oxide hexafluorophosphate (HATU) (95 mg, 5 eq) and DIEA (104 µL, 6 eq) in DMF (1.5 mL) for 30 min, then washed with DMF (2×5 mL), DCM (2×5 mL), PrOH (2×5 mL), DCM (2×5 mL) and DMF (2×5 mL). Commercially available alkene-amino adds used are shown in FIG. 3.

Coupling of Non-Commercial or Costly Amino-Acids

The resin was treated with a solution of Fmoc-amino-acid (0.2 mMol, 2 eq), HATU (38 mg, 0.2 mmol, 2 eq) and DIEA (52 µL, 0.3 mmol, 3 eq) in DMF (1.5 mL) for 2 h, then washed with DMF (2×5 mL), DCM (2×5 mL), PrOH (2×5 mL), and DCM (2×5 mL). The procedure was repeated if the resin beads turned blue when submitted to the Kaiser test.

On-Resin Nosylation of Amines 2-nitrobenzenesulfonyl (nosyl) chloride (221 mg, 0.4 mmol, 4 eq) and 2,4,6-trimethylpyridine (132 NIL, 1 mmol, 10 eq) were dissolved in NMP (1.5 mL). This solution was poured into the reactor containing the resin-bound free-amine peptide. After 30 minutes of stirring, the solution was filtered off and this step was repeated once or until the Kaiser test returned negative. The resin was then washed with NMP (2×5 mL), DCM (2×5 mL), PrOH (2×5 mL), DCM (2×5 mL) and DMF (2×5 mL).

Kaiser Test

The completion of amino-acid couplings and nosylations were assessed by transferring a few resin beads in a 6×50 mm glass culture tube, then adding one drop of 0.2 mM KCN in pyridine/$H_2O$ (98:2), one drop of 5% ninhydrin in n-butanol and one drop of 20 M phenol in n-butand. Upon heating of the mixture, the beads turn blue if free amines remain.

Acetylation of Tyrosine

The resin was stirred for one hour in the presence of acetic anhydride (19 μL, 0.2 mmol, 2 eq) and DIEA (35 μL, 0.2 mmol, 2 eq) in DCM (1.5 mL). This step was repeated once or until reaction completion was confirmed by UPLC-MS. (after cleavage of a small amount of resin with DCM/TFA/TiS 99:0.5:0.5). The resin was then washed with DMF (2×5 mL), DCM (2×5 mL), iPrOH (2×5 mL), DCM (2×5 mL) and DMF (2×5 mL).

Fukuyama-Mitsunobu Alkylation

Triphenylphosphine (131 mg, 0.5 mmol, 5 eq) and the alcohol (1 mmol, 10 eq) were dissolved in anhydrous THF (1.5 mL) and this solution was poured into the reactor containing the resin-bound peptide. DIAD (98 μL, 0.5 mmol, 5 eq) was added and the mixture stirred for 30 min. The solution was filtered off and this step was repeated once or until reaction completion was confirmed by UPLC-MS. (after cleavage of a small amount of resin with DCM/TFA/TiS 99:0.5:0.5). The resin was then washed with THF (tetrahydrofurane)(2×5 mL), DCM (2×5 mL), PrOH (2×5 mL), DCM (2×5 mL) and DMF (2×5 mL).

Ring-Closing Metathesis

The dried resin, Hoveyda-Grubbs $2^{nd}$ generation catalyst (12.5 mg, 0.02 mmol, 0.2 eq) and p-benzoquinone (11 mg, 0.1 mmol, 1 eq) were placed in a microwave tube which was then purged with argon. Anhydrous DCE (1.5 mL) was added before submitting the mixture to microwave irradiation (50° C., 60 min). The resin was then washed with DCM (5×5 mL).

Simultaneous Nosyl and Acetyl Deprotectlon 2-mercaptoethanol (70 μL, 1 mmol, 10 eq) and DBU (74 μL, 0.5 mmol, 5 eq) were dissolved in NMP (1.5 mL) and the solution was poured in the reactor containing the resin-bound peptide. After 30 minutes stirring, the solution was filtered off and this step was repeated once. The resin was then washed with NMP (2×5 mL), DCM (2×5 mL), PrOH (2×5 mL), DCM (2×5 mL) and DMF (2×5 mL).

Cleavage from the Resin and Side-Chain Deprotections

The resin was transferred to a 20-mL glass vial and stirred for 2 h with 3 mL of a TFA/DCM/TiS (Triisopropylsilane) (50:49:1) solution. The peptide was then precipitated in 20 mL of cold tBME (tert-butyl methyl ether), centrifuged (3000 rpm (rotations per minute), 15 min, 4° C.), then dried in vacuo.

Peptide Purification

The crude product was dissolved in water/acetonitrile (7:3) and purified on a preparative HPLC-MS system from Waters (column XSELECT™ CSH™ Prep C18 (19×100 mm) packed with 5 μm particles, UV detector 2998, MS SQ Detector™ 2, Sample Manager 2767 and a binary gradient module) using acetonitrile and water+0.1% formic acid as eluents. Purified fractions were lyophilized and the purity of obtained compounds was assessed on an UPLC-MS system (column Acquity UPLC™ CSH™ C18 (2.1×50 mm) packed with 1.7 μm particles) with the following gradient: acetonitrile and water with 0.1% TFA (0→0.2 min: 5% acetonitrile; 0.2→1.5 min: 5%→95%; 1.5→1.8 min: 95%; 1.8→2.0 min: 95%→5%; 2.0→2.5 min: 5%). Despite several attempts, E and Z isomers did not separate. High resolution mass spectra (HRMS) of all compounds of the invention were obtained using electrospray infusion ESI-Q-Tof™ from maXis.

Synthesis of Unnatural Amino Acid Derivatives

Fmoc-aminohexanoic acid: aminohex-6-enoic acid (1 g, 7.5 mmol) was dissolved into 20 mL water. Sodium bicarbonate (1.3 g, 15.2 mmol, 2 eq.) was added. Fmoc-Cl (2.3 g, 9.1 mmol, 1.2 eq.) was dissolved into 15 mL dioxane and this solution was added to the mixture. After 4 h stirring, dioxane was evaporated in vacuo and the aqueous phase was washed with diethyl ether. The pH of the aqueous phase was adjusted to 2 by addition of 1N HCl, then the product was extracted with ethyl acetate. The organic phase was washed with brine, dried over $MgSO_4$, filtered and evaporated in vacuo. The product was purified by flash chromatography to give 1.8 g of a yellow oil (72% yield).

$^1$H NMR ($CDCl_3$, 400 MHz): δ 7.74 (d, J=7.6 Hz, 2H), 7.57 (d, J=7.2 Hz, 2H), 7.38 (t, J=7.5, 2H), 7.29 (t, J=7.5 Hz, 2H), 4.39 (d, J=6.9 Hz, 2H), 4.19 (t, J=6.9 Hz, 1H), 3.18 (q, J=6.5 Hz, 2H), 2.34 (t, J=7.3 Hz, 2H), 1.64 (dt, J=14.9, 7.5 Hz, 2H), 1.51 (dt, J=14.6, 7.3, 2H), 1.35 (dt, J=14.7, 7.4, 2H). $^{13}$C NMR ($CDCl_3$, 100 MHz): δ 177.73, 143.82, 141.17, 127.5, 126.86, 124.86, 119.81, 66.35, 47.14, 40.62, 33.40, 29.46, 25.94, 24.09.

Fmoc-Tyr-o-Allyl-OH was synthesized as described previously (Sousbie, 2018).

Binding Assays

Cell Culture and Transfections

CHO-K1 (Chinese Hamster Ovary) cells stably expressing hNTS1 (ES-690-C from PerkinElmer, Montréal, Canada) were cultured in DMEM F12 culture medium at 37° C. in a humidified chamber under 5% $CO_2$. Culture media were supplemented with 10% FBS, 100 U/mL penicillin, 100 μg/mL streptomycin, 20 mM HEPES, and 0.4 mg/mL G418 at 37° C.

Cells were frozen when they reached 80% confluency. They were scrapped off the dish with 10 mM Tris buffer, 1 mM EDTA, pH 7.5 and centrifuged at 15,000 g for 5 min at 4° C. The pellet was then re-suspended in binding buffer.

DRG-F11 cells were cultured in DMEM supplemented with 10% FBS, 100 U/mL penicillin, 100 μg/mL streptomycin, and 20 mM HEPES. DRG-F11 were seeded at $2.2 \times 10^6$ cells in a 10 cm Petri dish and transfected 24 h after plating with 10 μg of DNA coding for the rat NTS2-YFP receptor using Xtreme Gene™ HP as a transfection agent. Membrane preparation was conducted 48 h after transfection, as described below.

Competitive Radioligand Binding Assay on the hNTS1 Receptor

Competitive radioligand binding experiments were performed by incubating 15 μg of cell membranes expressing the hNTS1 receptor with 45 pM of $^{125}$I-[Tyr$^3$]-NT (2200 Ci/mmol purchased from PerkinElmer, Billerica, Mass.) in binding buffer (50 mM Tris-HCl, pH7.5, 0.2% BSA) in the presence of increasing concentrations of the compounds of the invention ranging from $10^{-11}$ to $10^{-4}$ M for 60 min at 25° C. After incubation, the binding reaction mixture was transferred in polyethylenimine (PEI)-coated 96-well filter plates (glass fiber filters GF/B, Millipore, Billerica, Mass.). Reaction was terminated by filtration, and plates were washed three times with 200 µL ice-cold binding buffer. Glass filters were then counted using a γ-counter (2470 Wizard2, PerkinElmer, Missisauga, Ontario, Canada).

Non-specific binding was measured in the presence of $10^{-5}$ M unlabeled NT[8-13] (neurotensin (8-13)) and represented less than 5% of total binding. $IC_{50}$ (Inhibitory Concentration 50) values were determined from the competition curves as the unlabeled ligand concentration inhibiting half of the $^{125}I$-[Tyr]-NT-specific binding.

Competitive radioligand binding data were plotted using Prism™ 7 (GraphPad, La Jolla, Calif.) using a custom equation for the fitting of a One-site-Fit Log($IC_{50}$) with a variable pseudo-Hill Slope and represented the mean±SEM of at least three separate experiments. $IC_{50}$ were then transformed into $K_i$ values using the Cheng-Prusoff equation and the Kd value of $^{125}I$-[Tyr]-NT from the saturation binding curve. $K_i$ values represent the mean±SEM of at least three separate experiments.

Competitive Radioligand Binding Assay on the rNTS2 Receptor

Transfected cells expressing the rNTS2-YFP receptor were used 48 h after transfection. Membranes were prepared by scraping cells off the culture dish with 50 mM Tris ph 7.5 and centrifuged at 15,000 g for 5 min at 4° C. The pellet was resuspended in 10 mM Tris, 1 mM EDTA pH 7.5 and sonicated for 30 s prior to be centrifugated at 15,000 g for 30 min at 4° C. The pellet was then re-suspended in binding 9 buffer. Competitive radioligand binding experiments were performed by incubating 50 µg of cell membranes expressing the rNTS2 receptor with 130 pM of $^{125}I$-[Tyr$^3$]-NT (2200 Ci/mmol) in binding buffer (50 mM Tris-HCl, pH7.5, 0.2% BSA). All other steps in binding experiments were unchanged comparing to the one using the NTS1 receptor.

BRET Assays

CHO-K1 cells were cultured in DMEM-F12 supplemented with 10% FBS, 100 U/mL penicillin, 100 µg/mL streptomycin, and 20 mM HEPES at 37° C. in a humidified chamber at 5% $CO_2$. Cells were seeded into T75 flasks at a density of 20 000 cells/cm$^2$; 24 h later, cells were transfected with plasmids coding for hNTS1-Green fluorescent protein 10(GFP10)/Rluc (Renilla Luciferase)II-β-arrestin 1 or hNTS1-GFP10/RlucII-β-arrestin2, or with hNTS1/Gαq-RlucII/Gβ1/IGFP10-Gγ1 or hNTS1/Gα13-RlucII/Gβ1/GFP10-Gγ1 using polyethylenimine (PEI). Cells were transferred into 96-well plates at a concentration of 50 000 cells/well 24 h after transfection and incubated at 37° C. overnight. They were then washed with PBS and 90 µL HBSS was added in each well. Cells were then stimulated with increasing concentrations of each analog ranging from $10^{-11}$ to $10^{-5}$ M ($10^{-12}$ to $10^{-6}$ M in the case of NT[8-13]) for 20 min (β-arrestin 1 & 2) or 5 min (Gαq and Gα13) at 37° C. After stimulation, coelenterazine 400A was added in each well to a final concentration of 5 µM and the plate was read using filter selected for BRET2 measurement (BRET2 High efficiency filter set, $\lambda em_{RlucII}$: 410±80 nm, $\lambda em_{GFP10}$: 515±40 nm) on a Mithras 2 plate reader (Berthold Technologies, Tennessee, USA). BRET2 ratio was determined as GFP10em/RlucIIem. Data were analyzed using GraphPad Prism 7, normalization was done by using the BRET2 ratio of non-stimulated cells as 0% and the ratio of cells stimulated with $10^{-6}$ M NT[8-13] as 100% activation. EC50 (Effective Concentration 50) values were determined using the dose response-stimulation log(agonist) vs response (three parameters) and represent the mean±SEM of at least three separate experiments, each performed in triplicate.

Plasma Stability Assay

Rat plasma was obtained by centrifugation of rat blood (13000 rpm, 5 min, 4° C.). 6 µL of a 1 mM aqueous solution (10% DMSO (Dimethylsulfoxide)) of peptide were incubated with 27 µL of rat plasma at 37° C. for 5, 10, 30 and 60 min (1, 3 and 5 min for NT (neurotensin) (8-13)). Proteolytic degradation was quenched by adding 70 µL of acetonitrile/ethanol (1:1), 0.5% nicotinamide solution and vortexing. Samples were centrifuged (13000 rpm, 5 min, 4° C.) and the supernatant was filtered on a 4-mm nylon 0.2 µm syringe filter and analyzed by UPLC-MS (Waters 2695 with ACE C18 column 2.0×100 mm, 2.7 µm spherical particle size and Electrospray micromass ZQ-2000 from Waters). Data were analyzed using GraphPad Prism 7's one phase decay equation.

In Vivo Analgesic Assay

Animals, Housing, and Habituation

Experiments were performed with adult male Sprague-Dawley rats, weighing 225-300 g (Charles River laboratories, St-Constant, Canada). Rats were housed two per cage on Aspen shavings in a quiet room and kept on a 12 h light/dark cycle and allowed ad libitum access to food and water. The experimental procedures in this study were approved by the Animal Care Committee of Université de Sherbrooke (animal care protocol 035-13) and were in accordance with policies and directives of the Canadian Council on Animal Care.

Intrathecal Administration

Rats were lightly anesthetized with isoflurane/oxygen (Baxter corporation, Mississauga, ON, Canada; 2 L/min) flow and injected intrathecally at the L5-L6 intervertebral space with either 30 µg/kg of compound 1 diluted in 0.9% saline or 0.9% saline alone.

Acute Antinociceptive Effects

Tail-Flick Test:

Acute pain was assessed using the tail-flick test (Tail-Flick Analgesia meter V2.00, Colombus Instruments, Columbus, Ohio, USA). Tail-flick test measures sensitivity to a high-intensity light beam focused on the rat tail. The tail-flick apparatus was set at a light intensity of 6 and a cutoff of 10 sec. The latency, in seconds, to flick the tail out of the path of the light beam corresponds to the measure of pain sensitivity or analgesia.

Before testing, animals were individually acclimatized to manipulations and behavioral apparatus 5 min/day for three consecutive days. On the test day, latencies baseline measures were taken before drug injection to provide a mean baseline. Compounds 2, 3, 7 and PD149163 were diluted in 0.9% saline and injected at the same dose of 30 µg/kg. The effects of compounds or saline on thermal nociception were assessed every 10 min for up to 60 min following i.t. administration.

Tail-flick latencies were converted into the percent maximal possible effect (% MPE) at the time of maxima peak of analgesia. % MPE were calculated according to the following formula: % MPE=[(Test latency)−(Saline latency)]/[(Cutoff)−(Saline latency)]×100. Data are expressed as mean±SEM of 3-8 animals for each different compound.

Formalin Test:

The analgesic effect of compounds 3, 7 and PD149163 was assessed using the formalin test as a model of persistent pain. 5 min after intrathecal injection of compounds at 30 µg/kg, the rats received 50 µl of diluted 2% formaldehyde (i.e. 5% formalin; Bioshop, Burlington, Ontario) into the plantar surface of the right hind paw. Rats were then placed in clear plastic chambers (30×30×30 cm) positioned over a mirror angled at 45° in order to allow an unobstructed view of the paws and their behaviors were observed for the next 60 min. An intraplantar injection of formalin produced the biphasic nociceptive response typical of this tonic pain model.[61] The two distinct phases of spontaneous pain behaviors that occur in rodents are proposed to reflect a direct effect of formalin on sensory receptors (acute phase) and a longer lasting pain due to inflammation and central sensitization (inflammatory phase). Nociceptive behaviors were assessed using a weighted score as described previously. Following injection of formalin into the hind paw, nociceptive mean score was determined for each 3-min block during 60 min by measuring the amount of time spent in each of four behavioral categories: 0, the injected paw is comparable to the contralateral paw; 1, the injected paw has little or no weight placed on it; 2, the injected paw is elevated and is not in contact with any surface; 3, the injected paw is licked, bitten, or shaken. The behaviors believed to represent higher levels of pain intensity were given higher weighted scores. The weighted average pain intensity score ranging from 0 to 3 was then calculated by multiplying the time spent in each category by the category weight, summing these products, and dividing by the total time in a given time interval. The pain score was thus calculated from the following formula (1T1+2T2+3T3)/180 where T1, T2, and T3 are the durations (in seconds) spent in behavioral categories 1, 2, or 3, respectively, during each 180-sec block. The Area Under the Curve (AUC) was calculated during all the duration of the test (0-60 min). Data represent the mean±SEM of 4-7 rats for each condition.

Body Temperature

Body temperature was measured using a thermistor probe inserted into the rectum of adult Sprague-Dawley rats. Prior to testing, animals were individually acclimatized to manipulations and thermistor probe 5 min/day for three consecutive days. On the test day, temperature was measured before (baseline) and each 10 min for up to 60 min following intrathecal drug administration of compounds. Compound 7 was dissolved in 0.9% of saline and injected at different concentrations (0.3, 1, 3, 10 and 30 µg/kg). Compounds 3 and PD149163 were injected at 30 µg/kg (dissolved in 0.9% saline) and the body temperature was measured only at 60 min following i.t. injection. Changes in body temperature (Δ body temp) were determined from baseline for each time and each animal. Data represent the mean±SEM of 3-16 rats for each condition.

Blood Pressure

Rats were anesthetized with a mixture of ketamine/xylazine (87 mg/kg: 13 mg/kg, i.m.) and placed in supine position on a heated pad. Mean, systolic and diastolic arterial blood pressure and a heart rate were measured through a catheter (PE 50 filled with heparinized saline) inserted in the right carotid artery and connected to a Micro-Med™ transducer (model TDX-300, USA) linked to a blood pressure Micro-Med™ analyzer (model BPA-100c). Another catheter (PE 10 filled with heparinized saline) was inserted in the left jugular vein for injection of test compounds at 0.01 mg/kg (volume 1 mL/kg, 5-10 s) or 0.9% saline. Blood pressure was recorded each second for up to 900 seconds following intravenous injection. Changes in mean arterial blood pressure (Δ MABP) were determined from the basal pressure of rat. Data represents the mean±SEM of 3-5 rats for each condition.

Statistical Analysis

Figure 8A:
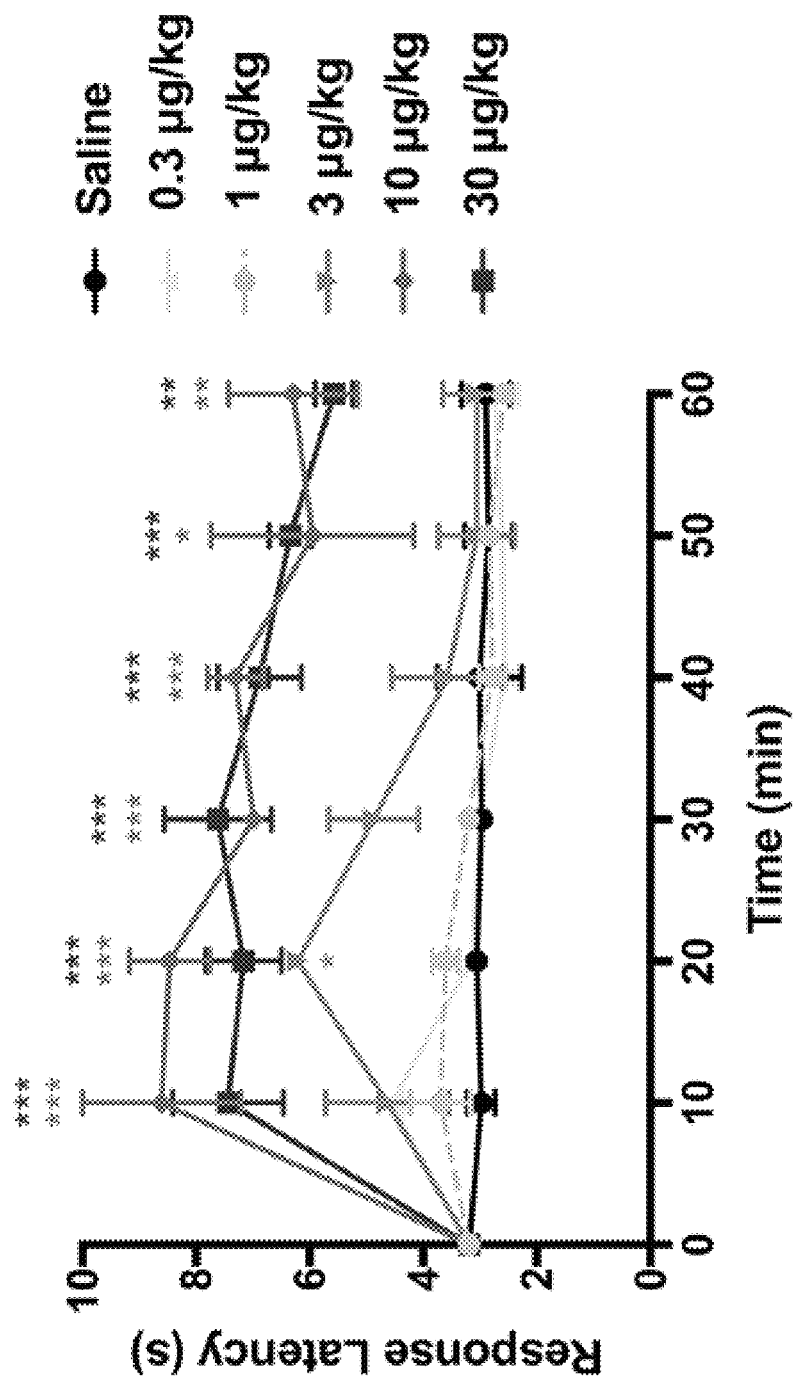
FIGS. 8A-F: Analgesic efficacy of neurotensinergic agonists on acute (tail-flick test) and tonic pain (formalin test).
Figure 8B:
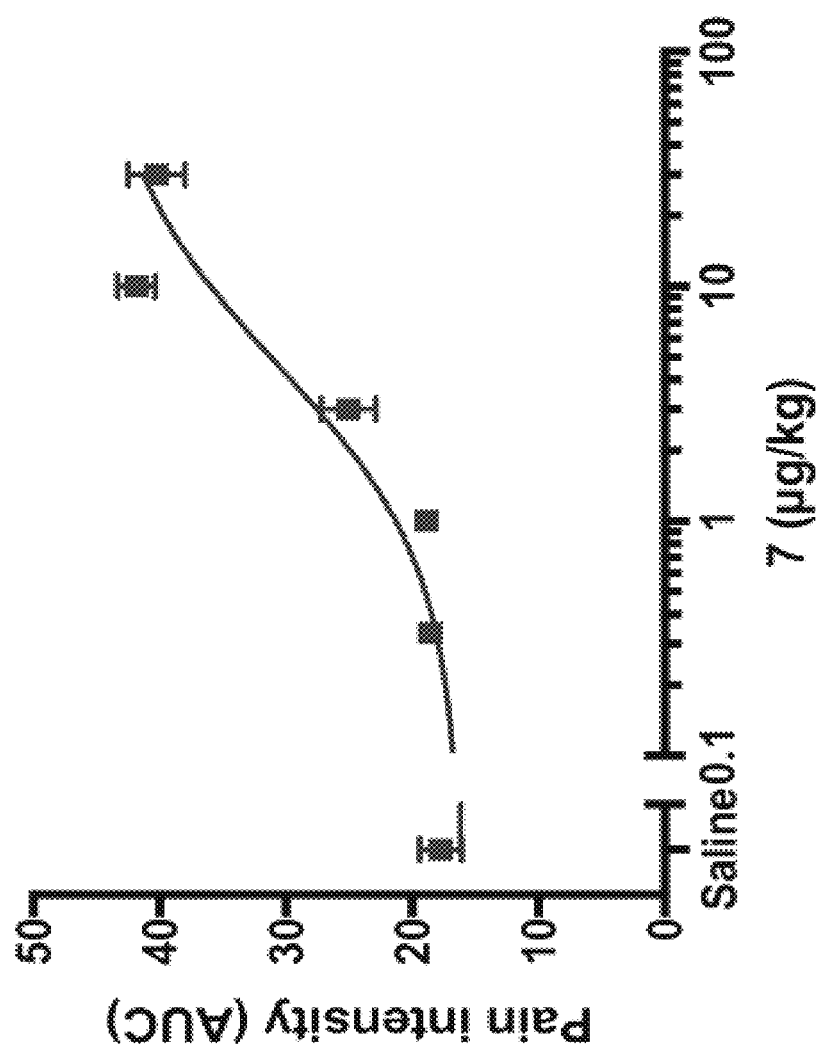
Figure 8C:
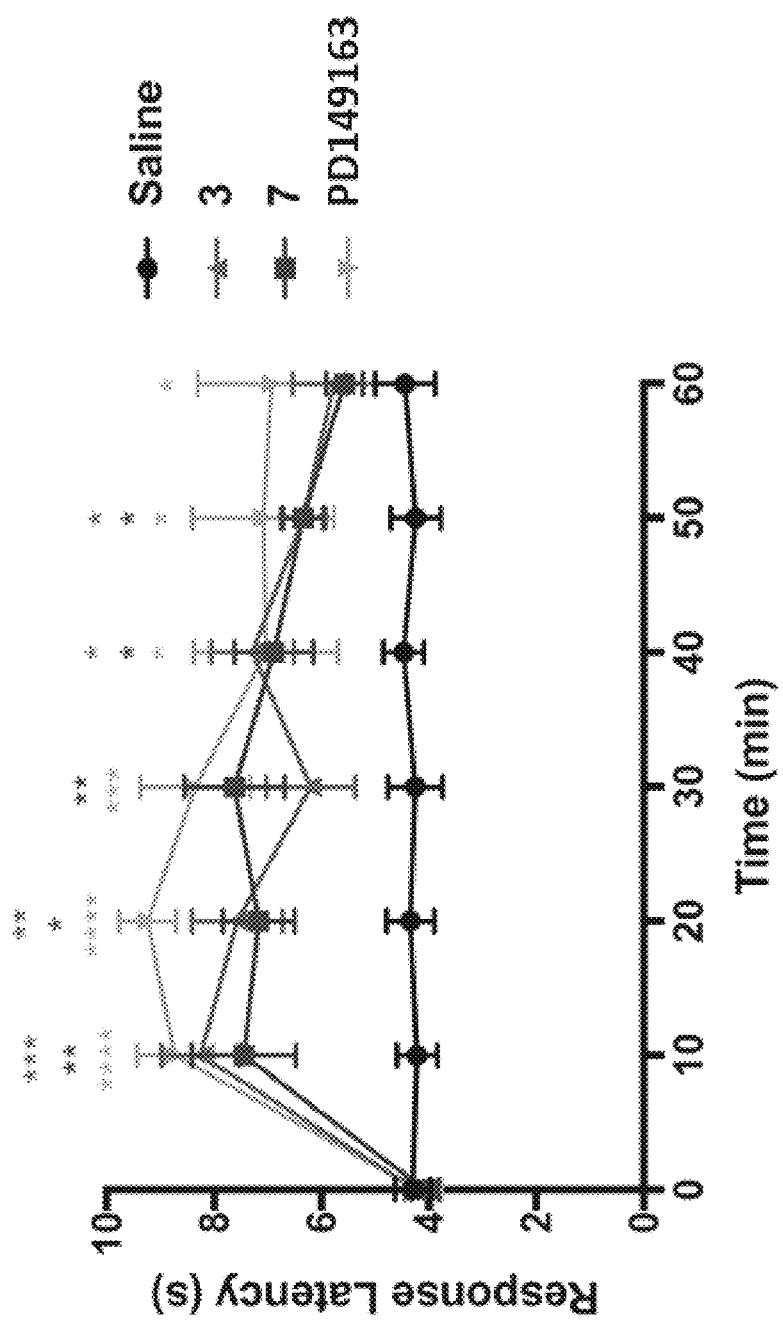

Data are expressed as mean±standard errors of the mean (SEM). All graphs and statistical analysis were performed using GraphPad Prism™ 7 (GraphPad software, La Jolla, Calif., USA). A two-way ANOVA followed by Tukey's multiple comparisons test was used to determine the significant differences in tail-flick latencies and changes in body temperature (Δ body temp) between different concentrations of compound 7 and saline (FIGS. 8A and 9A) or between drug and saline (FIG. 8C). The % MPE, the AUC for the formalin test and the Δ body temp at 60 min post-injection were analyzed using a one-way ANOVA followed by a Dunnett's multiple comparison test to compare drug and saline treatment. A difference in response was considered significant with p-values *p<0.05, p<0.01, and *p<0.001. To determine the half maximal effective dose ($ED_{50}$) of compound 7, the AUC was calculated for each concentration in tail-flick and hypothermia test. Then, ED values were determined using the dose-response-stimulation log(agonist) vs response (three parameters).

Example 2: Peptide Synthesis

The peptides were synthesized on a solid support as described above. Briefly, the first amino acid (side chain and amine alpha adequately protected) was loaded on the resin by simple substitution of chlorine by the carboxylic acid in the presence of a base. The alpha amine was then deprotected as described above in order to be able to couple the following amino acid with a coupling agent. The deprotection/coupling reactions were then repeated as described above until the complete peptide is obtained (See FIG. 1).

Figure 2:
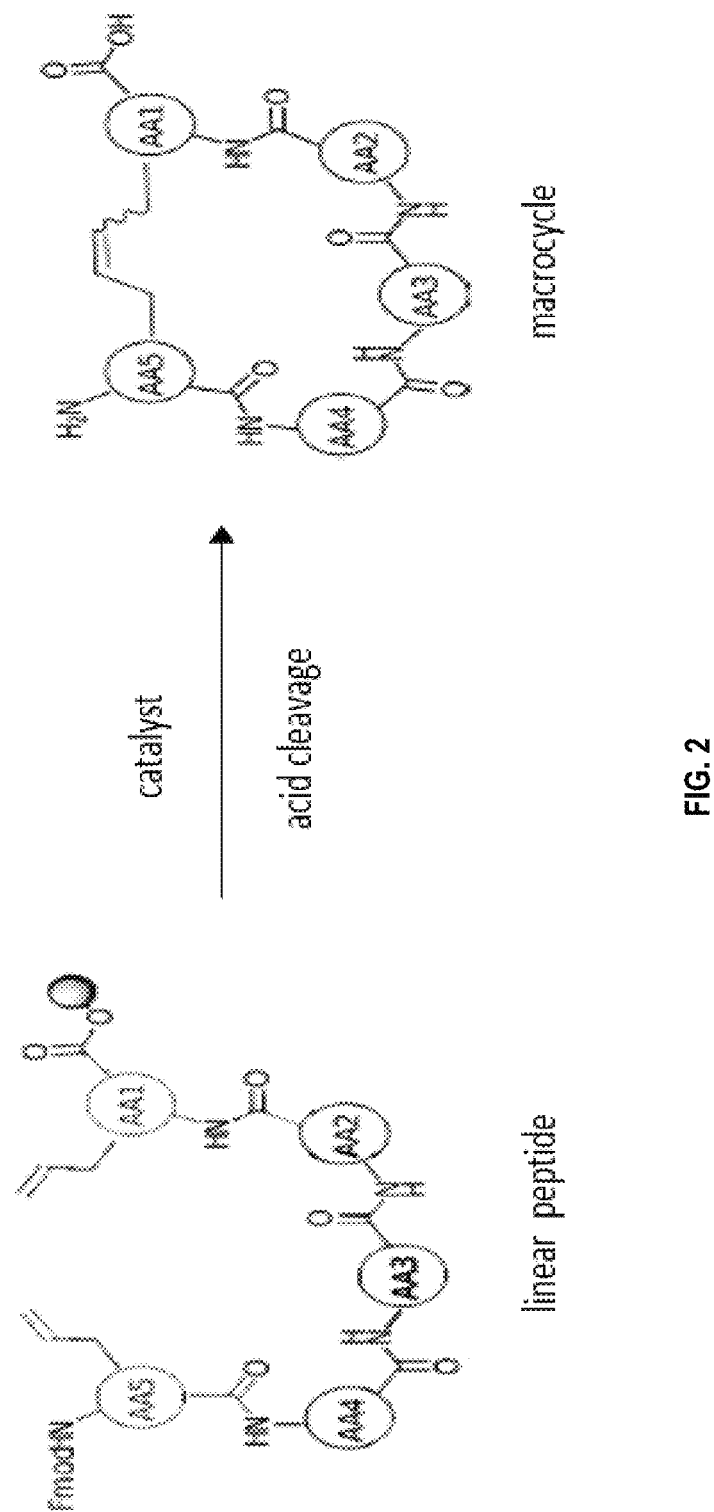
FIG. 2: Schematic peptide macrocyclization using ring-closing metathesis.

The macrocyclisation of the peptides was carried out by metathesis of the olefins. This reaction requires the introduction, during the peptide synthesis, of two non-natural amino acids each having an alkene group (carbon-carbon double bond). In the presence of a catalyst (see below), the two alkene groups will react together to form a single carbon-carbon double bond, and thus close the ring. The macrocyclic peptide was then cleaved from the resin at the same time as the side chain protective groups of the amino acids are removed by acid treatment. The macrocycle was purified by preparative HPLC (see FIG. 2).

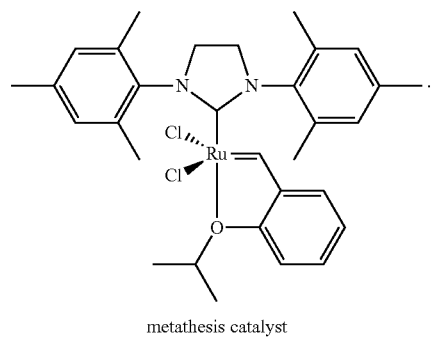

metathesis catalyst

Example 3: Synthesis of Fmoc-Tyr-o-Allyl-OH

Figure 4:
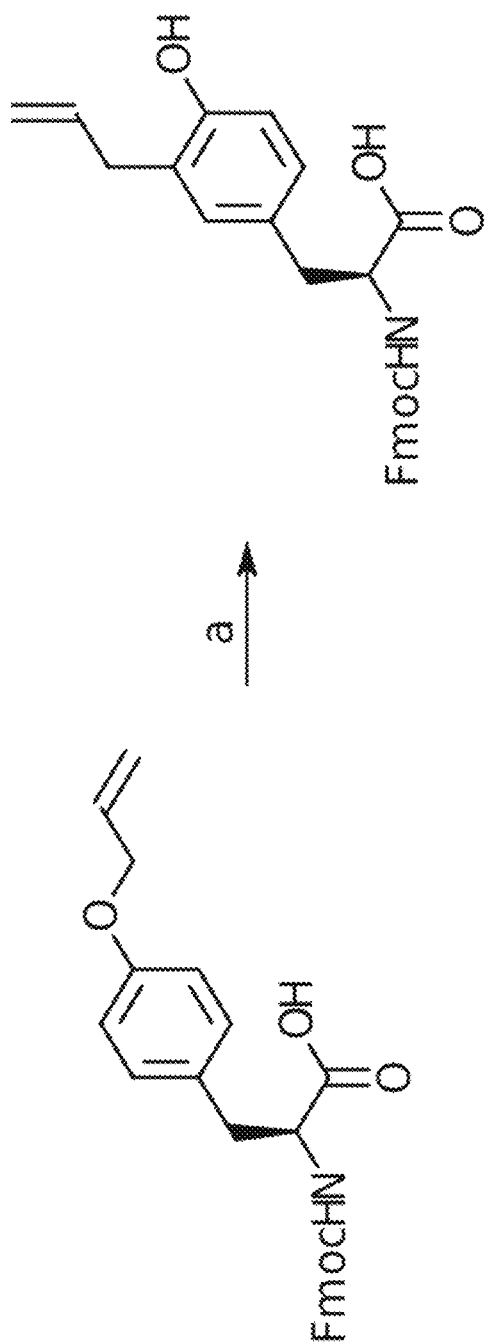
FIG. 4: Synthesis of Fluorenylmethoxycarbonyl (Fmoc) o-allyl tyrosine from commercial O-allyl tyrosine (for further clarity, o- means attachment on the carbon atom located in the ortho position of the tyrosine phenol group, while O-denotes attachment on the oxygen atom) to achieve Claisen Rearrangement wherein "a" is suspension in 40 mL of anhydrous toluene under argon atmosphere at 0° C. and addition of Diethylaluminum chloride ($Et_2AlCl$).

The procedure was adapted from Naruta 1986. Fmoc-Tyr (O-Allyl)-OH (5 g, 11.3 mmol) synthesized as described in FIG. 4 was suspended in 40 mL of anhydrous toluene under argon atmosphere at 0° C. Diethylaluminum chloride (12.7 mL of 1.8 mol/L solution in toluene, 2 eq) was added. The reaction was stirred at room temperature then quenched at 0° C. by addition of 25 mL of 6N HCl. The organic phase was washed with brine, dried over $MgSO_4$, filtered and evaporated. The product and the remaining of the starting material were separated by flash chromatography. The product was then solubilized in water/acetonitrile 50:50 and lyophilized to give 1.5 g of the desired product (30% yield). See FIG. 4. $^1$H NMR (CDCl$_3$/CD$_3$OD 9:1, 400 MHz): δ 2.94 (dd, J=6.51, 14.11 Hz, 1H), 3.03 (dd, J=5.31, 14.11 Hz, 1H), 3.28 (d, J=6.58 Hz, 2H), 3.47 (br, 4H), 4.13 (t, J=7.14 Hz, 1H), 4.29 (m, 2H), 4.49 (t, J=5.92 Hz, 1H), 4.96 (t, J=1.43 Hz, 1H), 5.0 (dq, J=1.74, 6.61 Hz, 1H), 5.92 (m, 1H), 6.65 (d, J=8.12 Hz, 1H), 6.81 (dd, J=8.12, 1.94 Hz, 1H), 6.85 (d, J=1.94 Hz, 1H), 7.24 (t, J=7.41 Hz, 2H), 7.33 (t, J=7.53 Hz, 2H), 7.5 (t, J=7.0 Hz, 2H), 7.7 (d, J=7.55 Hz, 2H). $^{13}$C NMR (CDCl$_3$/CD$_3$OD 9:1, 400 MHz): δ 34.28, 37.14, 47.16, 49.37, 54.86, 67.07, 115.36, 115.65, 120.0, 125.13, 126.32, 127.12, 127.76, 128.24, 131.23, 136.78, 141.30, 143.80, 153.55, 173.83.

Example 4: Synthesis of Fmoc-aminohex-6-enoic Acid (for Compound 6)

The procedure was adapted from Li, 2017. aminohex-6-enoic acid (1 g, 7.5 mmol) was dissolved into 20 mL of water. Sodium bicarbonate (1.3 g, 15.2 mmol) was added. Fmoc-Cl (2.3 g, 9.1 mmol) was dissolved into 15 mL of dioxane and this solution was added to the mixture. After 4 h stirring, the dioxane was evaporated under reduced pressure and the aqueous phase was washed with diethyl ether. Its pH was then adjusted to 2 by addition of 1N HCl and the product was extracted with ethyl acetate. The organic phase was washed with brine, dried over MgSO$_4$, filtered and evaporated under reduced pressure. The product was purified by flash chromatography (72% yield). $^1$H NMR (CDCl$_3$, 400 MHz): δ 1.35 (dt, J=14.67, 7.44, 2H), 1.51 (dt, J=14.63, 7.34, 2H), 1.64 (dt, J=14.89, 7.54 Hz, 2H), 2.34 (t, J=7.28 Hz, 2H), 3.18 (q, J=6.51 Hz, 2H), 4.19 (t, J=6.88 Hz, 1H), 4.39 (d, J=6.92 Hz, 1H), 7.29 (t, J=7.45 Hz, 2H), 7.38 (t, J=7.53 Hz, 2H), 7.57 (d, J=7.23 Hz, 2H), 7.74 (d, J=7.58 Hz, 2H). $^{13}$C NMR (CDCl$_3$, 400 MHz): δ 24.09, 25.94, 29.46, 33.40, 40.62, 47.14, 66.35, 119.81. 124.86, 126.86, 127.5, 141.17, 143.82, 177.73.

Example 5: Synthesis of Compounds Cyclized Via N-Terminal Octenylalanine or Nonenoic Acid (Compounds 1, 3 and 11)

The compounds having an N-terminal amino acid that did not require alkylation prior to cyclization were synthetized as follows: following the coupling of the last amino acid, the hydroxy group of the tyrosine was protected by acylation. The Ring-Closing Metathesis was carded out and then the acyl and/or Fmoc groups were removed by treatment with piperidine.

Example 6: Synthesis of Compounds Cyclized Via N-Terminal Lysine, Ornithine, Diaminobutyric Acid, Diaminopropionic Acid or Aminohex-6-Enoic Acid Side Chain (Compounds 2 and 4-10)

Figure 5:
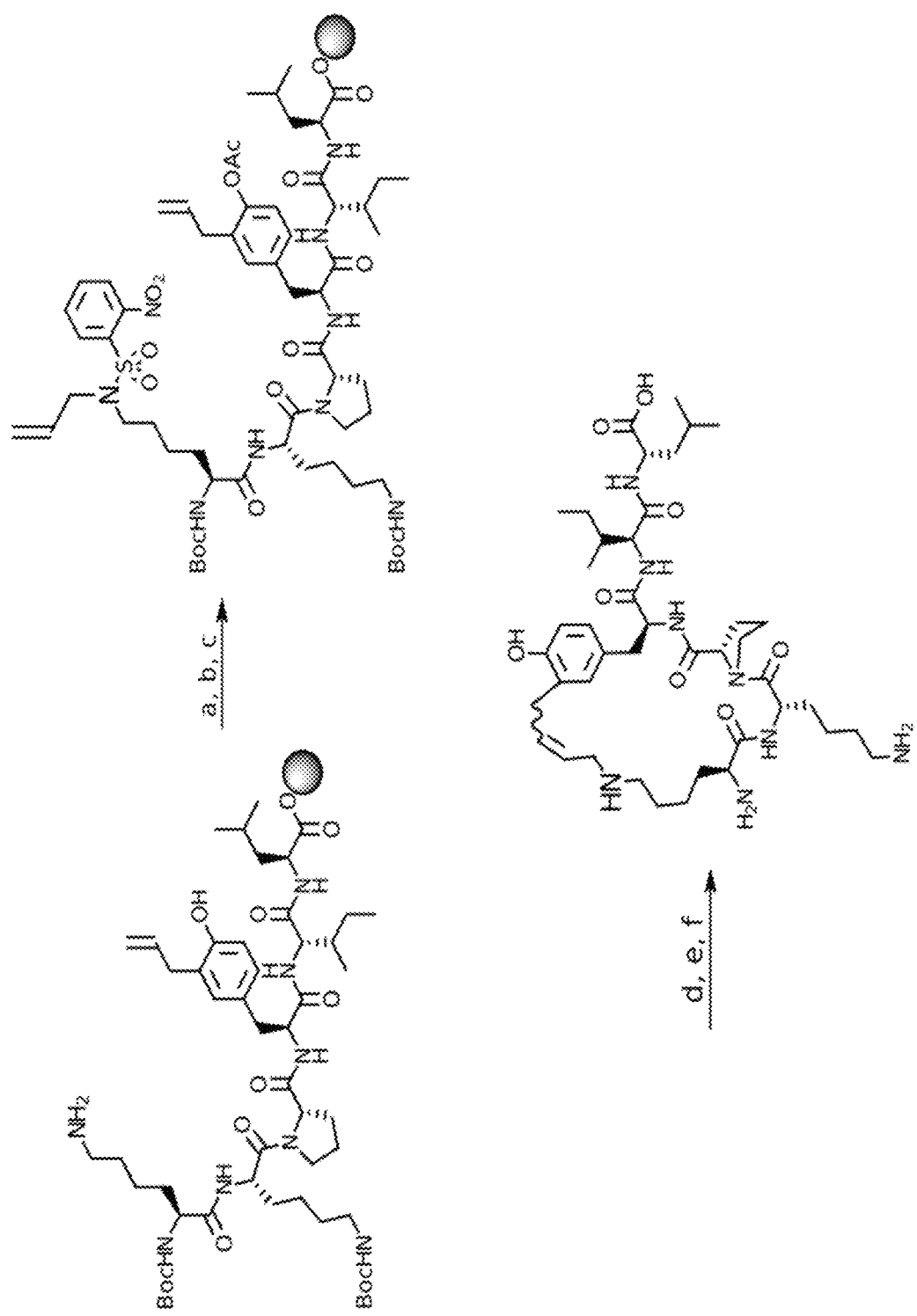
FIG. 5: Macrocyclization of compound 2. (a) Nosyl-Cl (4 eq.), Collidine (10 eq.), NMP, rt, 2×30 min; (b) $Ac_2O$ (Acetic anhydride) (2 eq), DIEA (diisopropylethylamine) (2 eq), DCM (dichloromethane), rt, 2×1 h; (c) Allyl-OH (10 eq.), $PPh_3$ (triphenylphosphine) (5 eq.), DIAD (Diisopropyl azodicarboxylate) (5 eq.), THF, rt, 2×30 min; (d) Hoveyda-Grubbs $2^{nd}$ generation catalyst (0.2 eq.), p-benzoquinone (1 eq.), DCE (1,2-dichloroethane), 50° C., 1 h; (e) 2-mercaptoethanol (10 eq.), DBU (1,8-diazabicyclo(5.4.0)undec-7-ene) (5 eq.), NMP (N-Methyl-2-pyrrolidone), rt, 2×30 min; (f) TFA (trifluoroacetic acid)/DCM/TiS, rt, 1 h.

The compounds having an amino acid of the lysine type involved in the macrocyclization have been synthesized as shown in FIG. 5. The peptide synthesis on solid support was carried out first, then the amine of the lateral chain of lysine was activated by the introduction of a nosyl (2-nitrobenzenesulfonyl) group. This nosyl group permits the alkylation of the amine by Fukuyama-Mitsunobu reaction after protecting the hydroxy group of the tyrosine by acylcation. The Ring-Closing Metathesis was carried out and then the nosyl group and acyl were removed by treatment in the presence of a base and of 2-mercaptoethanol. Compound 5 was prepared similarly except that at the last step, the acyl group was removed by treatment with piperidine. Other compounds in Table I were synthesized using the same methodology.

Compounds 1-15 are presented in Table I below.

TABLE I structures of compounds NT 8-13 and 1-15

| Code | Structure |
|---|---|
| NT 8-13 RRPYIL (SEQ ID NO: 1) | 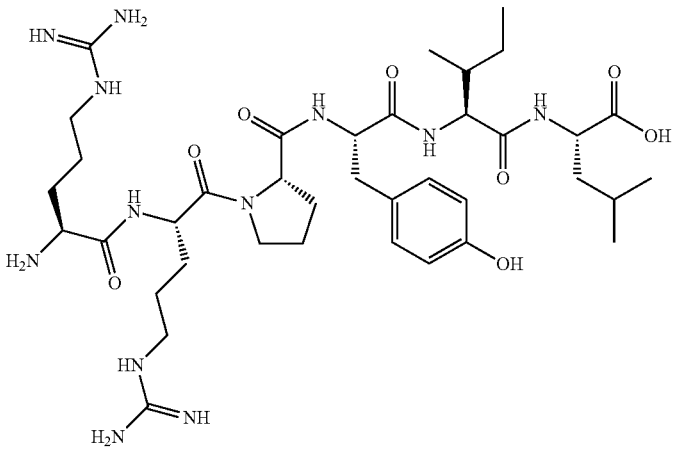 [SMILES: CCC(C)[C@H](NC(=O)[C@H](Cc1ccc(O)cc1)NC(=O)[C@@H]1CCCN1C(=O)[C@H](CCCNC(=N)N)NC(=O)[C@@H](N)CCCNC(=N)N)C(=O)N[C@@H](CC(C)C)C(=O)O] |

TABLE I-continued structures of compounds NT 8-13 and 1-15

| Code | Structure |
|---|---|
| 1-L<br>nonenoic acid KPY(All)IL<br>(SEQ ID NO: 27) | 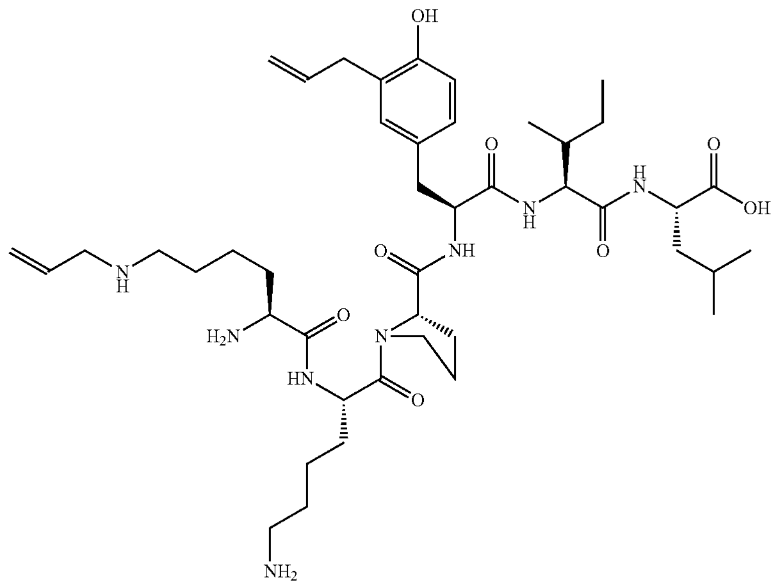 |
| 1-M (or 1)<br>c[nonenoic acid KPY(All)]IL<br>(SEQ ID NO: 27) | 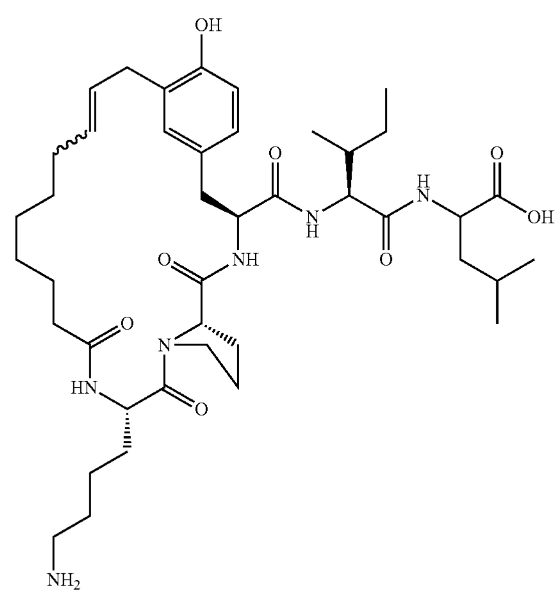 |

TABLE I-continued
structures of compounds NT 8-13 and 1-15
| Code | Structure |
|---|---|
| 2-L<br>K(All)KPY(All)IL<br>(SEQ ID NO: 14) | 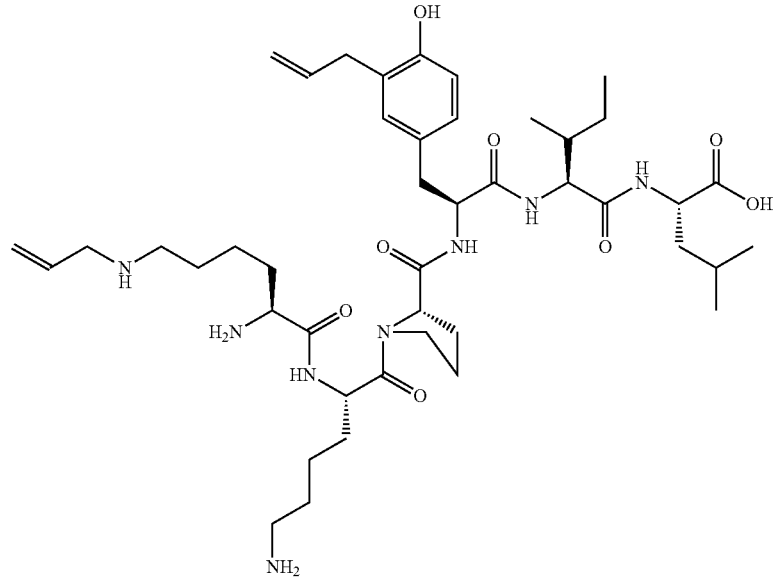 |
| 2-M (or 2)<br>c[K(All)KPY(All)]IL<br>(SEQ ID NO: 14)<br>(diastereoisomer of compound 4) | 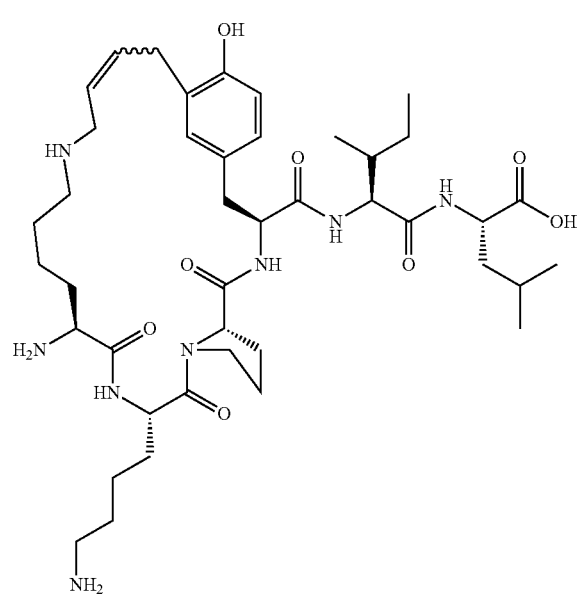 |

TABLE I-continued structures of compounds NT 8-13 and 1-15

| Code | Structure |
|---|---|
| 6<br>c[aminohex-6-enoic acid(All)KPY(All)]IL<br>(SEQ ID NO: 29) | 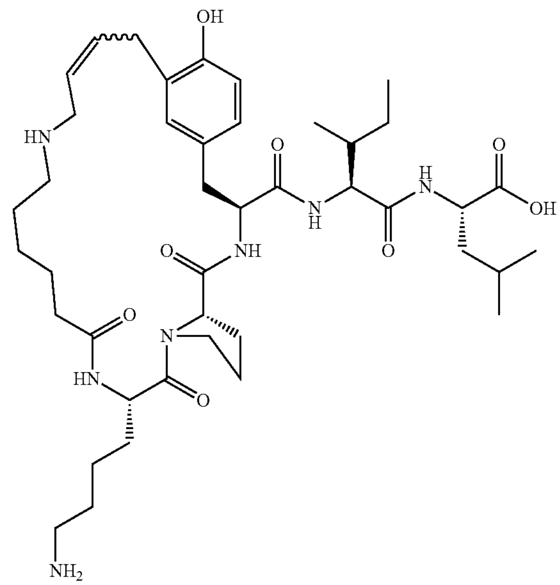 |
| 5<br>c[K(All)(S(O)₂(o-nitrophenyl))KPY(All)]IL<br>(SEQ ID NO: 34) | |

TABLE I-continued
structures of compounds NT 8-13 and 1-15
| Code | Structure |
|---|---|
| 4<br>c[K(All)KPY(All)]IL<br>(SEQ ID NO: 14)<br>(diastereoisomer of compound 2) | 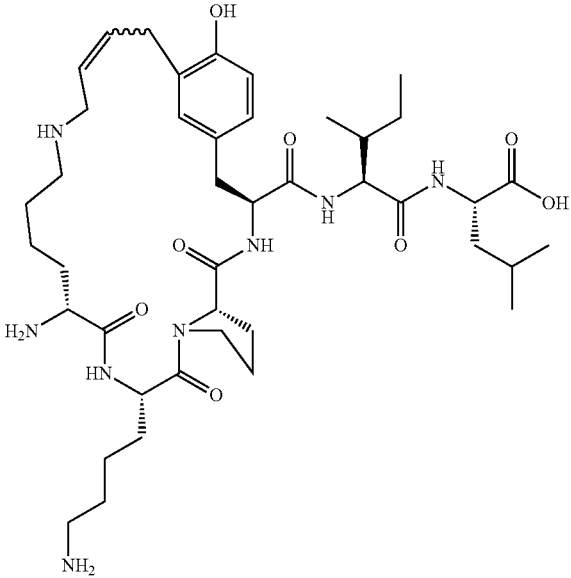 |
| 3<br>c[OctenylAKPY(All)]IL<br>(SEQ ID NO: 33)<br>(diastereoisomer of compound 12) | 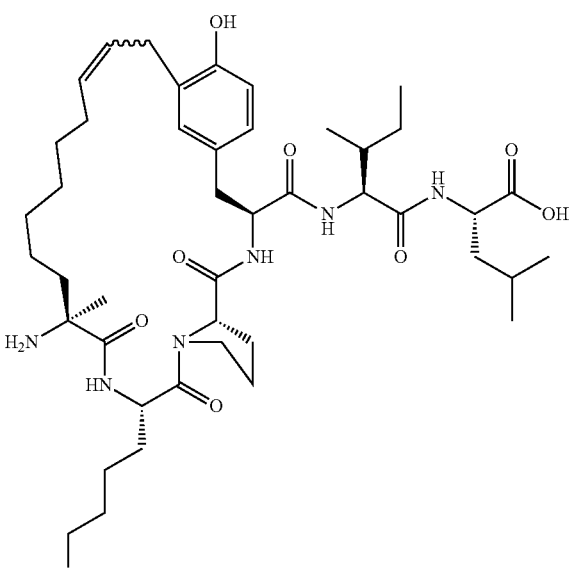 |

TABLE I-continued structures of compounds NT 8-13 and 1-15

| Code | Structure |
|------|-----------|
| 7<br>c[Orn(All)KPY(All)]IL<br>(SEQ ID NO: 18) | 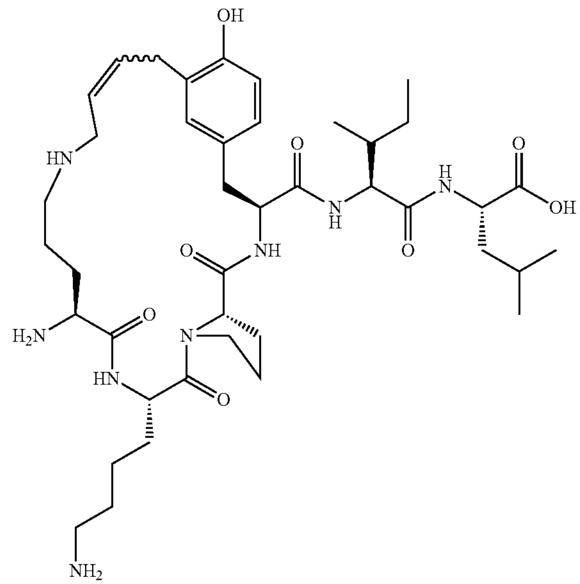 |
| 8<br>c[Dab(All)KPY(All)]IL<br>(SEQ ID NO: 22) | 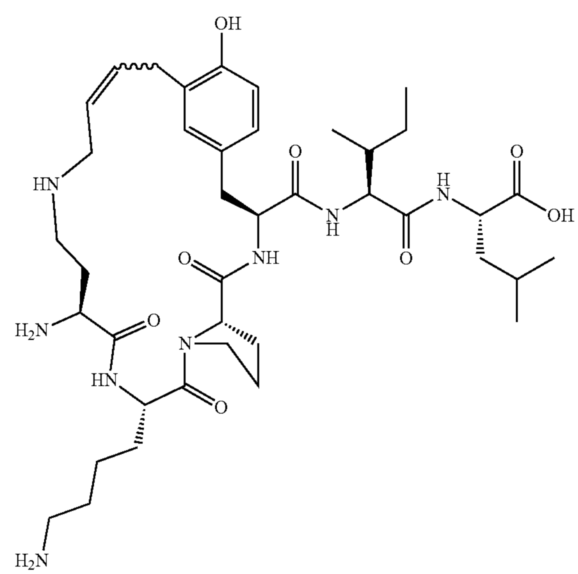 |

TABLE I-continued
structures of compounds NT 8-13 and 1-15
| Code | Structure |
|---|---|
| 9<br>c[K(butenyl)KPY(All)]IL<br>(SEQ ID NO: 15) | 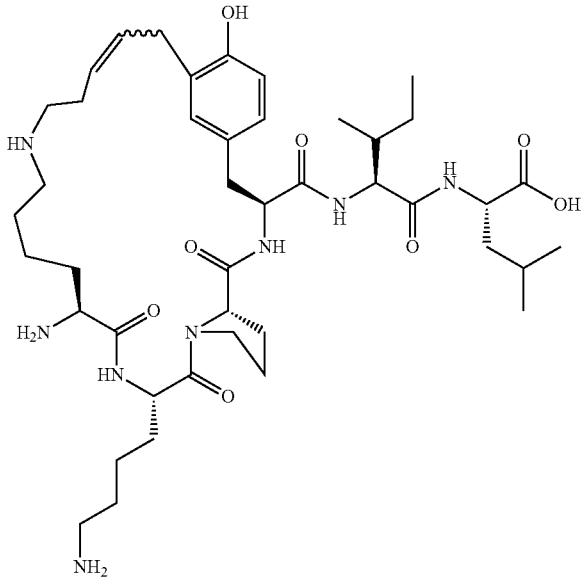 |
| 10<br>c[K(pentenyl)KPY(All)]IL<br>(SEQ ID NO: 16) | 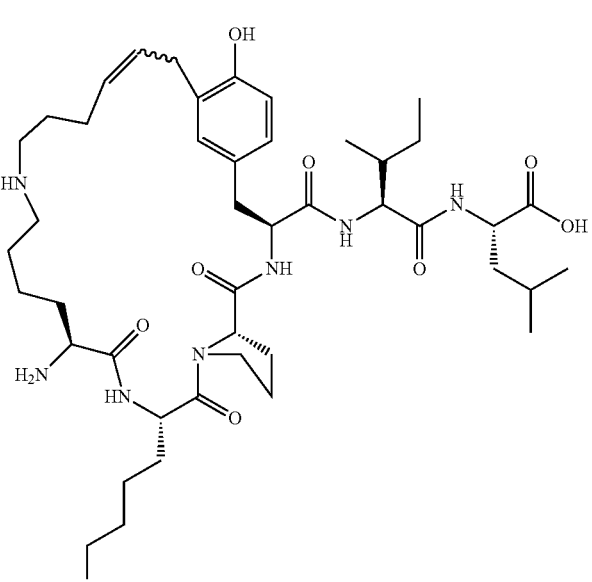 |

TABLE I-continued structures of compounds NT 8-13 and 1-15

| Code | Structure |
|---|---|
| 11<br>c[nonenoic acid-RPY(All)]IL<br>(SEQ ID NO: 31) | 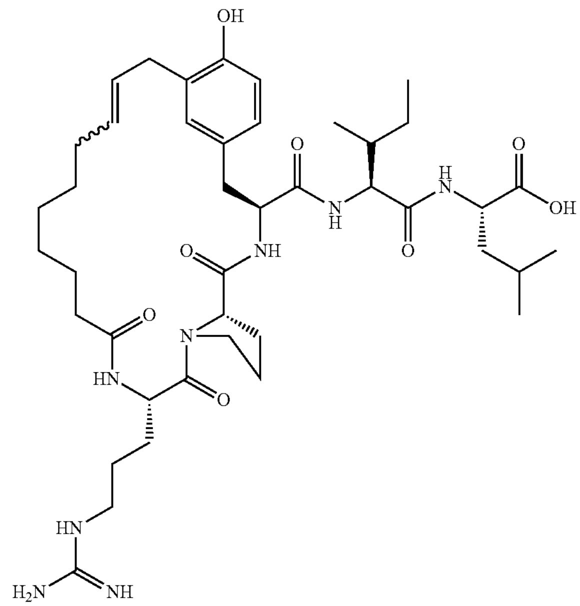 |
| 12<br>c[OctenylAKPY(All)]IL<br>(SEQ ID NO: 33)<br>(diastereoisomer of compound 3) | 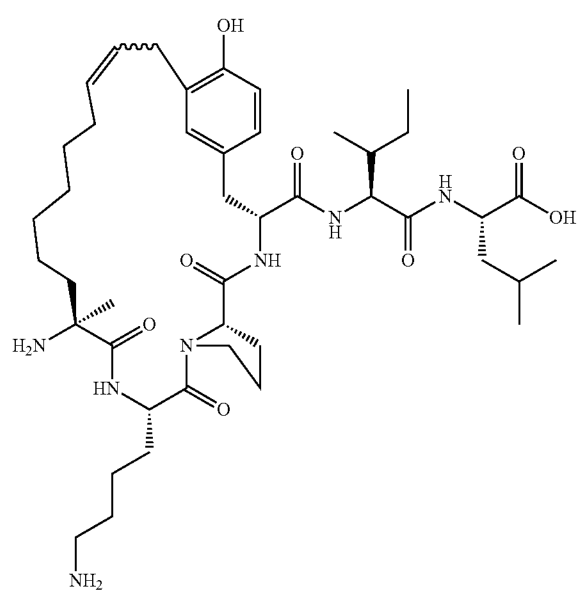 |

TABLE I-continued structures of compounds NT 8-13 and 1-15

| Code | Structure |
|---|---|
| 13<br>c[Dab(butenyl)KPY(All)]IL<br>(SEQ ID NO: 23) | 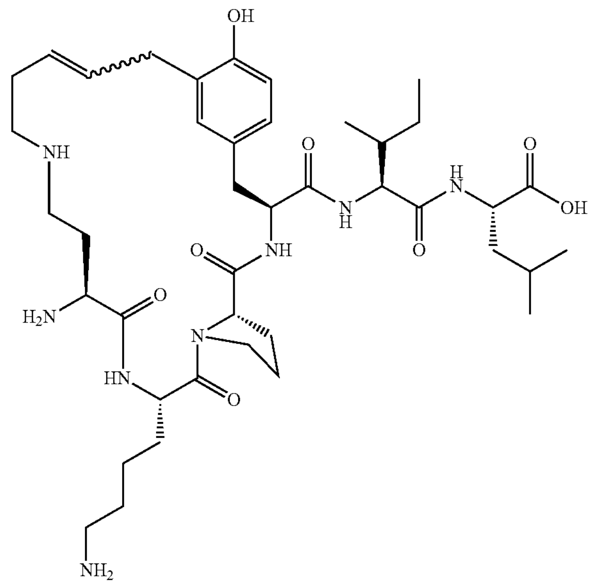 |
| 14<br>c[Dap(pentenyl)KPY(All)]IL<br>(SEQ ID NO: 25) | 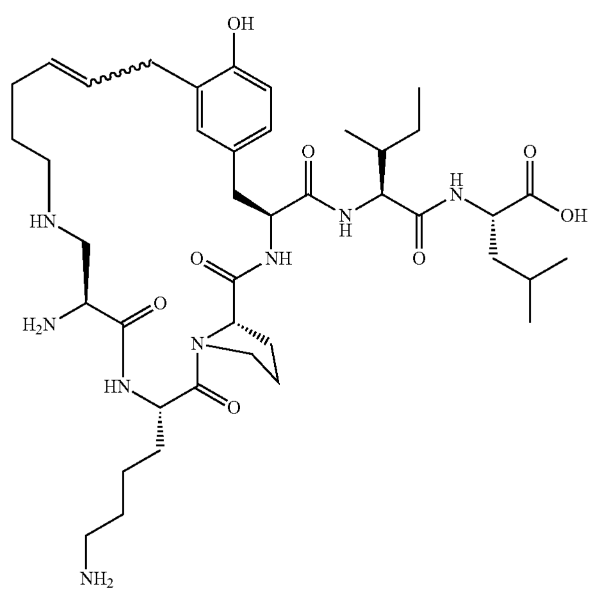 |

TABLE I-continued structures of compounds NT 8-13 and 1-15

| Code | Structure |
|---|---|
| 15<br>c[Orn(All)HPY(All)]IL<br>(SEQ ID NO: 19) | 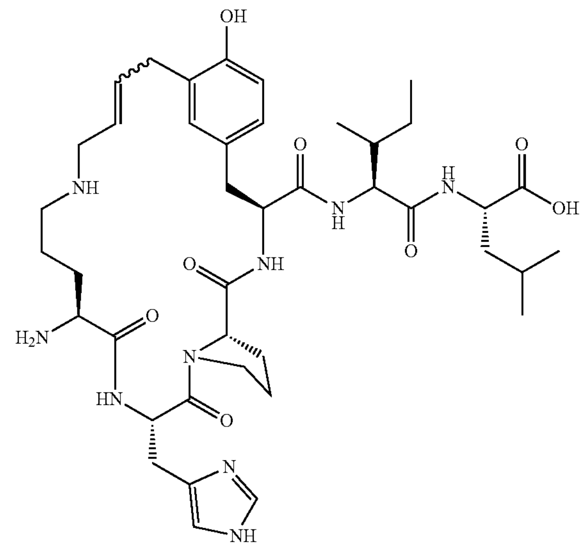 |

All: Allyl
Tle: Tert-Leucine
Nle: Norleucine
Nva: NorValine
Chg: CyclohexylGlycine
Cha: CyclohexylAlanine Example 7: Chemical Characterization of Compounds 1 to 15

The purity, ionization state ultra-performance liquid chromatography mass spectrometry (UPLC-MS) in terms of mass-to-charge ratio m/z, and theoretical mass were determined for compounds 1 to 15 and high-resolution mass spectrometry (HRMS) was determined for compounds 1-11 and are presented in Table II below.

TABLE II

Compounds biochemical characterization

| # | purity | Ion | m/z (UPLC-MS) | Theoretical mass MW (g/mol) | HRMS |
|---|---|---|---|---|---|
| 1 | 99% | [M + H]+ | 783.9 | 783.5015 | 783.5023 |
| 2 | 96% | [M + 2H]2+ | 407.4 | 407.2653 | 407.2657 |
| 3 | 99% | [M + 2H]2+ | 413.9 | 413.7755 | 413.7770 |
| 4 | 99% | [M + 2H]2+ | 407.4 | 407.2653 | 407.2672 |
| 5 | 99% | [M + 2H]2+ | 500.0 | 499.7544 | 499.7563 |
| 6 | 97% | [M + 2H]2+ | 400.0 | 399.7598 | 399.7619 |
| 7 | 98% | [M + H]+ | 799.5 | 799.5076 | 799.5069 |
| 8 | 96% | [M + H]+ | 785.5 | 785.4920 | 785.4917 |
| 9 | 95% | [M + H]+ | 827.5 | 827.5389 | 827.5388 |
| 10 | 96% | [M + H]+ | 841.6 | 841.5546 | 841.5547 |
| 11 | 98% | [M + H]+ | 812.6 | 811 | |
| 12 | 98.00% | [M + 2]2+ | 414 | 826 | |
| 13 | 98% | [M + 2]2+ | 400.4 | 799.03 | |
| 14 | 94% | [M + 2]2+ | 400.4 | 799.03 | |
| 15 | 95% | [M + 2]2+ | 404.9 | 807.99 | |

Example 8: Binding Assays

All compounds of Table I were cyclized between allyl-tyrosine and the N-terminal amino acid, i.e. a non-natural analog of lysine. The affinity for the NTS1 receptor was evaluated (see Table III).

The affinity for the NTS2 receptor (in a single dose except for compound 2) and the ability to activate the NTS2 receptor were also determined for certain compounds. These experiments allowed to determine that this series of macrocycles was non-selective i.e. able to bind to the NTS1 receptor as well as to the NTS2 receptor.

The compounds 7 to 10 have the same functional groups as compound 2 but a different cycle size. The inventors determined that the optimal size for affinity with NTS1 is a 22- or 23-atom cycle (compounds 2 and 7, $IC_{50}$=26 nM and 13 nM, respectively). Decreasing further (compound 8) or increasing the size of the cycle (compounds 9 and 10) results in loss of affinity.

Functional Testing

NTS1 is capable of activating several signaling pathways, thus the activation of $G\alpha_q$, $G\alpha_{13}$, β-arrestin 1 and β-arrestin 2 pathways was monitored. The ability of compounds of the invention to activate the NTS1 receptor was assessed using Bioluminescence Resonance Energy Transfer (BRET)-based biosensors, reporting the dissociation of G proteins (Table III, column $EC_{50}$ Gq) and the recruitment of β-arrestins to the receptor (Table III, column $EC_{50}$ βarr). All the tested compounds are agonists of these two paths.

TABLE III

Affinity, potency, and stability results[a]

| Code | Binding affinity $K_i$ NTS1 (nM)[b] | NTS1 | | | | | NTS2 | | Plasma half-life[d] |
|---|---|---|---|---|---|---|---|---|---|
| | | $IC_{50}$ (nM) | $EC_{50}$ Gq (nM)[c] | $EC_{50}$ G13 (nM)[c] | $EC_{50}$ β-arr1 (nM)[c] | $EC_{50}$ β-arr2 (nM)[c] | $IC_{50}$ (nM) | % displ at 1 μM* | |
| NT 8-13 | 1.29 ± 0.3 | 0.7 ± 0.06 | 0.6 ± 0.06 | 0.4 ± 0.04 | 0.6 ± 0.05 | 0.6 ± 0.04 | 9 | 100% | 3 min |
| 1-L | >10000 | 1390 ± 185 | | | | | | | 4 h |
| 1 | 5600 ± 41 | 394 ± 41 | 166.2 ± 13 | 433 ± 32 | 1500 ± 159 | 1370 ± 126 | | —% | 12 h |
| 2-L | 191 ± 98 | 26 | | | | | 11.8 | 82% | 5 min |
| 2 | 43 ± 8 | 26 ± 1 | 30 ± 0.06 | 66 ± 0.05 | 52 ± 0.06 | 21 ± 0.05 | 51 ± 9 | | 19 min |
| 6 | 656 ± 100 | 500 ± 22 | 57 ± 0.06 | 239 ± 0.09 | 96 ± 0.07 | 96 ± 0.05 | 2300 | 93% | 24 h[e] |
| 5 | 328 ± 142 | 237 ± 29 | 74 ± 0.06 | 119 ± 0.08 | 63 ± 0.08 | 92 ± 0.05 | 510.5 | 96% | 1.4 h |
| 4 | 772 ± 200 | 500 ± 39 | 182 ± 0.06 | 287 ± 0.06 | 310 ± 0.09 | 201 ± 0.05 | 238.8 | 93% | 24 h[e] |
| 3 | 156 ± 43 | 132 ± 11 | 27 ± 0.04 | 54 ± 0.07 | 37 ± 0.1 | 28 ± 0.1 | 25.8 | 96% | 24 h[e] |
| 7 | 15 ± 2 | 13 ± 1 | 3 ± 0.05 | 11 ± 0.03 | 4.2 ± 0.04 | 3 ± 0.05 | 4.8 | 66% | 30 min |
| 8 | 155 ± 28 | 118 ± 8 | 18 ± 0.04 | 55 ± 0.04 | 35 ± 0.04 | 19 ± 0.04 | | 64% | 2.5 h |
| 9 | 305 ± 46 | 227 ± 8 | 15 ± 0.03 | 52 ± 0.04 | 24 ± 0.05 | 15 ± 0.04 | 47.2 | 104% | 15 min |
| 10 | 903 ± 135 | 765 ± 9 | 39 ± 0.03 | 138 ± 0.04 | 50 ± 0.04 | 24 ± 0.05 | 128.2 | 105% | 18 min |
| 11 | | 293 ± 12 | | | | | | 78% | |
| 12 | | >10000 | | | | | 1100 | | |

*% displacement at 1 μM: represents the relative amount of radiolabeled neurotensin displaced by a 1 μM macrocycle dose.
[a]Results are presented as the mean of three or more independent experiments ± SEM;
[b]affinity ($K_i$ Values) determined by competitive binding assay with $^{125}$I-[Tyr$^3$]NT as a radioligand, using CHO-K1 cell membranes stably expressing hNTS1. Pseudo-Hill Slope of concentration-displacement curves range from 0.29 to 0.81;
[c]potency values obtained in BRET-based experiments conducted in CHO-K1 cells transiently transfected with hNTS1 and BRET biosensors;
[d]plasma stability determined by incubation in rat plasma at 37° C.;
[e]24 h is the longest time tested. For these compounds, about 50% starting materials remained at that time.

Example 8: Plasma Stability

In order to determine whether macrocyclization had a positive effect on peptide degradation by proteases, the inventors determined the half-life in rat plasma of NT 8-13, of compound 1 and of the linear version of compound 2 (denoted as compound 2-L in Table II and obtained by the same synthesis but omitting the cyclization step).

Figure 6A:
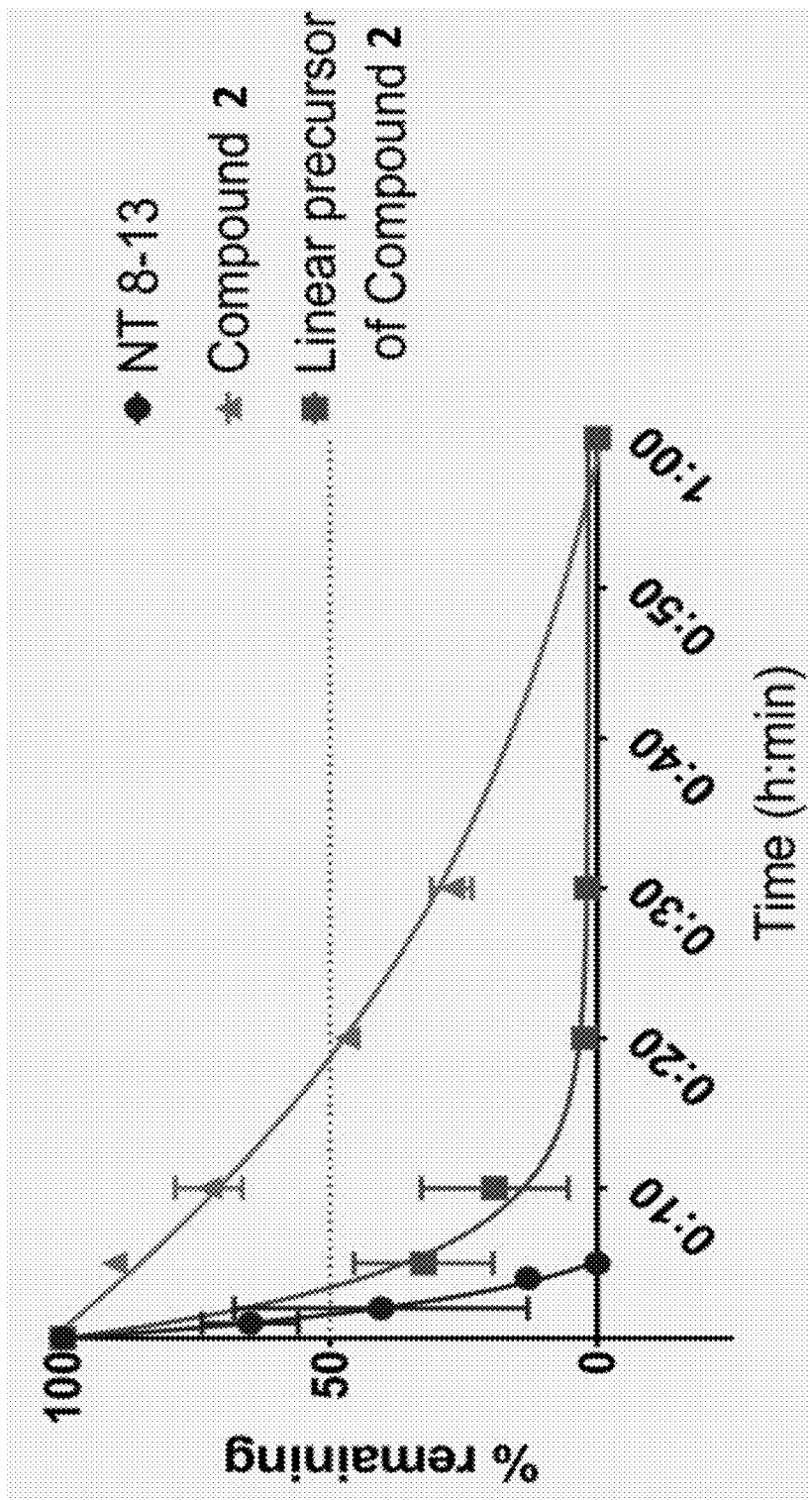
FIGS. 6A-B: Plasma half-life.
Figure 6B:
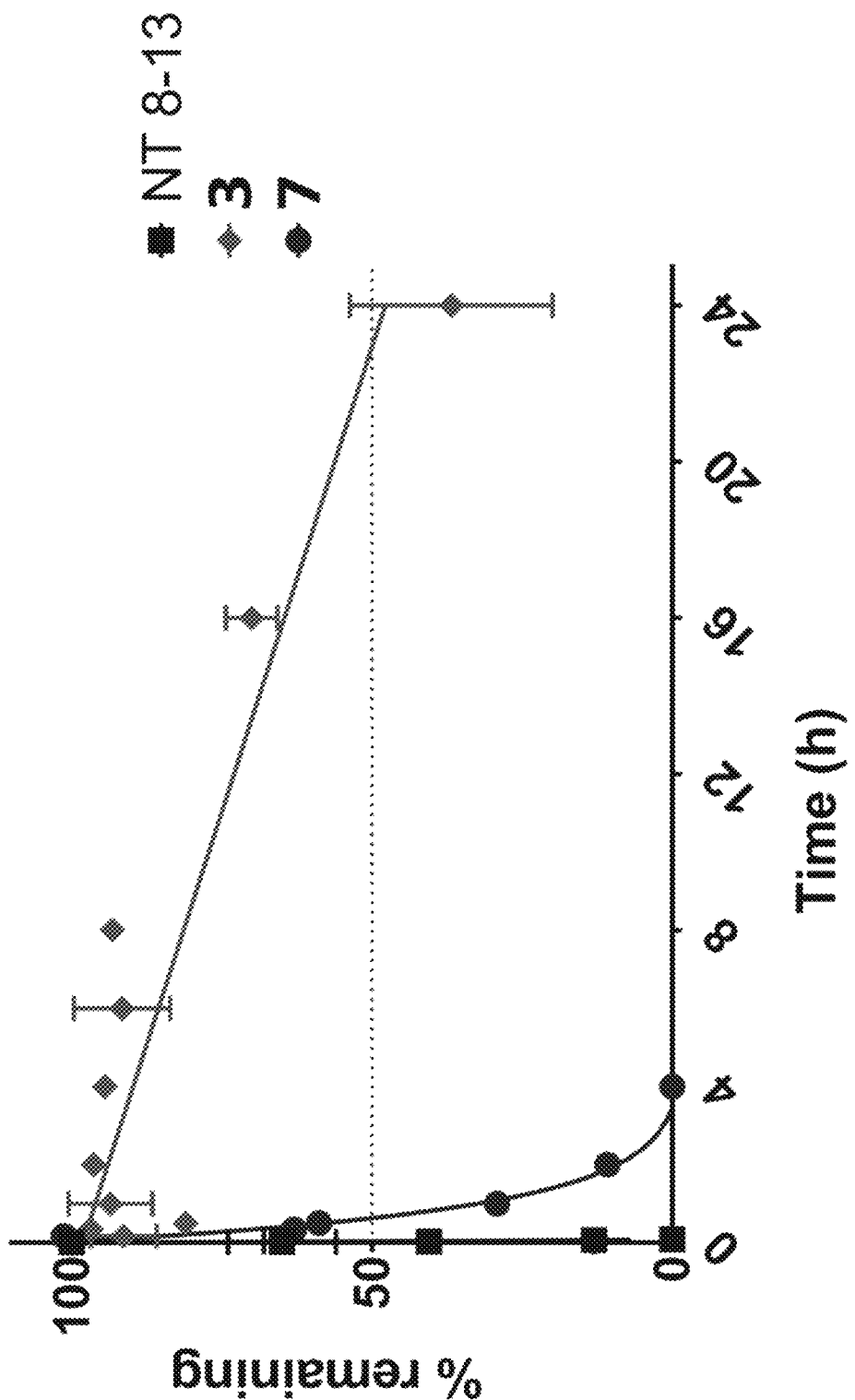

These results are reported in FIGS. 6A and B and in Table II, column "stability". Compound 2 not only possessed a greater plasma stability than NT (8-13) (t½ 19 min and 3 min, respectively), it was also more resistant than its linear counterpart 2-L (t½=5 min). The plasma half-life of the compound with the highest tested affinity was compared with that of the compound with the highest determined affinity/stability ratio i.e. compound 3. Results are present in FIG. 6B.

Example 9: Analgesic Profile In Vivo—Acute Pain and Tonic Model

Figure 7:
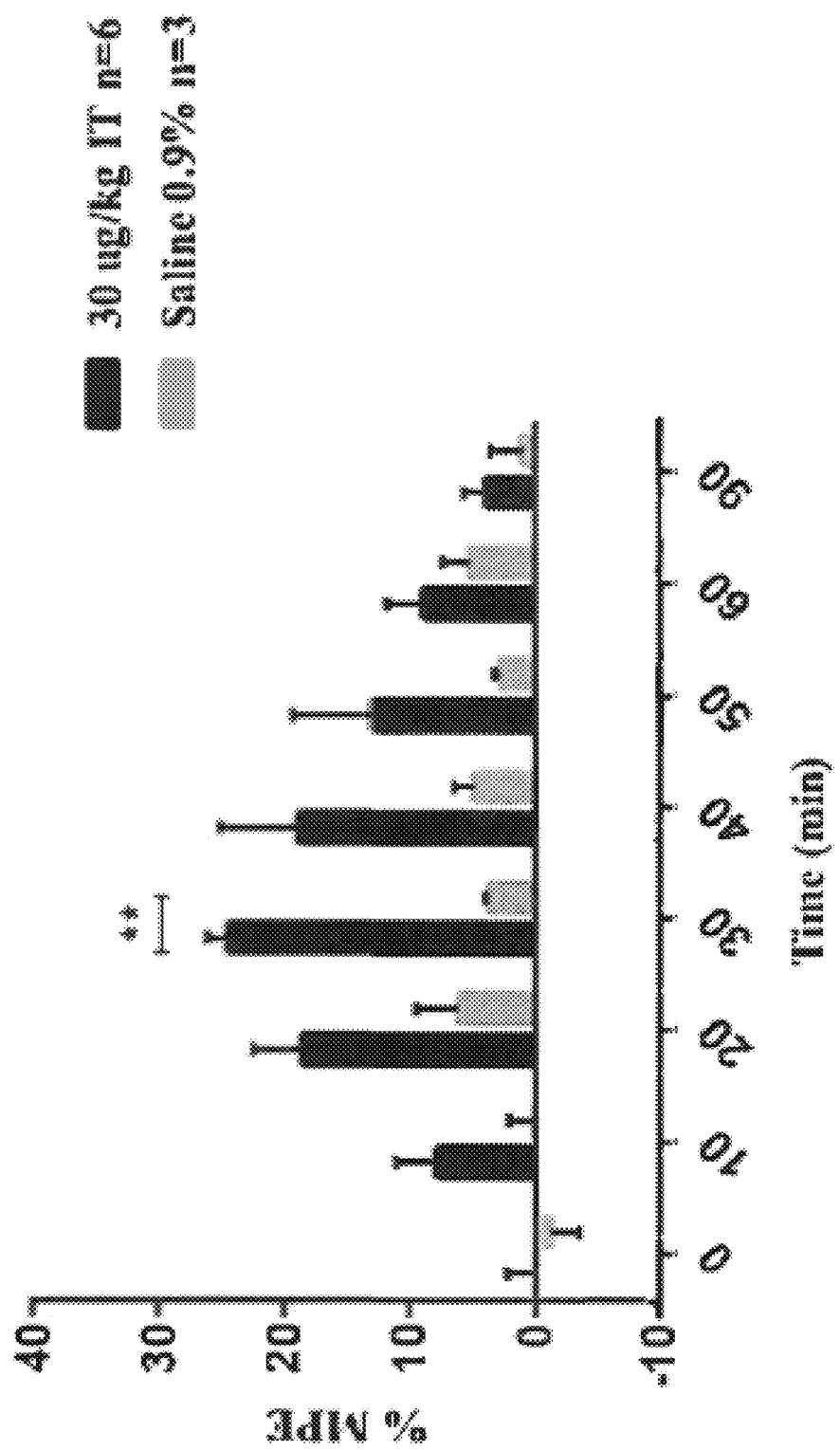
FIG. 7: Tail-flick test on rats injected intrathecally 30 μg/kg of compound 2.

Compound 2 was tested in an in vivo test of acute pain, the tail-flick test, in rats. Following an intrathecal injection at 30 μg/kg, the latency time observed was significantly increased compared to the saline injection, indicating the presence of an analgesic effect (FIG. 7 and Table IV). Representative macrocyclic compound 2 has a high affinity for NTS1 and NTS2 receptors, is able to activate NTS1 and induce a decrease in pain in the rat, in addition to having a half-life greater than the reference peptide (NT 8-13).

Compound 7, with the highest affinity and potency in functional assays and compound 3, with the highest stability, were also selected for further assessment in vivo.

The analgesic actions of compounds 3 and 7 were compared to those of reference compound H-Lys-[ψCH$_2$NH]-Lys-Pro-Trp-tertLeu-Leu-OEt (SEQ ID NO: 35) (PD149163), a linear analogue of NT (8-13) (Roussy, 2008).

First, the antinociceptive effects of compounds 3, 7 and PD149163 were tested in an acute nociception assay, measuring their ability to extend the response latency to thermal noxious stimuli in Sprague-Dawley rats. Upon intrathecal (i.t.) injection, compound 7 dose-dependently increased the latency of the tail-flick response (FIGS. 8A and B and Table IV), with $ED_{50}$ of 4.63 μg/kg. There was no apparent increase in latency for doses inferior to 1 μg/kg and the analgesic effect reached a plateau around 10 μg/kg.

Figure 8D:
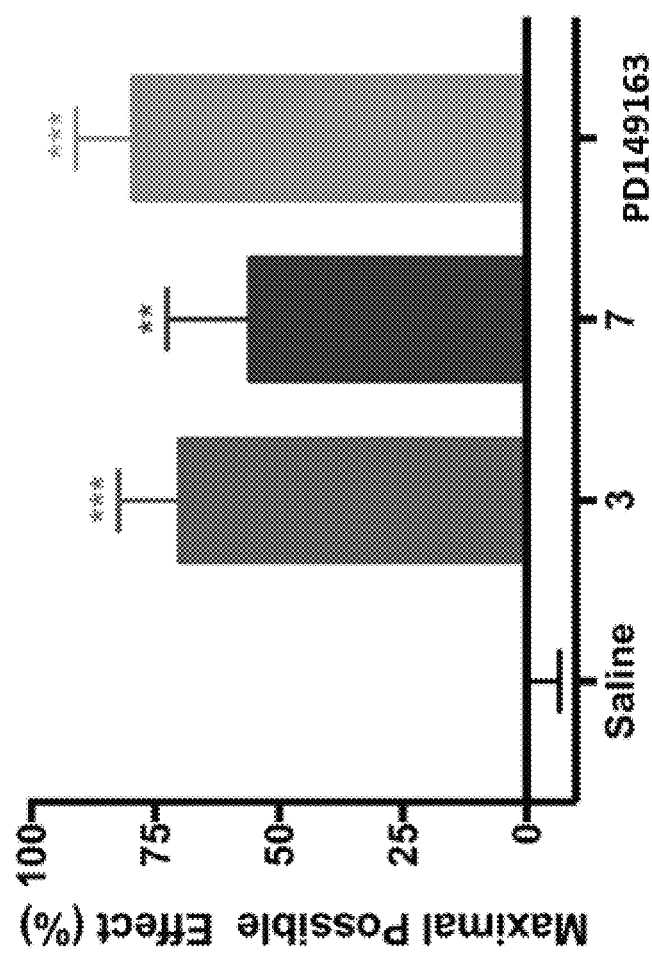

Comparison of the analgesic efficacy of compounds 3, 7 and PD149163 at 30 μg/kg (considered equivalent doses given the minor molecular weight differences between compounds) is shown in FIG. 8C. Both compounds 3 and 7 sustainably increased latency of the tail-flick reflex compared to baseline after i.t. injection. The fact that the major difference in stability between the two compounds is not reflected here can tentatively be attributed to the central injection used for this assay, which bypasses the encounter with plasma proteases. Maximal possible effects (MPE, FIG. 8D) of compounds 3 and 7 were 70% and 50%, respectively, which is comparable to the analgesic action of the previously reported PD149163 (MPE 75%).

Figure 8E:
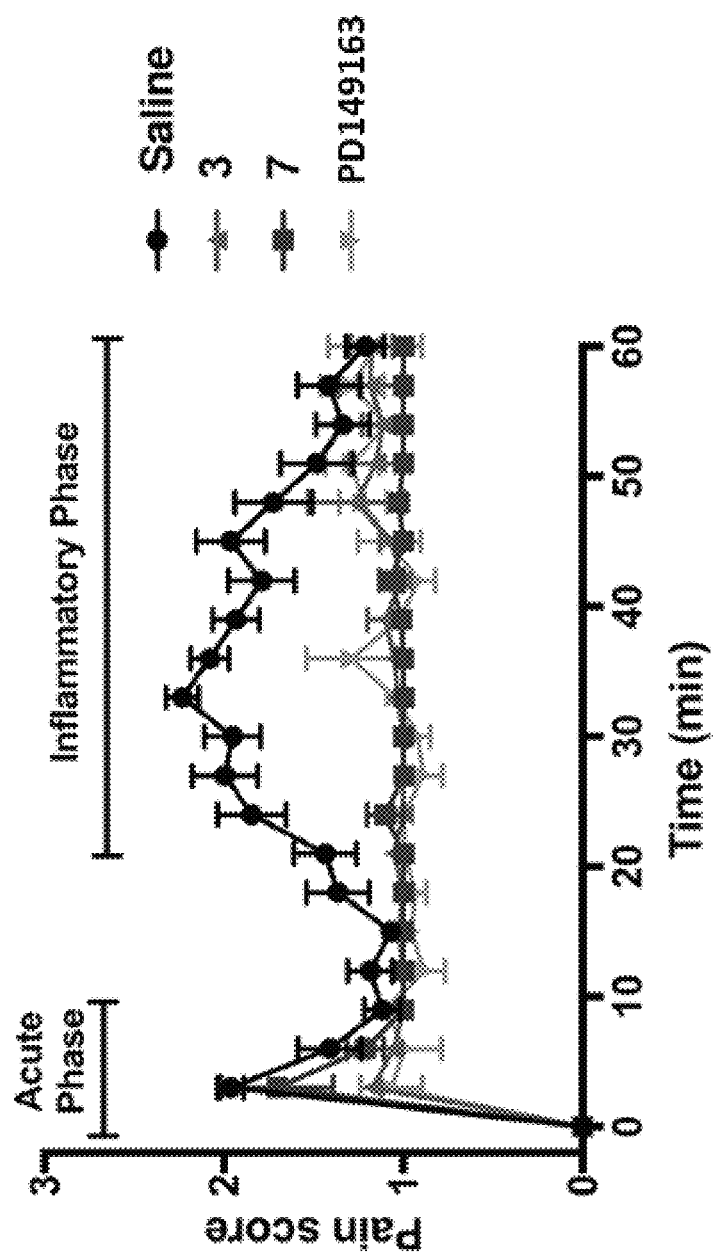
Figure 8F:
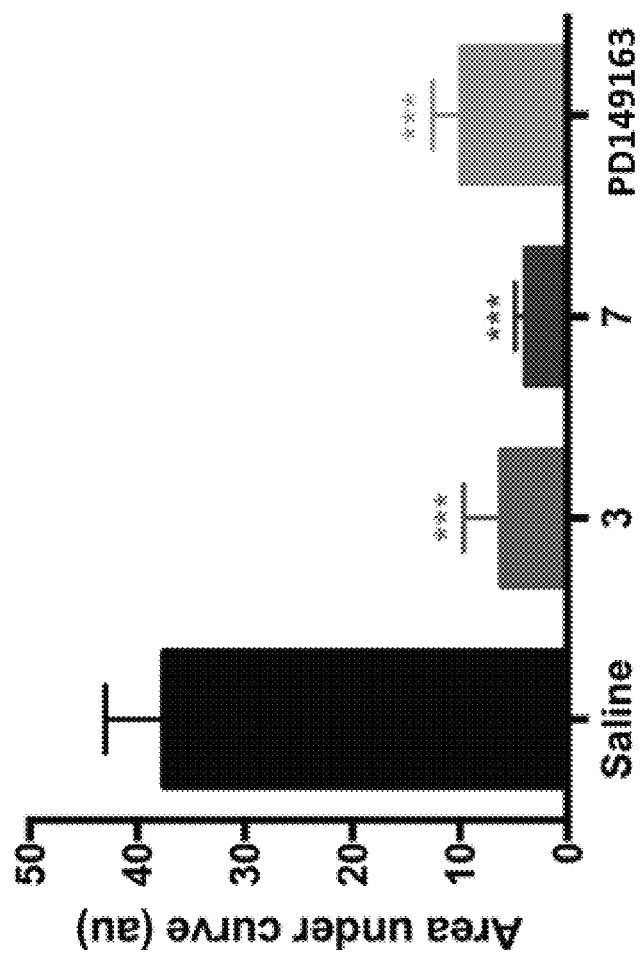

The compounds were also tested in the formalin tonic pain model. In this test, formalin was injected into the rat right hind paw. When treated i.t. with saline, the formalin typically produces a biphasic nociceptive behavioral response characterized by an acute phase (0-9 min), followed by a more prolonged inflammatory phase (21-60 min) (FIG. 8E). As demonstrated by calculating the area under curve (AUC), both compounds 3 and 7 significantly reduced the pain score during the inflammatory phase, exhibiting equivalent potency as the reference analogue PD149163, (FIG. 8F). Again, the lack of difference in the duration of effect of these two compounds may be explained by the mode of administration. A summary of analgesic results is presented in Table IV below.

Example 10: Analgesic Profile In Vivo—Chronic Inflammatory and Neuropathic Pain Model Once the in vivo efficacy of these NT macrocyclic compounds is confirmed in the acute pain test, the inventors monitor their ability to reverse the nociceptive behaviors induced either by intraplantar formalin administration (formalin persistent pain model), chronic constriction injury (CCI) of the sciatic nerve (neuropathic pain), or intraplantar injection of the complete Freund's adjuvant (CFA; chronic inflammatory pain model). For comparison purposes. the effectiveness of actual prescribed drugs used as first- or second-line treatment options for the pharmacological management of chronic pain are tested in parallel to the drugs acting at NT receptors.

Example 11: Hypothermia In Vivo

Figure 9A:
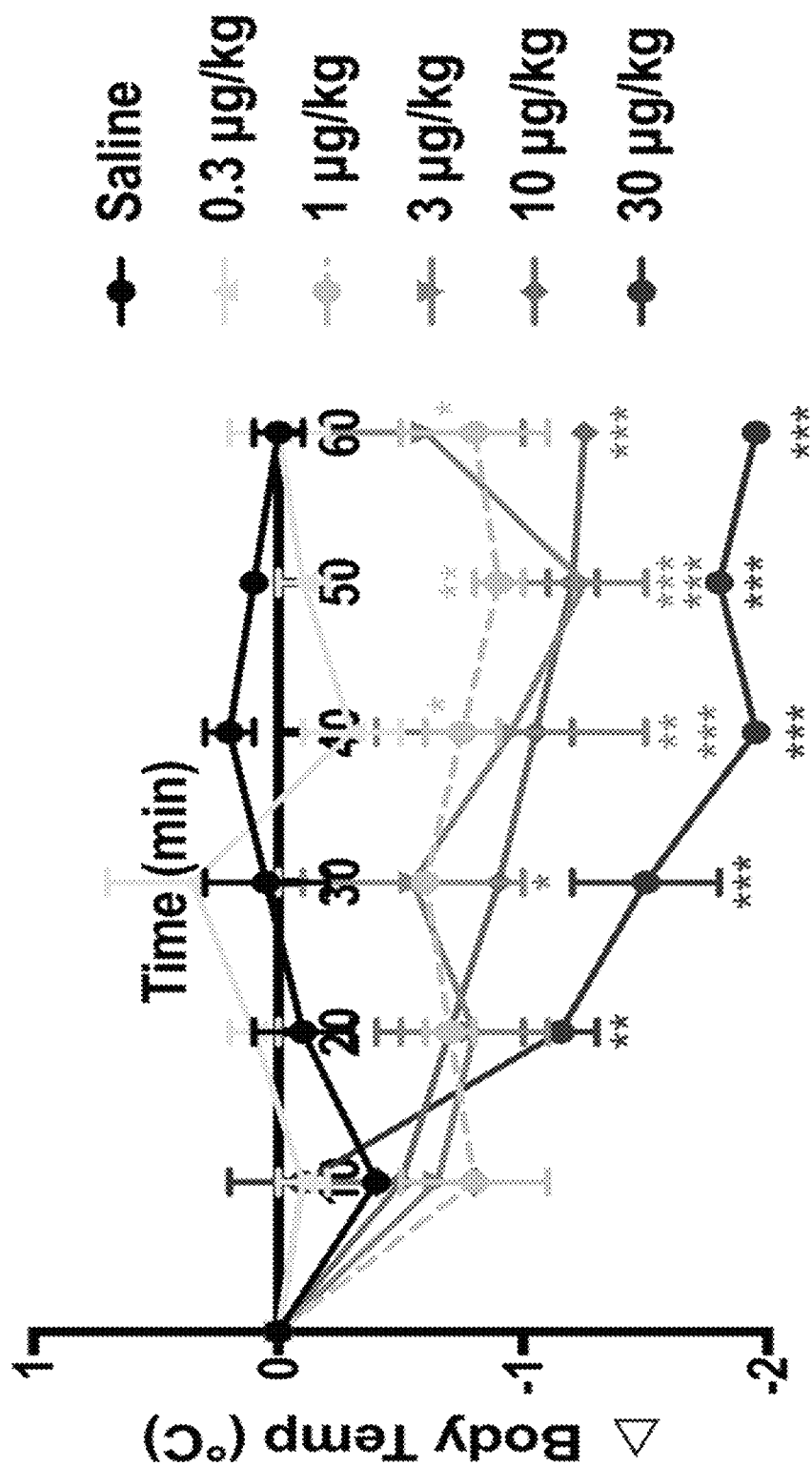
FIGS. 9A-C: Effect of compounds 3, 7 and PD149163 on body temperature and blood pressure.
Figure 9B:
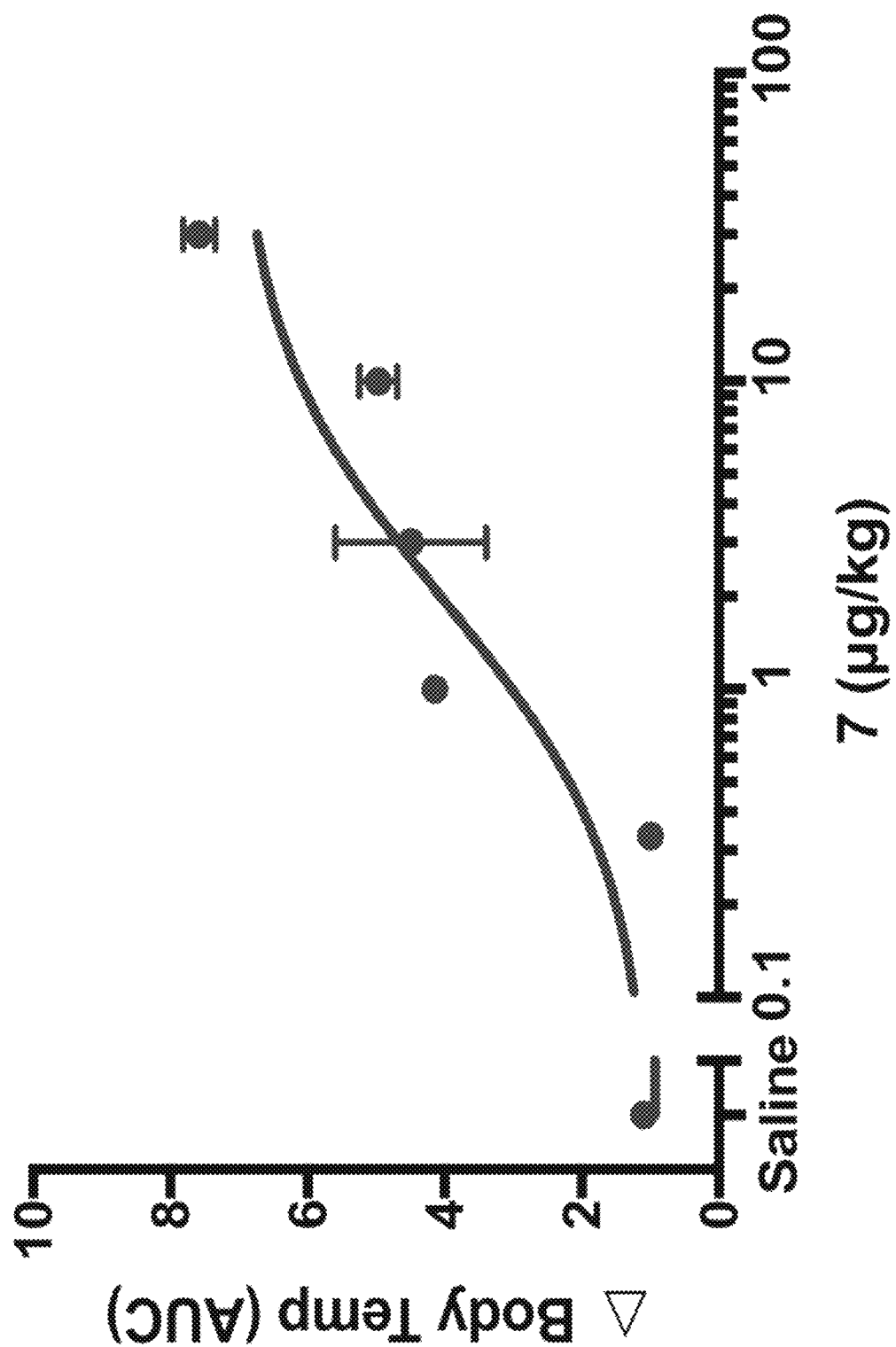
Figure 9C:
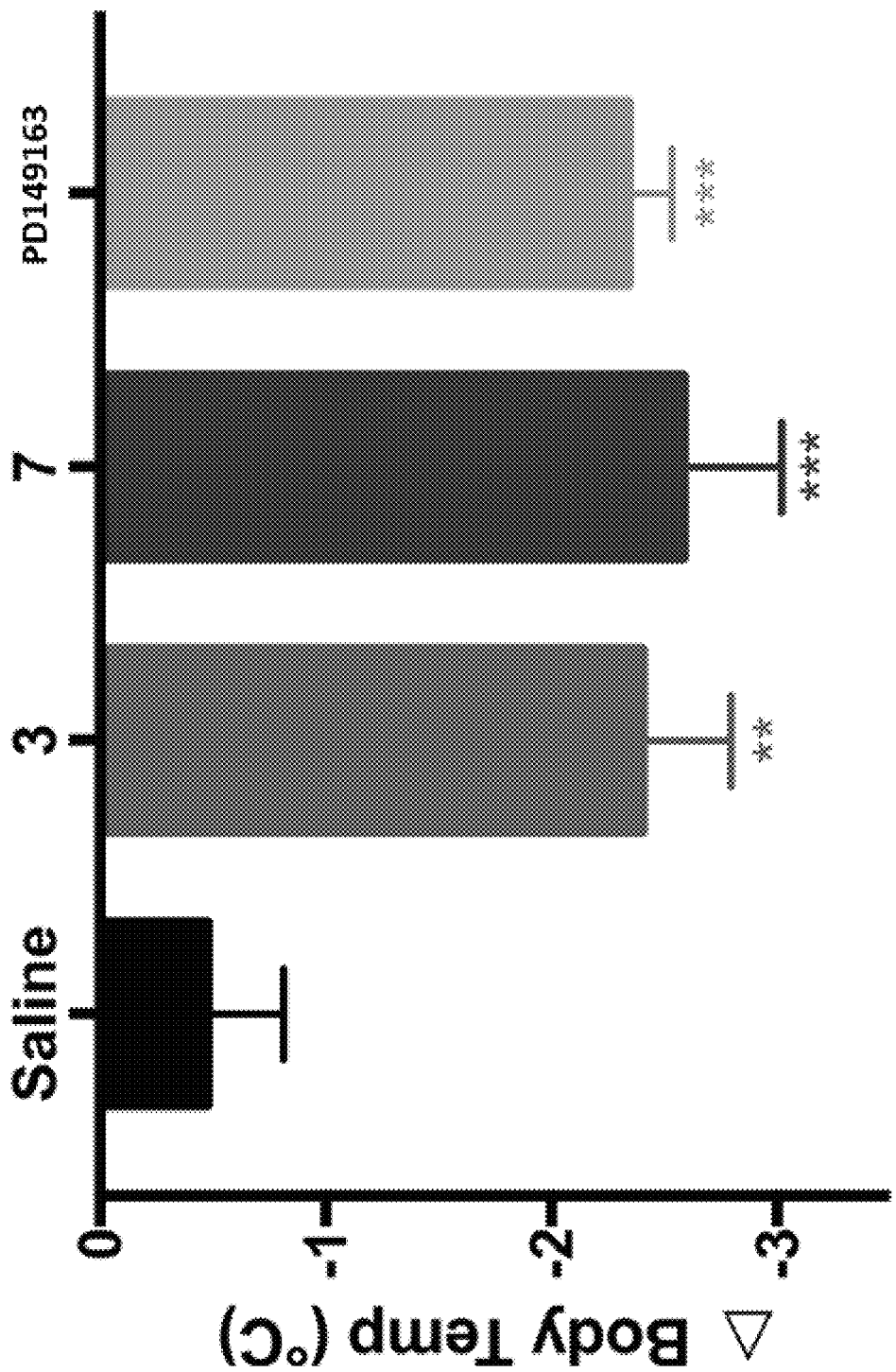

The ability of compounds of the present invention to induce hypothermia after i.v. injection confirmed the dose-dependent effect of compound 7 (FIGS. 9A and 9B and Table IV), with an $ED_{50}$ of 1.96 µ/kg. 60 min after i.t. injection, compounds 3, 7 and PD149163 all induced a temperature drop superior to 2° C. (FIG. 9 C).

Example 12: Hypotension In Vivo

Figure 10:
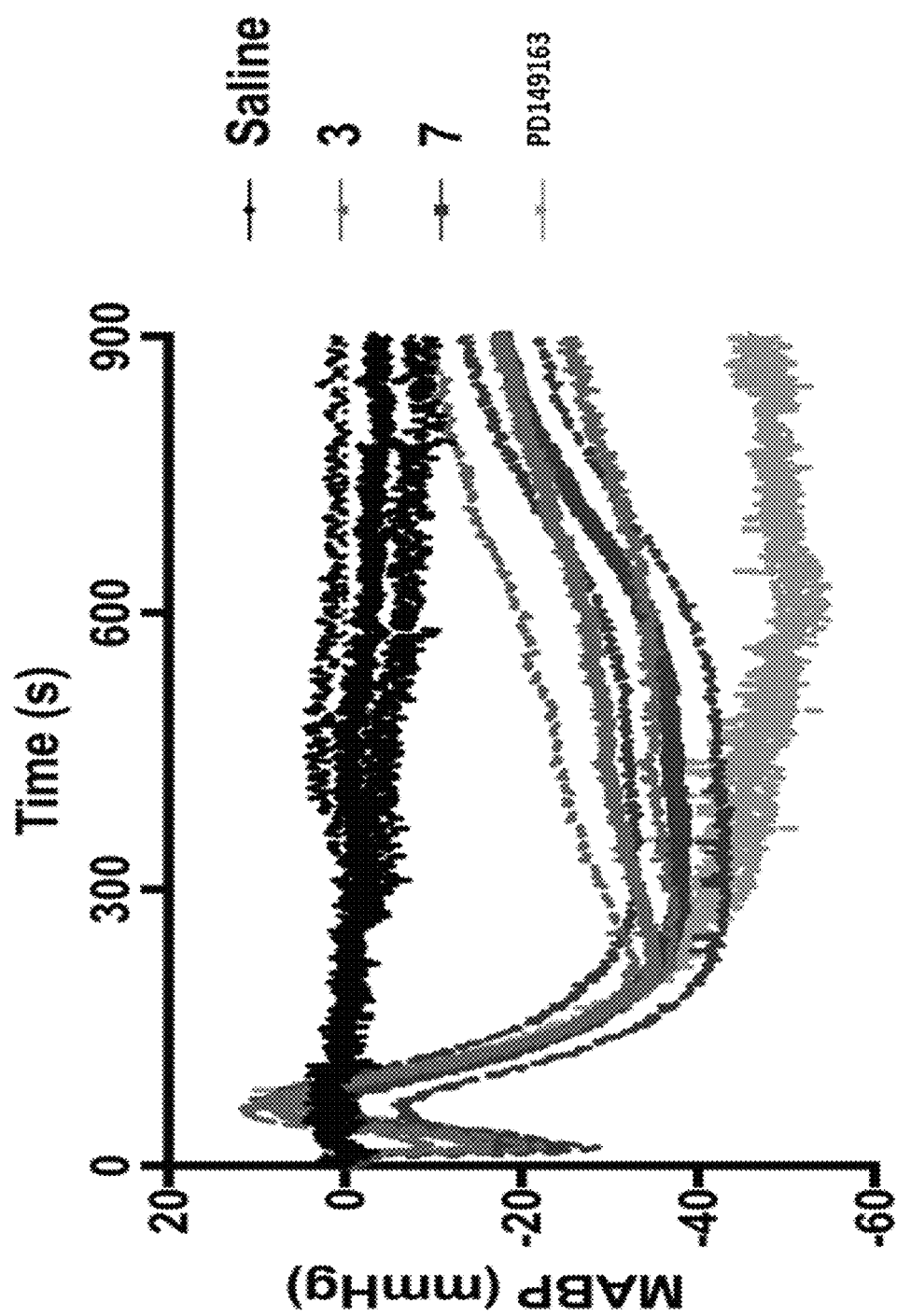
FIG. 10 Effect of compounds 3, 7 and PD149163 on blood pressure. Effect of intravenous injection (i.v.) of compounds 3, 7 and PD149163 at 0.01 mg/kg on blood pressure. Blood pressure changes (ΔMABP) were measured continuously every second over 15 min following i.v. injection. n=3-6 rats (body temperature test) and 3-5 rats (blood pressure measurement) for each compound. Error bars represent mean±SEM. A one-way ANOVA followed by Dunnett's correction was performed. *p<0.05; p<0.01; *p<0.001; as compared to saline-injected rats.

Monitoring arterial blood pressure after i.v. injection of each of compounds 3, 7 and PD149163 at 0.01 mg/kg showed a characteristic triphasic response (FIG. 10 and Table IV). The first phase is a short drop (about −25 mmHg) rapidly followed by a swift return to baseline level (second phase) before a sustained depression (third phase). Tested compounds gave superimposable responses for phases 1 and 2, but blood pressure slowly returned towards baseline in phase 3 for compounds 3 and 7, whereas the drop induced by and PD149163 was more sustained.

Results of examples 9-12 are summarized in Table IV below.

TABLE IV

In vivo effect of compounds of the invention on pain, hypothermia and hypotension.

| Compound | Acute pain (tail beam) (I.T.) | Tonic pain (formalin) (I.T.) | Hypothermia (I.T.) | Hypotension (I.V.) |
|---|---|---|---|---|
| 2 | % MPE at 30 min, 30 µg/kg = 24 | | | |
| 3 | +++ (30 ug/kg) | +++ (30 ug/kg) | +++ (30 ug/kg) | Triphasique (0.01 mg/kg) |
| 7 | +++ (0.3; 1; 3; 10; 30 ug/kg) | +++ (30 ug/kg) | +++ (30 ug/kg) | Triphasique (0.01 mg/kg) |

The scope of the claims should not be limited by the preferred embodiments set forth in the examples, but should be given the broadest interpretation consistent with the description as a whole.

REFERENCES

Ansel H. et. al., Pharmaceutical Dosage Forms and Drug Delivery Systems (6th Ed. 1995) pp. 108-109.
Barelli, H.; Vincent, J. P.; Checler, F. Rat kidney endopeptidase 24.16. Purification, physico-chemical characteristics and differential specificity towards opiates, tachykinins and neurotensin-related peptides. Eur. J. Biochem. 1993, 211, 79-90.
Bernard, Stephen A; Gray, Timothy W.; Buist, Michael D.; Jones, Bruce M.; Silvester, William; Gutteridge, Geoff; Smith, Karen (21 Feb. 2002). "Treatment of Comatose Survivors of Out-of-Hospital Cardiac Arrest with Induced Hypothermia". New England Journal of Medicine. 346 (8): 557-563.
Bingham A L., Hughes D. S., Hursthouse M. B., Lancaster R. W., Tavener S. and Threlfall T. L., 2001. Over one hundred solvates of sulfathiazole Chem. Commun., 2001, 7:603-604.
Bundgaard H ed. Design of Prodrugs. (Elsevier, 1985).
Caira M R et al. 2004. Preparation and Crystal Characterization of a Polymorph, a Monohydrate, and an Ethyl Acetate Solvate of the Antifungal Fluconazole. J Pharm Sci 93 (3), 601-611.
Carraway, R.; Leeman, S. E. The isolation of a new hypotensive peptide, neurotensin, from bovine hypothalami. J. Biol. Chem. 1973, 248, 6854-6861.
Connelly, J. C.; Skidgel, R. A; Schulz, W. W.; Johnson, A. R.; Erdos, E. G. Neutral endopeptidase 24.11 in human neutrophils: cleavage of chemotactic peptide. Proc. Natl. Acad. Sci. U.S.A. 1985, 82, 8737-8741.
Dobner, P. R. Neurotensin and pain modulation. Peptides 2006, 27, 2405-2414. (10) White, J. F.; Noinaj, N.; Shibata, Y.; Love, J.; Kloss, B.; Xu, F.; Gvozdenovic-Jeremic, J.; Shah, P.; Shiloach, J.; Tate, C. G.; Grisshammer, R. Structure of the agonist-bound neurotensin receptor. Nature 2012, 490, 508-513.
Dubuc, I.; Costentin, J.; Doulut, S.; Rodriguez, M.; Martinez, J.; Kitabgi, P. JMV 449: a pseudopeptide analogue of neurotensin-(8-13) with highly potent and long-lasting hypothermic and analgesic effects in the mouse. Eur. J. Pharmacol. 1992, 219, 327-329.
Kleczkowska, P.; Lipkowski, A. W. Neurotensin and neurotensin receptors: characteristic, structure-activity relationship and pain modulation—a review. Eur. J. Pharmacol. 2013, 716, 54-60.
Feng, Y. P.; Wang, J.; Dong, Y. L.; Wang, Y. Y.; Li, Y. Q. The roles of neurotensin and its analogues in pain. Curr. Pharm. Des. 2015, 21, 840-848.
Jarkko Rautio et al., Nat. Rev. Drug Discov., (2008) 7: 255-270).
Krogsgaard-Larsen, et. al., Textbook of Drug Design and Development (2d Ed. 1996) p. 152-191.
Li et al. Tetrahedron Letters, 2017, 58 (24) 2374-2377.
Naruta et al. J. Org. Chem. 1986, 51, 5083-5092.
Nemeroff, C. B.; Osbahr, A. J., 3rd; Manberg, P. J.; Ervin, G. N.; Prange, A. J., Jr. Alterations in nociception and body temperature after intracisternal administration of neurotensin, beta-endorphin, other endogenous peptides, and morphine. Proc. Natl. Acad. Sci. U.S.A. 1979, 76, 5368-5371.
Peberdy, M A; Calaway, C W; Neumar, R W; Geocadin, R G; Zimmerman, J L; Donnino, M; Gabrielli, A; Silvers, S M; Zaritsky, A L; Merchant, R; Vanden Hoek, T L; Kronick, S L; American Heart, Association (2 Nov. 2010). "Part 9: post-cardiac arrest care: 2010 American Heart Association Guidelines for Cardiopulmonary Resuscitation and Emergency Cardiovascular Care.". Circulation. 122 (18 Suppl 3): S768-86.
Pen-Wei Hsieh et al., Curr. Pharm. Des., 2009, 15(19): 2236-2250.
Roussy, G.; Dansereau, M.-A; Doré-Savard, L.; Belleville, K.; Beaudet, N.; Richelson, E.; Sarret, P. Spinal NTS1 Receptors Regulate Nociceptive Signaling in a Rat Formalin Tonic Pain Model. J. Neurochem. 2008, 105 (4), 1100-1114.
van Tonder E. C., Mahlatji M. D., Malan S. F., Liebenberg W., Caira M. R., Song M., and de Villiers M. M. 2004. Preparation and Physicochemical Characterization of 5 Niclosamide Solvates and 1 Hemisolvate AAPS PharmSciTech. 5(1): p. 1-10.

Vincent, B.; Jiracek, J.; Noble, F.; Loog, M.; Roques, B.; Dive, V.; Vincent, J. P.; Checler, F. Contribution of endopeptidase 3.4.24.15 to central neurotensin inactivation. Eur. J. Pharmacol. 1997, 334: 49-53.

The invention claimed is:

1. A compound of formula (I)

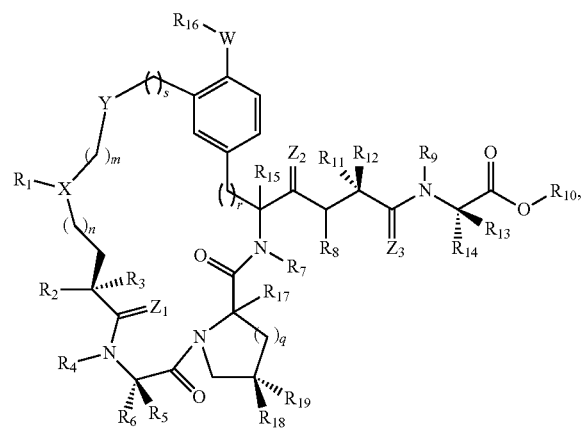

(I)

wherein:
(i) X is —CH and R1=H; or
X is N and R1 is H, (C1-12)alkyl, (C4-C14)aralkyl, $SO_2$(C3-C7) aryl, —$SO_2$(C1-12)alkyl, —$SO_2$aralkyl, —CO(C1-12)alkyl, CO(C4-C14)aralkyl, or —C(=NH)NH2;
(ii) R2 is H or —$CH_3$; and R3 is H, —$NH_2$, -NHalkyl, NHaralkyl, -NHCOalkyl, -NHSO$_2$aryl, or —NH(C=NH)NH$_2$; or
R2 is H, —$NH_2$, -NHalkyl, NHaralkyl, -NHCOalkyl, -NHSO$_2$aryl, or —NH(C=NH)NH$_2$; and R3 is H or —$CH_3$;
(iii) R4, R7, R8 and R9 are each independently H, (C1-12)alkyl, or (C4-C14)aralkyl;
(iv) R5 is H or —$CH_3$; and R6 is -($CH_2$)pNHR20 or the side chain of histidine; or
R6 is H or —$CH_3$; and R5 is -($CH_2$)pNHR20 or the side chain of histidine,
wherein p is 1-5; and R20 is H, —C(=NH)—$NH_2$, (C1-12)alkyl, or (C4-C12)aralkyl;
(v) R10 is H, benzyl, (C4-C14)aralkyl, or (C1-12)alkyl;
(vi) R11 is H or —$CH_3$; and R12 is —$CH_2$Si($CH_3$)$_3$, or the side chain of a valine, alanine, glycine, leucine, isoleucine, allo-isoleucine, tert-butyl glycine, tert-butyl alanine, cyclohexylglycine, cyclopentylglycine, cyclobutylglycine, cyclopropylglycine, norvaline or norleucine; or R12 is H or —CH$_3$; and R11 is —CH$_2$Si(CH$_3$)$_3$, or the side chain of a valine, alanine, glycine, leucine, isoleucine, allo-isoleucine, tert-butyl glycine, tert-butyl alanine, cyclohexylglycine, cyclopentylglycine, cyclobutylglycine, cyclopropylglycine, norvaline or norleucine;

(vii) R13 is H or —CH$_3$; and R14 is the side chain of a valine, alanine, glycine, leucine, isoleucine, alto-isoleucine, tert-butyl glycine, tert-butyl alanine, cyclohexylalanine, cyclopentylalanine, cyclobutylalanine, cyclopropylalanine, norvaline or norleucine; or R14 is H or —CH$_3$; and R13 is the side chain of a valine, alanine, glycine, leucine, isoleucine, alto-isoleucine, tert-butyl glycine, tert-butyl alanine, cyclohexylalanine, cyclopentylalanine, cyclobutylalanine, cyclopropylalanine, norvaline or norleucine;

(viii) R15 is H or —CH$_3$;
(ix) R16 is H, (C1-C12)alkyl, (C4-C14)aralkyl, or C(=O)R21, wherein R21 is (C1-C12)alkyl or (C4-C14)aralkyl;
(x) R17 is H or —CH$_3$;
(xi) R18 is H or —CH$_3$; and R19 is H, —OH, (C1-C10)alkyl, -(C1-C10)Oalkyl or -(C1-C10)NHalkyl; or
R19 is H or —CH$_3$; and R18 is H, —OH, (C1-C10)alkyl, -(C1-C10)Oalkyl or -(C1-C10)NHalkyl;
(xii) m is 1-4;
(xiii) n is 0-4;
(xiv) q is 0-3;
(xv) r is 0-3;
(xvi) s is 0-3;
(xvii) Y is —CH=CH— (E or Z), —CH$_2$—CH$_2$—, or —C≡C—;
(xviii) W is O, —NH or S; and
(xix) Z$_1$, Z$_2$ and Z$_3$ are each independently =O or absent, or an ester, solvate, hydrate or pharmaceutical salt thereof.

2. The compound of claim 1, wherein:
(iv) R5 is H or —CH$_3$; and R6 is-(CH$_2$)pNHR20, wherein p and R20 are as defined in claim 1 or is the side chain of histidine;
(vi) R11 is H or —CH$_3$; and R12 is —CH$_2$Si(CH$_3$)$_3$, or the side chain of a valine, alanine, glycine, leucine, isoleucine, allo-isoleucine, tert-butyl glycine, tert-butyl alanine, cyclohexylglycine, cyclopentylglycine, cyclobutylglycine, cyclopropylglycine, norvaline or norleucine;
(vii) R13 is H or —CH$_3$; and R14 is the side chain of a valine, alanine, glycine, leucine, isoleucine, alto-isoleucine, tert-butyl glycine, tert-butyl alanine, cyclohexylalanine, cyclopentylalanine, cyclobutylalanine, cyclopropylalanine, norvaline or norleucine;
(viii) R15 is (S)-H (S) or (S)-CH$_3$; and
(x) R17 is (S)-H (S) or (S)-CH$_3$.

3. The compound of claim 1, wherein R12 is the side chain of a leucine, isoleucine, alto-isoleucine, tert-butyl glycine, tert-butyl alanine, cyclohexylglycine, cyclopentylglycine, cyclobutylglycine, cyclopropylglycine, norvaline or norleucine.

4. The compound of claim 1, wherein R13 is the side chain of a leucine, isoleucine, alto-isoleucine, tert-butyl glycine, tert-butyl alanine, cyclohexylalanine, cyclopentylalanine, cyclobutylalanine, cyclopropylalanine, norvaline or norleucine.

5. The compound of claim 1, wherein:
(iii) R4, R7, R8 and R9 are each H;
(iv) R5 is H; and R6 is-(CH$_2$)pNHR20;
wherein p is 3 or 4; and R20 is H or —C(=NH)—NH$_2$ or R6 is the side chain of histidine;
(vi) R11 is H; and R12 is the side chain of an isoleucine;
(vii) R13 is H; and R14 is the side chain of a leucine;
(viii) R15 is H;
(x) R17 is H;
(xi) R18 and R19 are each H;
(xiv) q is 1;
(xv) r is 1;
(xvi) s is 1;
(xvii) Y is —CH=CH—;
(xviii) W is O; and/or
(xix) Z$_1$, Z$_2$ and Z$_3$ are each =O, or an ester, solvate, hydrate or pharmaceutical salt thereof.

6. The compound of claim 1, wherein:
(iv) R5 is H; and R6 is-(CH$_2$)pNHR20; wherein p is 4; and R20 is H or R6 is the side chain of a histidine.

7. The compound of claim 1, wherein:
(iv) R5 is H; and R6 is-(CH$_2$)pNHR20; wherein p is 3; and R20 is —C(=NH)—NH$_2$.

8. The compound of claim 1, wherein:
(iv) R5 is H; and R6 is the side chain of a histidine.

9. The composition of claim 1, wherein the compound is of formula (Ia)

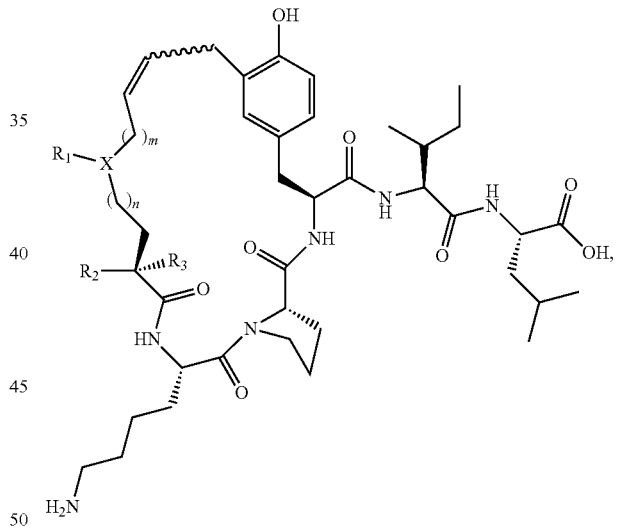

(Ia)

wherein X, R1, R2, R3, n and m are as defined in claim 1, or an ester, solvate, hydrate or pharmaceutical salt thereof.

10. The compound of claim 1, wherein X is N and R1 is H, (C1-12)alkyl, (C4-C14)aralkyl, -SO$_2$(C3-C7)aryl, -SO$_2$(C1-12)alkyl, —SO$_2$aralkyl, -CO(C1-12)alkyl, CO(C4-C14)aralkyl, or —C(=NH)NH$_2$.

11. The compound of claim 1, wherein R1 is H.

12. The compound of claim 1, wherein R1 is S(=O)$_2$(o-nitrophenyl).

13. The compound of claim 1, wherein X is CH and R1 is H.

14. The compound of claim 13, wherein n+m=3.

15. The compound of claim 1, wherein n is 1-3.

16. The compound of claim 1, wherein n is 0.

17. The compound of claim 1, wherein n is 1.

18. The compound of claim 1, wherein n is 2.

19. The compound of claim 1, wherein n is 3.
20. The compound of claim 1, wherein m is 1-3.
21. The compound of claim 1, wherein m is 1.
22. The compound of claim 1, wherein m is 2.
23. The compound of claim 1, wherein m is 3.
24. The compound of claim 1, wherein
R2 is H; and/or
R3 is H or CH$_3$.
25. The compound of claim 1, wherein
R2 is —NH$_2$; and/or
R3 is H or CH$_3$.
26. The compound of claim 1, wherein R2 is-NH2 and R3 is H.
27. The compound of claim 1, wherein R2 and R3 are H.
28. The compound of claim 1, wherein the compound is:

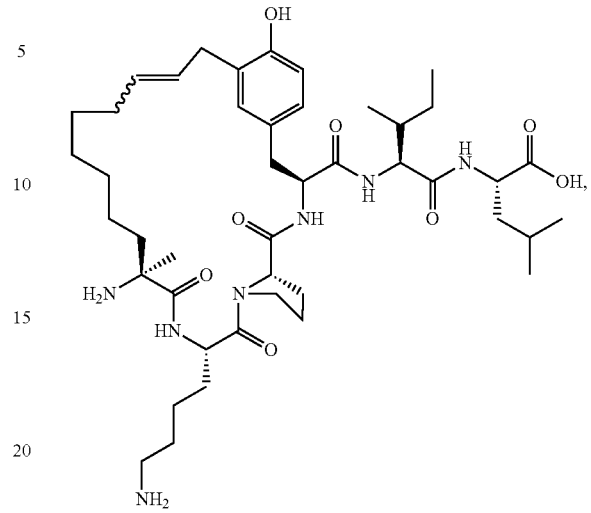

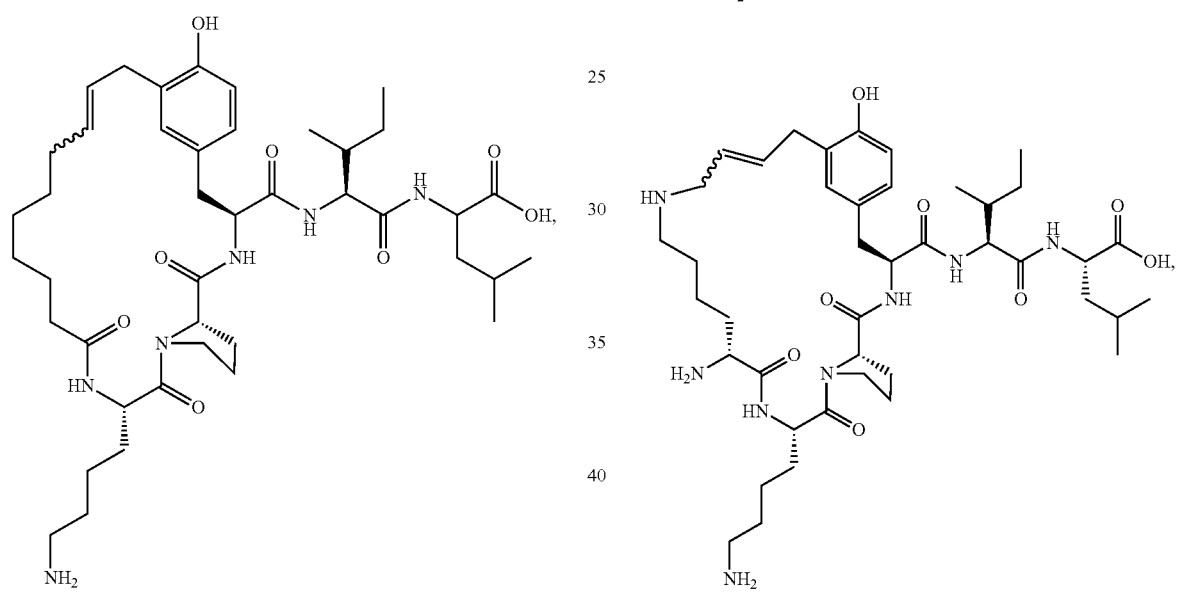

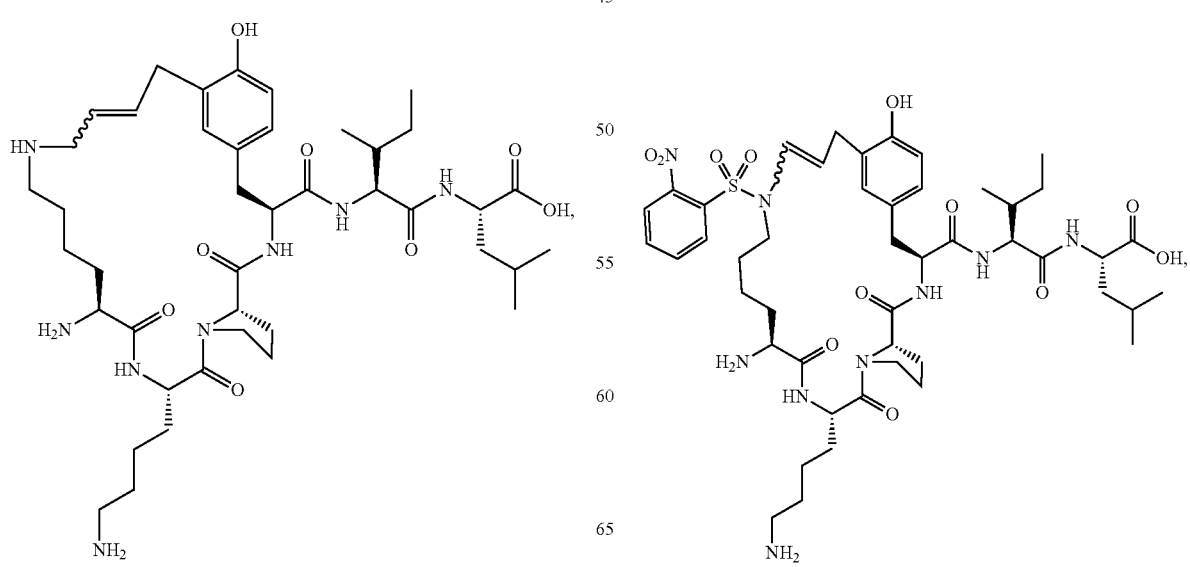

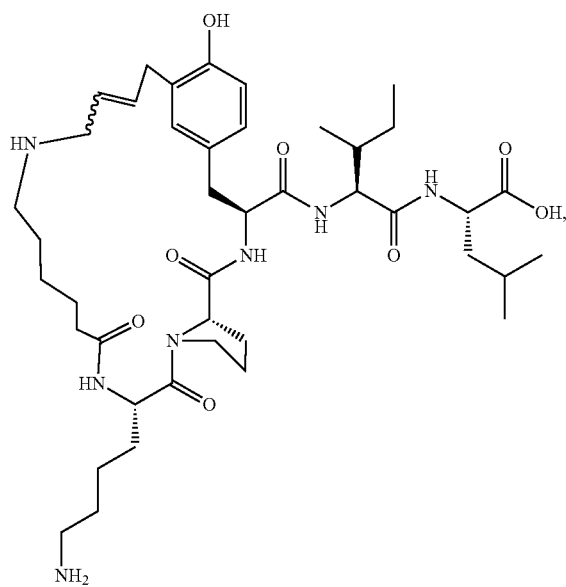
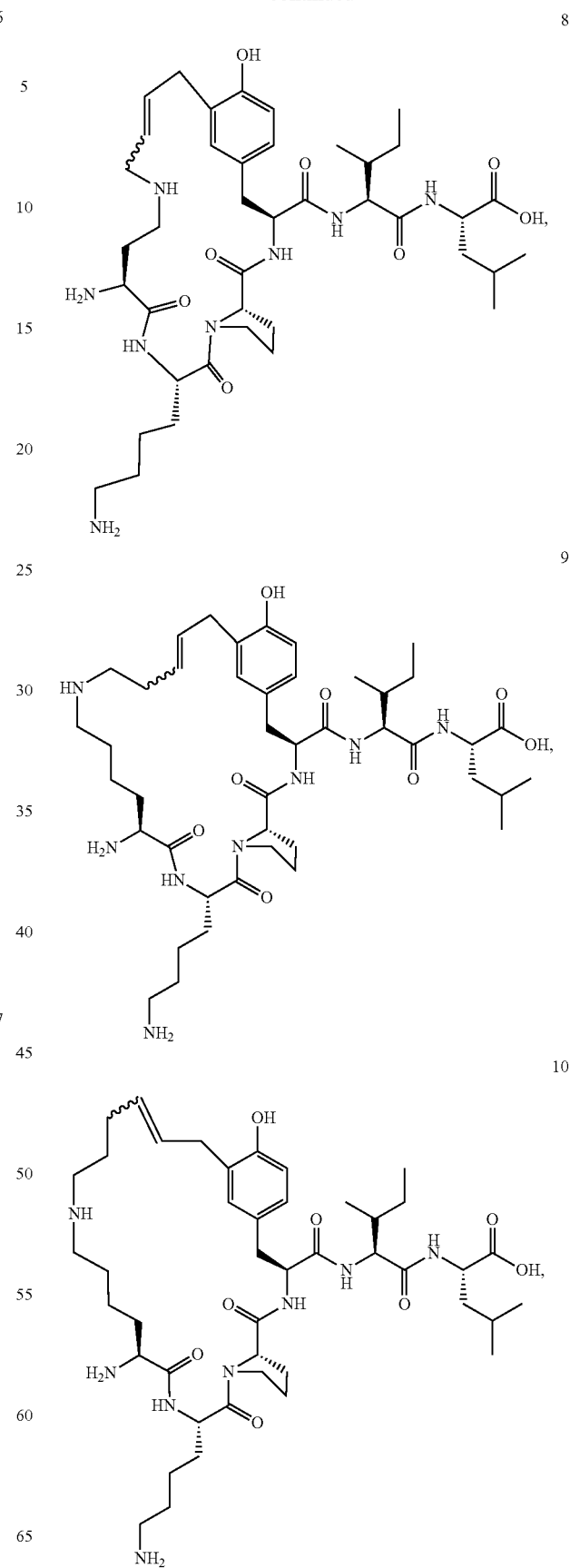

11
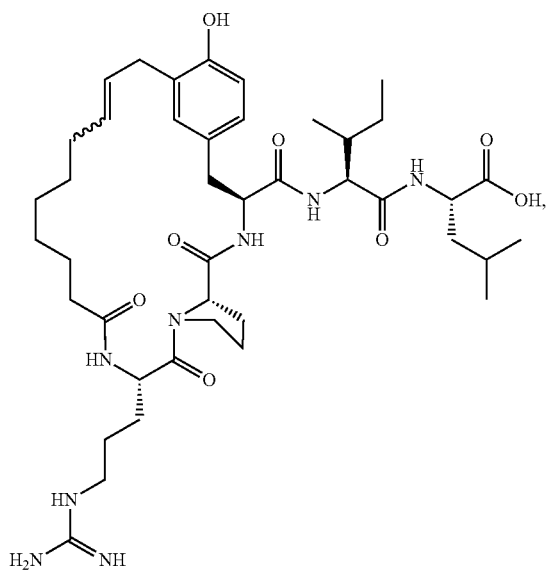
12
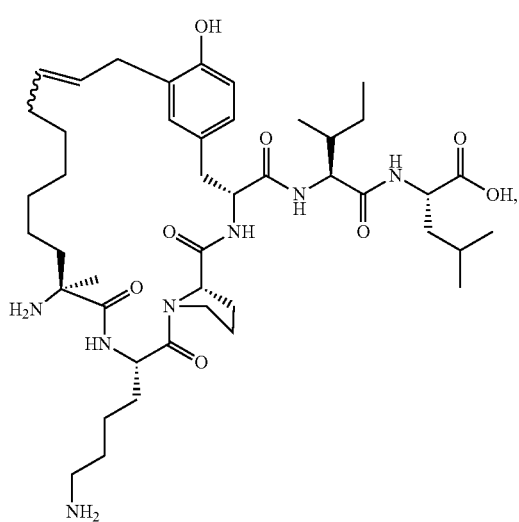
13
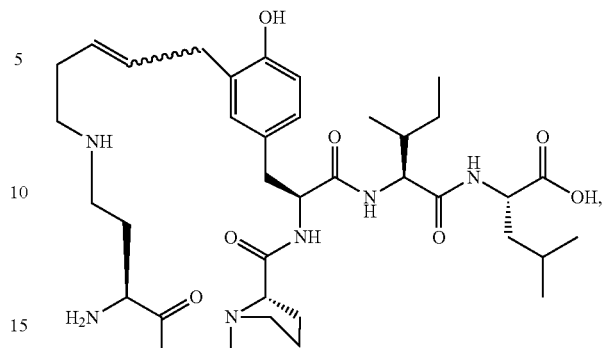
14
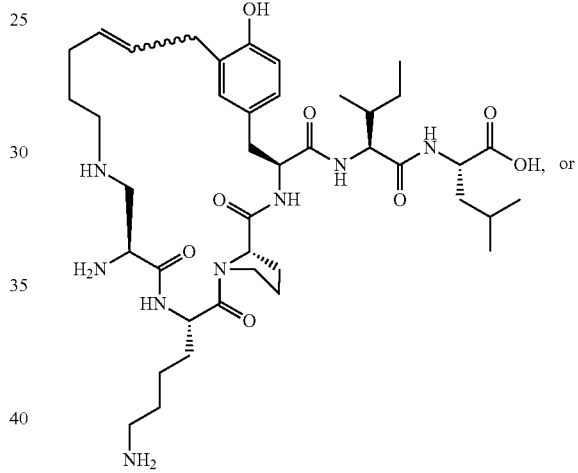
15
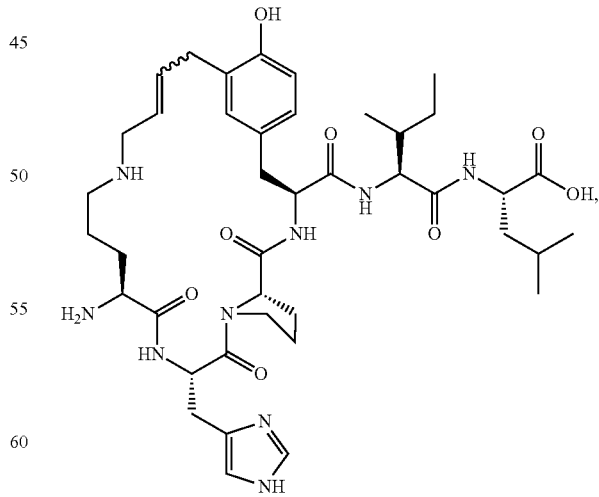
or an ester, solvate, hydrate or pharmaceutical salt thereof.
29. A composition comprising (a) the compound defined claim 1 and (b) (i) at least another compound defined in claim 1; (ii) another antalgic agent; (iii) an anxiolytic agent;

(iv) an antidepressant agent; (v) a pharmaceutically acceptable carrier; or (vi) a combination of at least two of (i) and (v).

30. A method of (a) preventing or treating pain; (b) reducing body temperature; and/or (c) inducing hypotension, in a subject in need thereof, comprising administering to the subject an effective amount of the compound defined in claim 1, or a composition comprising the compound and a pharmaceutically acceptable carrier.

* * * * *